United States Patent
Cerri et al.

(10) Patent No.: US 11,730,746 B2
(45) Date of Patent: Aug. 22, 2023

(54) 17BETA-HETEROCYCLYL-DIGITALIS LIKE COMPOUNDS FOR THE TREATMENT OF HEART FAILURE

(71) Applicant: CVie Therapeutics Limited, Taipei (TW)

(72) Inventors: Alberto Cerri, Milan (IT); Giuseppe Bianchi, Milan (IT); Patrizia Ferrari, Varese (IT); Mara Ferrandi, Milan (IT); Paolo Barassi, Castelvaccana (IT); Antonio Zaza, Milan (IT); Marcella Rocchetti, Brugherio (IT); Carlotta Ronchi, Milan (IT); Shih-Che Hsu, Taipei (TW)

(73) Assignee: CVie Therapeutics Limited, Taipei (TW)

( * ) Notice: Subject to any disclaimer, the term of this patent is extended or adjusted under 35 U.S.C. 154(b) by 126 days.

(21) Appl. No.: 17/263,209

(22) PCT Filed: Jul. 17, 2019

(86) PCT No.: PCT/EP2019/069283
§ 371 (c)(1),
(2) Date: Jan. 26, 2021

(87) PCT Pub. No.: WO2020/020728
PCT Pub. Date: Jan. 30, 2020

(65) Prior Publication Data
US 2021/0283147 A1    Sep. 16, 2021

(30) Foreign Application Priority Data

Jul. 26, 2018 (EP) .................................. 18185753

(51) Int. Cl.
*A61K 31/58* (2006.01)
*A61P 9/04* (2006.01)
*A61K 31/04* (2006.01)
*A61K 31/138* (2006.01)
*A61K 31/196* (2006.01)
*A61K 31/216* (2006.01)
(Continued)

(52) U.S. Cl.
CPC .............. *A61K 31/58* (2013.01); *A61K 31/04* (2013.01); *A61K 31/138* (2013.01); *A61K 31/196* (2013.01); *A61K 31/216* (2013.01); *A61K 31/277* (2013.01); *A61K 31/34* (2013.01); *A61K 31/341* (2013.01); *A61K 31/404* (2013.01); *A61K 31/4035* (2013.01); *A61K 31/41* (2013.01); *A61K 31/4178* (2013.01); *A61K 31/4184* (2013.01); *A61K 31/4422* (2013.01); *A61K 31/496* (2013.01); *A61K 31/50* (2013.01); *A61K 31/517* (2013.01); *A61K 31/549* (2013.01); *A61K 31/554* (2013.01); *A61K 31/585* (2013.01); *A61K 31/64* (2013.01);
(Continued)

(58) Field of Classification Search
CPC ... C07J 19/00; C07J 19/005; C07J 3/00; C07J 31/006; C07J 41/0038; C07J 41/005; C07J 43/003; C07J 5/0015; C07J 9/00; C07J 9/005; A61K 31/04; A61K 31/138; A61K 31/196; A61K 31/216; A61K 31/277; A61K 31/34; A61K 31/341; A61K 31/4035; A61K 31/404; A61K 31/41; A61K 31/4178; A61K 31/4184; A61K 31/4422; A61K 31/496; A61K 31/50; A61K 31/517; A61K 31/549; A61K 31/554; A61K 31/58; A61K 31/585; A61K 31/64; A61K 31/7048; A61K 38/2221; A61K 38/2242; A61K 45/06; A61P 9/04
See application file for complete search history.

(56) References Cited

U.S. PATENT DOCUMENTS 4,534,899 A    8/1985    Sears
5,605,674 A    2/1997    Purewal et al.
(Continued)

FOREIGN PATENT DOCUMENTS

EP    0 576 915 A2    1/1994

OTHER PUBLICATIONS

Gobbini et al., "Digitalis-Like Compounds: The Discovery of the O-Aminoalkyloxime Group as a Very Powerful Substitute for the Unsaturated-Butyrolactone Moiety", 2010, Frontiers in Medicinal Chemistry, vol. 4, pp. 214-236. (Year: 2010).*
(Continued)

*Primary Examiner* — My-Chau T. Tran
(74) *Attorney, Agent, or Firm* — Potter Anderson & Corroon LLP

(57) ABSTRACT

Disclosed are compounds of formula (I), wherein X, Y, Z are annular atoms comprised in a five-membered carbocyclic or heterocyclic ring, selected from the group consisting of CH, NH, N, O, S; said carbocyclic or heterocyclic ring being optionally substituted with amino ($C_1$-$C_4$) linear or branched alkyl or guanidine or guanidino ($C_1$-$C_4$) linear or branched alkyl; with the proviso that the heterocycle ring is not furyl; n is 0 or 1; R is H or OH; the dotted line represents an optional double bond C═C; the thick line represents a bond in the β configuration; the wavy line represents a bond both in the α and β configuration; their enantiomeric and/or diastereomeric mixtures, their pharmaceutically acceptable salts, their solvates, hydrates; their metabolite and metabolic precursors. The compounds of formula (I) are for use as medicaments, in particular for the treatment of acute or chronic heart failure. Oral administration is also possible.

20 Claims, 4 Drawing Sheets

(51) Int. Cl.
| | |
|---|---|
| A61K 31/277 | (2006.01) |
| A61K 31/34 | (2006.01) |
| A61K 31/341 | (2006.01) |
| A61K 31/4035 | (2006.01) |
| A61K 31/404 | (2006.01) |
| A61K 31/41 | (2006.01) |
| A61K 31/4178 | (2006.01) |
| A61K 31/4184 | (2006.01) |
| A61K 31/4422 | (2006.01) |
| A61K 31/496 | (2006.01) |
| A61K 31/50 | (2006.01) |
| A61K 31/517 | (2006.01) |
| A61K 31/549 | (2006.01) |
| A61K 31/554 | (2006.01) |
| A61K 31/585 | (2006.01) |
| A61K 31/64 | (2006.01) |
| A61K 31/7048 | (2006.01) |
| A61K 38/06 | (2006.01) |
| A61K 38/22 | (2006.01) |
| A61K 45/06 | (2006.01) |
| C07J 43/00 | (2006.01) |

(52) U.S. Cl.
CPC .......... A61K 31/7048 (2013.01); A61K 38/06 (2013.01); A61K 38/2221 (2013.01); A61K 38/2242 (2013.01); A61K 45/06 (2013.01); A61P 9/04 (2018.01); C07J 43/003 (2013.01)

(56) References Cited

U.S. PATENT DOCUMENTS

| | | | |
|---|---|---|---|
| 5,716,928 | A | 2/1998 | Benet et al. |
| 5,846,743 | A | 12/1998 | Janmey et al. |
| 5,858,401 | A | 1/1999 | Bhalani et al. |
| 5,874,268 | A | 2/1999 | Meyer |
| 6,007,839 | A | 12/1999 | Mayhew et al. |
| 6,063,400 | A | 5/2000 | Geho et al. |
| 6,261,815 | B1 | 7/2001 | Meyer |
| 6,358,530 | B1 | 3/2002 | Eljamal et al. |
| 6,509,006 | B1 | 1/2003 | Platz et al. |
| 6,589,503 | B1 | 7/2003 | Piwnica-Worms |
| 6,592,904 | B2 | 7/2003 | Platz et al. |
| 7,097,827 | B2 | 8/2006 | Platz et al. |
| 7,109,034 | B2 | 9/2006 | Orwar et al. |
| 7,306,783 | B2 | 12/2007 | Piwnica-Worms |
| 2004/0028670 | A1 | 2/2004 | Carlson et al. |
| 2004/0151766 | A1 | 8/2004 | Monahan et al. |
| 2005/0136121 | A1 | 6/2005 | Kershman et al. |
| 2006/0083737 | A1 | 4/2006 | Minomi et al. |
| 2007/0042031 | A1 | 2/2007 | MacLachlan et al. |
| 2007/0077286 | A1 | 4/2007 | Ishihara et al. |
| 2007/0082042 | A1 | 4/2007 | Park et al. |
| 2007/0110798 | A1 | 5/2007 | Drummond et al. |

OTHER PUBLICATIONS

Gelbart et al., "Cardenolide analogs. 9. Synthesis and biological activity of 17.beta.-carbomethoxyethylene and 17.beta.-cyanoethylene 14.alpha.-H steroids", 1979, J. Med. Chem., 22(3), pp. 287-290. (Year: 1979).*

Pati et al., "Synthesis of 17.beta.-(3'-thiophenyl)-5.beta.-androstane-3.beta.,14.beta.-diol 3-d-glucclpyranoside, an anti-inotropic cardiac glucoside", 1990, Steroids, 55(2), pp. 65-68. (Year: 1990).*

Berge et al., "Pharmaceutical Salts", 1997, Journal of Pharmaceutical Sciences, 66(1), pp. 1-19. (Year: 1997).*

Gobbini et al., "Digitalis-like Compounds: the Discovery of the O-aminoalkyloxime Group as a Very Powerful Substitute for the Unsaturated γ-Butyrolactone Moiety", 2005, Current Medicinal Chemistry, vol. 12, No. 20, pp. 2343-2355. (Year: 2005).*

Abraham, "In-hospital mortality in patients with acute de requiring intravenous vasoactive medications: an analysis from the Acute Decompensated Heart Failure National Registry (Adhere)" J Am Coll Cardiol 46:57-64 (2005).

Alemanni, "Role and mechanism of subcellular Ca2+ distribution in the action of two inotropic agents with different toxicity" J Mol Cell Cardiol 50:910-8 (2011).

Al-Muhammed, "In-vivo studies on dexamethasone sodium phosphate liposomes" J. Microencapsul. 13:293-306 (199)6.

Ashkar, "Dobutamine" Island (FL): StatPearls Publishing, updated 2020 (available at https://www.ncbi.nlm.nih.gov/books/NBK47-0431/).

Bers, "Regulation of Ca2+ and Na+ in Normal Failing Cardia Myocytes" Annals of the NY Academy of Sciences 1080:165-177 (2006).

Bers, "Calcium Cycling and Signaling in Cardiac Myocytes" Ann. Rev Physiol. 70:23-49 (2008).

Braunwald, "The war against heart failure: the Lancet lecture" Lancet 385:812-24 (2015).

Brophy, "Bioavallabllity of oral dexamethasone during high dose steroid therapy in neurological patients" Eur. J. Clin. Pharmacol. 24:103-108 (1983).

Byrne, "Recirculating cardia delivery of AAV2/1SERCA2a improves myocardial function in an experimental model of heart failure in large animals" Gene Therapy 15:1550-1557 (2008).

Cerri, "Synthesis, Cardiotonic Activity, and Structure-Activity Relationships of 17 [beta]-Guanylhydrazone Derivatives of 5[beta]-Androstane-3[beta], 14[beta]-diol Acting on the Na+,K+-ATPase Receptor" J. Med. Chem. 40(21):3483-3488 (1997).

Chonn, "Recent advances in liposomal drug-delivery systems" Curr. Opin. Biotechnol. 6:698-708 (1995).

Courault, "Partialsynthesen von Cardenoliden und Cardenolid-Analogen XIII. Synthese substituierter 12,21-Epoxy-5beta, 14beta-card-20(22)-enoli de" J. Fur Praktische Chemie 330:445-452 (1988).

Dec, "Istaroxime in heart failure new hope or more hype" J Am Coll Cardiol 51:2286-88 (2008).

De Munari, "Structure-based design and synthesis of novel potent Na+,K+-ATPase inhibitors derived from a 5alpha,14alpha-androstane scaffold as positive inotropic compounds" J. Med. Chem. 46:3644-3654 (2003).

Eyles, "Oral Delivery and Fate of Poly(lactic acid) Microsphere—encapsulated Interferon in Rats" J. Pharm. Pharmacol. 49:669-674 (1997).

Ferrandi, "Istaroxime stimulates SERCA2a and accelerates calcium cycling in heart failure by relieving phospholamban inhibition" Br J Pharmacol 169:1849-61 (2013).

Flaherty, "Acute heart failure syndromes in patie disease early assessment and treatment" J Am Coll Cardiol. 53(3):254-63 (2009).

Fotherby, "Bioavailabtlity of orally administered sex steroids used in oral contraception and hormone replacement therapy" Contraception 54:59-69 (1996).

Gao, "Controlled Release of a Contraceptive Steroid from Biodegradable and Injectable Gel Formulations: In Vitro Evaluation" Pharm. Res. 12:857-863 (1995).

Gheorghiade, "Hemodynamic, Echocardiographic, and Neurohormonal Effects of Istaroxime, a Novel Intravenous Inotropic and Lusitropic Agent" J Am Coll Cardiol 51:2276-85 (2008).

Gobbini, "An Expeditious Route to 3β,14β-Dihydroxy-5β-androstane-17β-carboxaldehyde" Synth Comm 27(6):1115-1122 (1997).

Gong, "Levosimendan Treatment for Heart Failure: A Systematic Review and Meta-Analysis" J Cardiothorac Vasc Anesth 29:1415-25 (2015) (accepted author version retrieved at http://dx.doi.org/10.1053/j/jvca.2015.03.023).

Größl, "A Novel Artificial MicroRNA Expressing AAV Vector for Phospholamban Silencing in Cardiomyocytes Improves Ca2+ Uptake into the Sarcoplasmic Reticulum" PLoS One 9:e92188 (2014).

Guzman, "Replacement of the butanolide moiety of digitoxigenin by cyclic Michael acceptor Systems" Can. J. Chem. 59(23):3241-3247 (1981).

Heineke, "Regulation of cardiac hypertrophy by intracellular signalling pathways" Nat Rev 7:589-600 (2006).

Hidalgo-Aragones, "Pharmacokinetics of oestrone-3-O-sulphamate" J. Steroid Biochem. Mol. Biol. 58:611-617 (1996).

(56) References Cited

OTHER PUBLICATIONS

Hoshijima, "Chronic suppression of heart-failure pseudophosphorylated mutant of phospholamban via cardiac rAAV gene delivery" Nat. Med. 8: 864-871 (2002).
Hulot, "Effect of intracoronary administration of AAV1/SERCA2a on ventricular remodelling in patients with advanced systolic heart failure: results from the AGENT-HF randomized phase 2 trial" Eur Heart J 19:1534-1541 (2016).
Iwanaga, "Chronic phospholamban inhibition prevents progressive cardia dysfunction and pathological remodelling after infarction in rats" J Clin Investig 113:727-736 (2004).
Johnson, "Permeation of Steroids through Human Skin" J. Pharm. Sci. 84:1144-1146 (1995).
Jørgensen, "Purification of Na+,K+-ATPase: enzyme sources, preparative problems, and preparation from mammalian kidney" Methods Enzymol. 156:29-43 (1988).
Kaneko, "A pyridone derivative activates SERCA2a by attenuating the inhibitory effect of phospholamban" Eur J Pharmacol 814:1-7 (2017) (accepted author version retrieved at http://dx.doi.org/10.1016/j/ejphar.2017.07.035).
Kaye, "Percutaneous Cardiac Rectrculation-Mediated Gene Transfer of an Inhibitory Phospholamban Peptide Reverses Advanced Heart Failure in Large Animals" J. Am. Coll. Cardiol. 50:253-260 (2007).
Lipskaia, "Sarcoplasmic reticulum Ca2+ ATPase as a therapeutic target for heart failure" Expert Opin Biol Ther 10:29-41 (2010).
Lloyd-Jones. "Lifetime Risk for Developing Congestive Heart Failure" Circulation106:3068-3072 (2002).
Lohse, "What is the Role of B-Adrenergic Signaling in Heart Failure?" Circ Res 93:896-906 (2003).
MacLennan, "Phospholamban: a Crucial Regulator Cardiac Contractility" Nat Rev Mol Cell Biol 4(7): 566-577 (2003).
Meira, "Heart Failure" Lancet 390:1981-1995 (2017).
Micheletti, "Pharmacological profile of the novel inotropic agent (E,Z)-3-((2-aminoethoxy)imino)androstane-6,17-dione hydrochloride (PST2744)" J Pharmacol Exp Ther 303:592-600 (2002).
Micheletti, "Istaroxime, a stimulator of sarcoplasmic reticulum calcium adenosine triphosphatase isoform 2a activity, as a novel therapeutic approach to heart failure" Am J Card 99:24A-32A (2007).
Nakayama, "Ca2+ and Mitochondrial-Dependent Cardiomyocyte Necrosis as a Primary Mediator of Heart Failure" J Clin Invest 117:2431-44 (2007).
Nediani, "Stimulation of cardiac sarcoplasmic reticulum calcium pump by acylphosphatase. Relationship to phospholamban phosphorylation" J Biol Chem. 271:19066-73 (1996).
Ostro, "Use of liposomes as injectable-drug delivery systems" Am. J. Hosp. Pharm. 46:1576-1587 (1989).
Packer, "The Room Where It Happens: A Skeptic's Analysis of the New Heart Failure Guidelines" Journal of Cardiac Failure 22:726-730 (2016) (accepted author version retrieved at http://dx.doi.org/doi:10.1016/j.cardfail.2016.07.433).
Packer, "Why is the use of digitalis withering? Another reason that we need medical heart failure specialists" Eur J Heart Failure 20:851-852 (2018).
Pati, "Synthesis of 17b-(3'-thiophanyl)-5b-androstane-3b, 14b-diol 3-d-glucopyranoside, an anti-inotropic cardiac glucoside" Steroids 55(2):65-68 (1990).
Rao, "Recent developments of collagen-based materials for medical applications and drug delivery systems" J. Biomater Sci. Polym. Ed. 7:623-645 (1995).
Rocchetti, "Modulation of Sarcoplasmic Reticulum Function by Na+/K+ Pump Inhibitors with Different Toxicity: Digoxin and PST2744 [(E,Z)-3-((2-Aminoethoxy)imino) androstane-6,17-dione Hydrochloride]" J Pharmacol Exp Ther 313:207-15 (2005).
Rohatagi, "Pharmacokinetic and pharmacodynamic evaluation of triamcinolone acetonide after intravenous, oral, and inhaled administration" J. Clin. Pharmacol. 35:1187-1193 (1995).
Sato, "Rescue of contractile parameters and myocyte hypertrophy in calsequestrin overexpressing myocardium by phospholamban ablation" JBC 276:9392-9 (2001).
Seidler, "Cyclopiazonic acid is a specific inhibitor of the Ca2+-ATPase of sarcoplasmic reticulum" J Biol Chem. 264:17816-23 (1989).
Shah, "Effects of istaroxime on diastolic stiffness in acute heart failure syndromes" Results from the Hemodynamic, Echocardiographic, and Neurohormonal Effects of istaroxime, a Novel Intravenous Inotropic and Lusitropic Agent: a Randomized Controlled Trial in Patients Hospitalized with Heart Failure (HORIZON-HF) trial Am Heart J 157:1035-41 (2009).
Solomon, "Influence of nonfatal hospitalization for heart failure on subsequent mortality in patients with chronic heart failure" Circulation 116:1482-87 (2007).
Suckau, "Long-term cardiac-targeted RNA interference for the treatment of heart failure restores cardiac function and reduces pathological hypertrophy" Circulation 119:1241-1252 (2009).
Wolff, "Modified cardenolides. V. Replacement of the C-17 lactone substituent by alkylating groups" J. Med. Chem. 13(4):657-663 (1970).
Villaescusa, "Steroids and related natural products. Synthesis of 10(22)-dihydro-23-deoxodigitoxigenin" J. Organic Chem. 37(4) (1972).
International Search Report and Written Opinion in International Application No. PCT/EP2019/069283, dated Sep. 27, 2019.

* cited by examiner

17BETA-HETEROCYCLYL-DIGITALIS LIKE COMPOUNDS FOR THE TREATMENT OF HEART FAILURE

CROSS REFERENCE TO RELATED APPLICATIONS

This is a U.S. national filing, pursuant to 35 U.S.C. § 371, of International Application No. PCT/EP2019/069283, filed Jul. 17, 2019, which claims priority to European Patent Application No. 18185753.3, filed Jul. 26, 2018, the entire contents of which are incorporated by reference herein.

The present invention relates to the field of pharmaceuticals, in particular to 17β-heterocyclyl-digitalis like compounds and their use for the treatment of heart failure.

BACKGROUND OF THE INVENTION

The prevalence of heart failure (HF) is age-dependent, ranging from less than 2% of people younger than 60 years to more than 10% of older than 75 years (Metra M, Teerlink J R Lancet 2017; 390:1981-1995). Most patients with HF have a history of hypertension, coronary artery disease, cardiomyopathies, or valve disease, or a combination of these disorders (Metra M, Teerlink J R Lancet 2017; 390: 1981-1995). The calculated lifetime risk of developing HF is expected to increase and those with hypertension are at higher risk (Lloyd-Jones D M et al. Circulation 2002; 106:3068-3072). Patients with HF have a poor prognosis with high rates of hospital admission and mortality.

Clinical symptoms in HF are caused by a cardiac double pathological feature that consists in an inotropic abnormality, resulting in diminished systolic emptying (systolic dysfunction) and a compliance abnormality in which the ability of the ventricles to suck blood from the venous system is impaired (diastolic dysfunction), thus reducing the amount of blood available for systolic contraction (that is impairment of left ventricle (LV) filling). The impaired contractility and relaxation are the consequence of an abnormal distribution of intracellular $Ca^{2+}$, resulting from reduced $Ca^{2+}$ uptake by the sarcoplasmic reticulum (SR), the intracellular $Ca^{2+}$ store (Bers D et al Ann N.T Acad Sci 2006 1080:165-177). The latter is operated by the $Ca^{2+}$-ATPase of the SR membrane (SERCA2a), an active membrane transport. SERCA2a activity is physiologically limited by its interaction with phospholamban (PLN) (Bers D M. Annu Rev Physiol 2008; 70:23-49; MacLennan D H, Kranias E G. Nat Rev Mol Cell Biol 2003; 4(7): 566-577); such a restrain is normally relieved by PLN phosphorylation by protein kinase A (PKA), a signalling pathway severely depressed as a consequence of HF remodelling (Lohse M et al Circ Res 2003; 93:896-906). Thus, SERCA2a function is impaired in the failing myocardium (Bers D et al Ann N.Y. Acad Sci 2006; 1080:165-177) and this is primarily responsible for reduced $Ca^{2+}$ uptake by the SR. In addition to its consequences on myocyte contractility and relaxation, abnormal $Ca^{2+}$ distribution also facilitates cardiac arrhythmias (Zaza & Rocchetti, Curr Pharm Des 2015; 21:1053-1061) and, on the long term, it accelerates myocytes loss by apoptosis (Nakayama H et al., J Clin Invest 2007; 117:2431-44). Reduced SERCA2a function also increases the energy cost of contraction, because it requires a compensatory increase in $Ca^{2+}$ extrusion through the Na—Ca exchanger (NCX), which is less energy efficient (Lipskaya L et al 2010 Expert Opin Biol Ther 2010; 10:29-41). Substantial evidence indicates that normalization of SERCA2a function restores intracellular $Ca^{2+}$ homeostasis and improves contractility and relaxation of cardiomyocytes and of the heart in-situ (Byrne M J et al., Gene Therapy 2008; 15:1550-1557; Sato et al., JBC 2001; 276:9392-99). To summarize, recovery of SERCA2a function in HF may improve cardiac relaxation and contractility while minimizing arrhythmias, myocardial oxygen consumption and myocyte death (Lipskaia L et al., Expert Opin Biol Ther. 2010; 10:29-41). If in parallel to SERCA2a activation, inhibition of the Na,K-pump can further increase intracellular $Ca^{2+}$ content without inducing excessive cytosolic $Ca^{2+}$ accumulation. Therefore, the combination of Na,K-ATPase inhibition and SERCA2a stimulation may afford further positive inotropy at a reduced risk of arrhythmogenic $Ca^{2+}$ release events. Novel molecules able to combine the enhancement of SR SERCA2a with the inhibition of Na,K-pump may be able to improve systolic and diastolic function and ameliorate luso-inotropic performance in HF. This provides a strong motivation for the search of new luso-inotropic agents minimizing the pro-arrhythmic effects and with a higher safety profile than Digoxin that is able to inhibit Na,K pump but is devoid of SERCA2a stimulatory activity.

Current long-term therapy of HF is centred on prevention of "myocardial remodelling" (β-blockers, ACE inhibitors, aldosterone antagonists), a chronic maladaptive response to reduced contractility, which amplifies the initial damage and underlies disease evolution (Heineke J & Molkentin D Nat Rev 2006; 7:589-600). While this approach has indisputable merit, it does not target impaired "contractility" and "relaxation", which are the functional derangement defining HF and responsible for its symptoms. Indeed, particularly in the advanced disease stages, drugs that increase myocardial contractility/relaxation ("inotropic/lusitropic agents") are still widely used and crucial for patient's management (Metra M, Teerlink J R Lancet 2017; 390:1981-1995). These include sympathomimetic amines (dobutamine) and levosimendan, a $Ca^{2+}$-sensitizer with a strong vasodilator effect. Unfortunately, these agents act by mechanisms with potentially harmful components such as facilitation of life-threatening arrhythmias, increased myocardial oxygen consumption and impairment of an already insufficient coronary blood flow due to the fall in blood pressure caused by vasodilatation (Ashkar H, Makaryus A N StatPearls. Treasure Island (FL): StatPearls Publishing; 2018 January-2017 Dec. 19; Gong B. et al. J Cardiothorac Vase Anesth 2015; 29: 1415-25; EDITORIAL). This limits use of inotropic agents to late disease stages, thus losing the potential benefits of increasing contractility early in the disease course. Furthermore, these agents do not improve patient's prognosis and survival and their therapeutic use must be carefully monitored (Ashkar H, Makaryus A N StatPearls. Treasure Island (FL): StatPearls Publishing; 2018 January-2017 Dec. 19; Gong B. et al. J Cardiothorac Vase Anesth 2015; 29: 1415-25; EDITORIAL).

Among positive inotropes, the cardiac glycoside Digoxin, an inhibitor of the Na,K-ATPase enzymatic activity, has been one of the most commonly prescribed medications in the past. However, its use has been decreasing over the last decades because of the difficulty in maintaining digoxin serum concentration ranges (0.5-0.7 ng/ml) at which digoxin displays its beneficial effects without reaching the threshold level of 0.9 ng/ml above which increased risk of death, mainly due to arrhythmias, has been observed (Packer M Journal of Cardiac Failure 2016; 22:726-730; Packer M Eur J Heart Failure 2018; 20:851-852)

Intensive research is also in progress for the development of HF drugs with mechanisms of action other than positive inotropy. Among many, the agents most investigated and under clinical development are: SERELAXIN-recombinant relaxin 2 mediator; ULARITIDE—recombinant natriuretic peptide; OMECANTIV MECARBIL-cardiac myosin activator; BMS986231-NO donor; ADRECIZUMAB-Adrenomedullin inhibitor; ANX-042-spliced variant of NP; TD1439-Neprylisin (NEP) inhibitor. However, when evaluated in clinical phase 2-3 trials, none of these new agents has met the primary end-point.

The clinical course and prognosis of a patient with chronic heart failure (CHF) is much worse after an episode of acute heart failure (AHFS) (Solomon S D et al. Circulation 2007; 116: 1482-87). AHFS can be defined as the new onset or recurrence of symptoms and signs of heart failure, requiring urgent evaluation and treatment and resulting in unscheduled care or hospital admission. Half of the patients with AHFS have reduced systolic function (HFrEF), representing a target for potential future therapies (Braunwald E. Lancet 2015; 385:812-24). Therapies for AHFS in patients with reduced ejection fraction have focused on alleviating congestion with vasodilators, diuretics, or ultrafiltration or increasing cardiac output with positive inotropes. Although this therapeutic strategy has reduced the risk of sudden cardiac death, the post-discharge event rate remains unacceptably high in patients hospitalized for AHFS. Many unwanted cardiovascular side effects can be caused by the available therapy such as: myocardial ischemia, cardiac injury and arrhythmias consequent to the inotrope therapy, particularly in patients with coronary artery disease (CAD) (Abraham W T et al., J Am Coll Cardiol 2005; 46:57-64; Flaherty J D et al., J Am Coll Cardiol. 2009; 53(3):254-63), hypotension and low perfusion of the peripheral organs (kidney) caused by vasodilators particularly in HF patients with low blood pressure. Accordingly, the main goal during hospitalization is to improve cardiac output without causing cardiac and/or kidney injury. Moreover, there has been little focus on examining or treating an impaired left ventricular (LV) diastolic relaxation that, in the remaining 50% of patients with HF but preserved ejection fraction (EF) is responsible for the symptoms of HF. Also in patients with AHFS who have reduced EF an impairment of ventricular relaxation contributes to the overall failure of cardiac function. A variety of echocardiographic indexes has been developed to measure the cardiac relaxation capacity both in animal models and patients with HF, (e.g., decreased early mitral annular tissue velocity [e'] and decreased early mitral inflow [E] deceleration time [DT]), along with echocardiographic parameters of increased LV filling pressure (e.g., E/e' ratio). Even though the correspondence of the single index changes is not perfectly superimposable in some animal models and patients, their overall changes in animal models of ventricular relaxation impairment are certainly translatable to the human condition and used to study the drug effect in AHFS (Shah S A et al. Am Heart J 2009; 157:1035-41).

Various therapeutic approaches that increase SERCA2a function have been recently investigated. These include SERCA2a overexpression by gene transfer (Byrne et al., Gene Therapy 2008; 15:1550-1557), or PLN inactivation by expression of mutants with negative dominance (Hoshijima M et al. Nat. Med. 2002; 8: 864-871; Iwanaga Y et al. J Clin Investig 2004; 113, 727-736), AdV-shRNA (Suckau L et al. Circulation 2009; 119: 1241-1252), microRNA (Größl et al. PLoS One 2014; 9: e92188) or antibodies (Kaye D M et al J. Am. Coll. Cardiol. 2007; 50:253-260). As highlighted by the negative results of the largest phase 2b clinical trial applying SERCA2a gene delivery in HF (CUPID 2), these approaches suffer from major problems in construct delivery (viral vectors etc.) and dose adjustment that are far from being solved (Hulot J S Eur Heart J 2016; 19:1534-1541). A small-molecule (pyridone derivative) inhibiting PLN, structurally different from istaroxime, has been recently described (Kaneko M. et al. Eur J Pharmacol 2017; 814:1-7).

Hence, the development of a small-molecule SERCA2a activator would be advantageous for treating HF and still represents a very promising strategy.

Istaroxime is a new small-molecule drug under clinical development for the treatment of AHFS that is endowed of the double mechanism of action of inhibiting the $Na^+/K^+$ pump (Micheletti et al J Pharmacol Exp Ther 2002; 303: 592-600) while activating SERCA2a (Rocchetti M et al. J Pharmacol Exp Ther 2005; 313:207-15). At the same level of inotropy, the proarrhythmic effect of istaroxime is considerably lower than that of digoxin, a pure $Na^+/K^+$ pump inhibitor (Rocchetti M et al. J Pharmacol Exp Ther. 2005; 313:207-15). This suggests that, by improving $Ca^{2+}$ clearance from the cytosol (Alemanni J Mol Cell Cardiol 2011; 50:910-8), SERCA2a stimulation may also minimize the proarrhythmic effect of $Na^+/K^+$ pump blockade (Rocchetti M et al. J Pharmacol Exp Ther 2005; 313:207-15, Zaza & Rocchetti, Curr Parm Des 2015: 21:1053-1061) while preserving its inotropic effect. The reduction of the proarrhythmic effect by istaroxime has been confirmed in clinical studies (Georghiade M et al J Am Coll Cardiol 2008; 51:2276-85).

In HF patients, istaroxime infusion improved both systolic and diastolic functions. Amelioration of systolic function was detected as increases in systolic tissue velocity (S') and in the slope of end-systolic elastance (ESPVR slope); increased diastolic compliance was revealed by an increment in diastolic tissue velocity (E') and decreased end-diastolic elastance (EDPVR slope) (Shah S A et al. Am Heart J 2009; 157:1035-41). Albeit endowed of an excellent pharmacodynamic profile, istaroxime is not suitable for chronic administration because it has poor GI absorption, high clearance rate and contains a potential genotoxic moiety (oxime); therefore, this agent has been developed for intravenous infusion in hospitalized patients with AHFS only (Dec G W J Am Coll Cardiol 2008; 51:2286-88; Shah S A et al. Am Heart J 2009; 157:1035-41).

Istaroxime is disclosed in EP0825197 and in S. De Munari, et al., J. Med. Chem. 2003, 64, 3644-3654 and is compound (3Z,5a)-3-[(2-Aminoethoxy)imino]androstane-6, 17-dione.

Despite its favourable activity in the treatment of heart failure, Istaroxime is not completely devoid of drawbacks.

The aminoethoxyimino moiety of the molecule undergoes metabolic transformation which can lead to possible genotoxicity.

Further, Istaroxime is active only by intravenous administration, therefore, it can be administered only in hospitals and related environments. Istaroxime administration requires well-trained medical personnel and is not suitable for chronic therapy.

Accordingly, there is a long-felt need for a compound for use in the treatment of heart failure endowed with positive inotropic and positive lusitropic effect, which is devoid of genotoxicity and can be administered preferably by oral route.

The present invention satisfies the above needs and overcomes the problem of prior art.

SUMMARY OF THE INVENTION

It has now been found that 17β-heterocyclyl-digitalis-like compounds of formula (I)

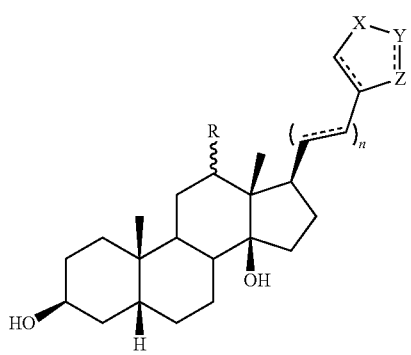

(I)

wherein X, Y, Z are annular atoms comprised in a five-membered carbocyclic or heterocyclic ring, selected from the group consisting of CH, NH, N, O, S; said carbocyclic or heterocyclic ring being optionally substituted with amino ($C_1$-$C_4$) linear or branched alkyl or guanidine or guanidino ($C_1$-$C_4$) linear or branched alkyl;
with the proviso that the heterocycle ring is not furyl;
n is 0 or 1;
R is H or OH;
the dotted line represents an optional double bond C═C; the thick line represents a bond in the β configuration; the wavy line represents a bond both in the α and β configuration;
their enantiomeric and/or diastereomeric mixtures, their pharmaceutically acceptable salts, their solvates, hydrates; their metabolite and metabolic precursors.

In the context of the present invention, metabolite and metabolic precursor mean active metabolite and metabolic precursor, namely a compound of formula (I) which has been transformed by a metabolic reaction, but substantially maintains or increases the pharmacological activity.

Examples of metabolites or metabolic precursors are hydroxylated, carboxylated, sulphonated, glycosylated, glycuronated, methylated or demethylated oxidated or reduced derivatives of the compounds of formula (I).

Some compounds of formula (I) can also be prodrugs of the active forms.

Where the compounds of formula (I) can exhibit tautomerism, the formula is intended to cover all tautomers; the invention includes within its scope all the possible stereoisomers, Z and E isomers, optical isomers, enantiomers and their mixtures.

Also the pharmaceutically acceptable salts are included in the scope of the invention. Pharmaceutically acceptable salts are salts which retain the biological activity of the base compound and are derived from such known pharmacologically acceptable acids such as, e. g., hydrochloric, hydrobromic, sulfuric, phosphoric, nitric, fumaric, succinic, oxalic, malic, tartaric, maleic, citric, methanesulfonic or benzoic acid and others commonly used in the art, see for example Pharmaceutical Salts and Co-crystals; Editors: Johan Wouters, Luc Quéré, RSC Publishing.

The $C_1$-$C_4$ alkyl group may be branched or straight chains or cyclic groups, e.g. methyl, ethyl, n-propyl, i-propyl, n-butyl, i-butyl, t-butyl, cyclopropyl, methylcyclopropyl or cyclobutyl.

Some compounds of formula (I) can also be prodrugs of the active forms.

Further object of the present invention are the said compounds of general formula (I) for use as medicaments, in particular for the treatment of heart failure.

A further object of the present invention are pharmaceutical compositions comprising one or more of the compounds of formula (I), optionally in combination with other therapeutically active ingredients.

The above and other objects of the present invention will be now disclosed in detail also by means of examples and Figures.

DETAILED DESCRIPTION OF THE INVENTION

Figure 1:
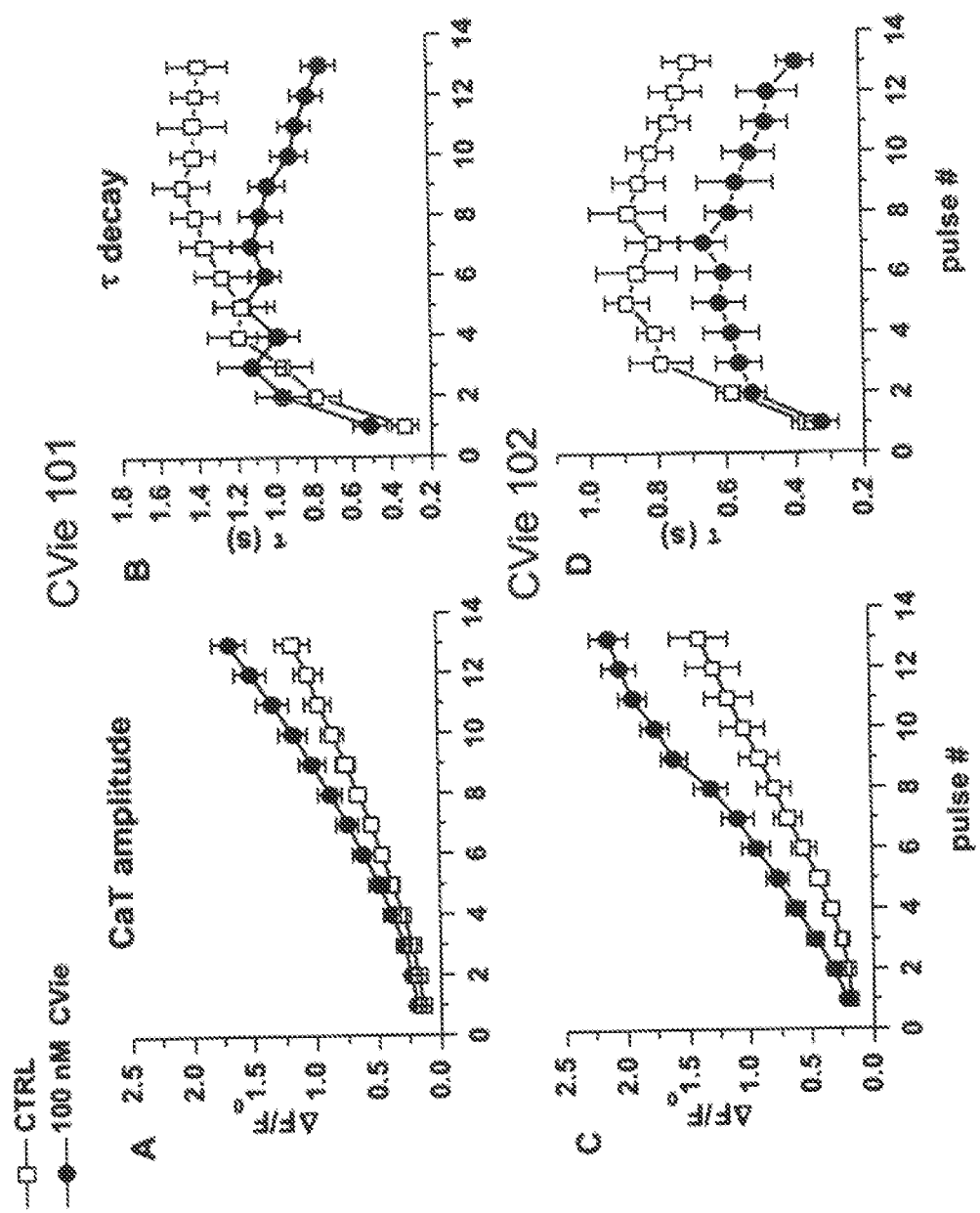
FIG. 1 shows the effects of CVie 101 and CVie 102 on SR $Ca^{2+}$ uptake. Data points are mean±SE. Effects of CVie 101 (A-B) and CVie 102 (C-D) on $Ca^{2+}$ transient (CaT) amplitude and time constant (τ) of CaT decay. Differences between CVie 101 or CVie 102 vs CTRL curves were statistically significant (p<0.05) according to two-way ANOVA. In all protocols N≥13 for CVie 101 and N≥11 for CVie 102.

Within the meanings of the present invention, the five membered carbocyclic residue in position 17β of formula (I) is selected from cyclopentadienyl, cyclopentenyl, cyclopentyl.

Within the meanings of the present invention, the five membered heterocyclic residue in formula (I) is selected from pyrrolyl, thiophenyl, pyrazolyl, imidazolyl, oxazolyl, isoxazolyl, dioxolanyl, dithiolanyl, triazolyl, oxadiazolyl, thiadiazolyl, dioxazolyl, dithiazolyl, tetrazolyl, dithiolanyl, dioxolanyl, dioxolenyl, thiazolyl, isothiazolyl and all their hydrogenated or partially hydrogenated derivatives. The heterocyclic groups may have aromatic or non aromatic character and can be bound to the 17-position by any available position on the ring.

Within the meanings of the present invention, the $C_1$-$C_4$ alkyl group in formula (I) means a branched or straight chain or a cyclic group, e.g. methyl, ethyl, n-propyl, i-propyl, n-butyl, i-butyl, t-butyl, cyclopropyl, methylcyclopropyl or cyclobutyl.

Within the meanings of the present invention, a pharmaceutically acceptable salt is a salt which retains or improves the biological activity or pharmacokinetics of the compound of formula (I) and is derived from known pharmacologically acceptable acids.

According to a first preferred embodiment of the present invention, the compounds of formula (I) are those in which the symbol n is 0.

According to a second preferred embodiment of the present invention, the compounds of formula (I) are those in which the heterocycle group in position 17β is selected form the group consisting of imidazolyl, pyrazolyl, thiazolyl, isoxazolyl, the corresponding dihydro- and tetrahydro derivatives.

According to a third preferred embodiment of the present invention, the compounds of formula (I) are those in which the heterocycle group is selected form the group consisting of imidazolyl, pyrazolyl, thiazolyl, isoxazolyl and is substituted by a amino($C_1$-$C_4$) linear or branched alkyl or guanidine.

According to a fourth preferred embodiment of the present invention, the compounds of formula (I) are those in which R is beta OH.

According to a fifth preferred embodiment of the present invention, the compounds of formula (I) are those in which the symbol n is 1 and there is a double bond.

According to a sixth preferred embodiment of the present invention, the compounds of formula (I) are those in which the symbol n is 1 and there is a single bond.

According to a preferred embodiment of the present invention, the compounds of formula (I) are selected from the group consisting of:

3β-hydroxy-5β-10β-methyl-13β-methyl-14β-hydroxy-17β-(imidazol-4-yl)androstane;
3β-hydroxy-5β-10β-methyl-13β-methyl-14β-hydroxy-17β-(2-guanidino-thiazol-4-yl)androstane;
3β-hydroxy-5β-10β-methyl-12β-hydroxy-13β-methyl-14β-hydroxy-17β-(imidazol-4-yl)androstane;
3β-hydroxy-5β-10β-methyl-12β-hydroxy-13β-methyl-14β-hydroxy-17β-(2-guanidino-thiazol-4-yl)androstane;
3β-hydroxy-5β-10β-methyl-13β-methyl-14β-hydroxy-17β-(N-(3-aminopropyl)-imidazol-4-yl)androstane;
3β-hydroxy-5β-10β-methyl-13β-methyl-14β-hydroxy-17β-(pyrazol-3-yl)androstane;
3β-hydroxy-5β-10β-methyl-13β-methyl-14β-hydroxy-17β-((5-(3-aminopropyl)-isoxazol-3-yl))androstane;
3β-hydroxy-5β-10β-methyl-13β-methyl-14β-hydroxy-17β-((5-(3-aminopropyl)-isoxazol-3-yl)-ethyl)androstane;
3β-hydroxy-5β-10β-methyl-13β-methyl-14β-hydroxy-17β-(5-(2-aminoethyl)-isoxazol-3-yl)-ethyl)androstane;
3β-hydroxy-5β-10β-methyl-13β-methyl-14β-hydroxy-17β-(5-(2-aminomethyl)-isoxazol-3-yl)-ethenyl)androstane;

The invention furthermore provides a process for the preparation of compounds of general formula (I).

A further object of the present invention relates to pharmaceutical compositions and formulations and their use for treating, ameliorating, reversing, or abating or diminishing the symptoms of, or preventing acute or chronic heart failure. Because defective intracellular $Ca^{2+}$ distribution has a role in the myocardial remodelling process, its correction by SERCA2a stimulation may counter it. Thus, evolution of an initial and compensated derangement in contractility to overt heart failure may be prevented.

Preparation of the Compounds of Formula (I)

Generally, compounds of formula (I) wherein R is H are prepared starting from digitoxigenin whereas compounds of formula (I) wherein R is β-OH are prepared starting from digoxigenin.

Both digitoxigenin and digoxigenin are commercial products or can be prepared according to well-known methods. For example, digoxigenin can be prepared starting from digoxin.

Compounds of formula (I) wherein R is H can be prepared starting from digitoxigenin to arrive to intermediate (3).

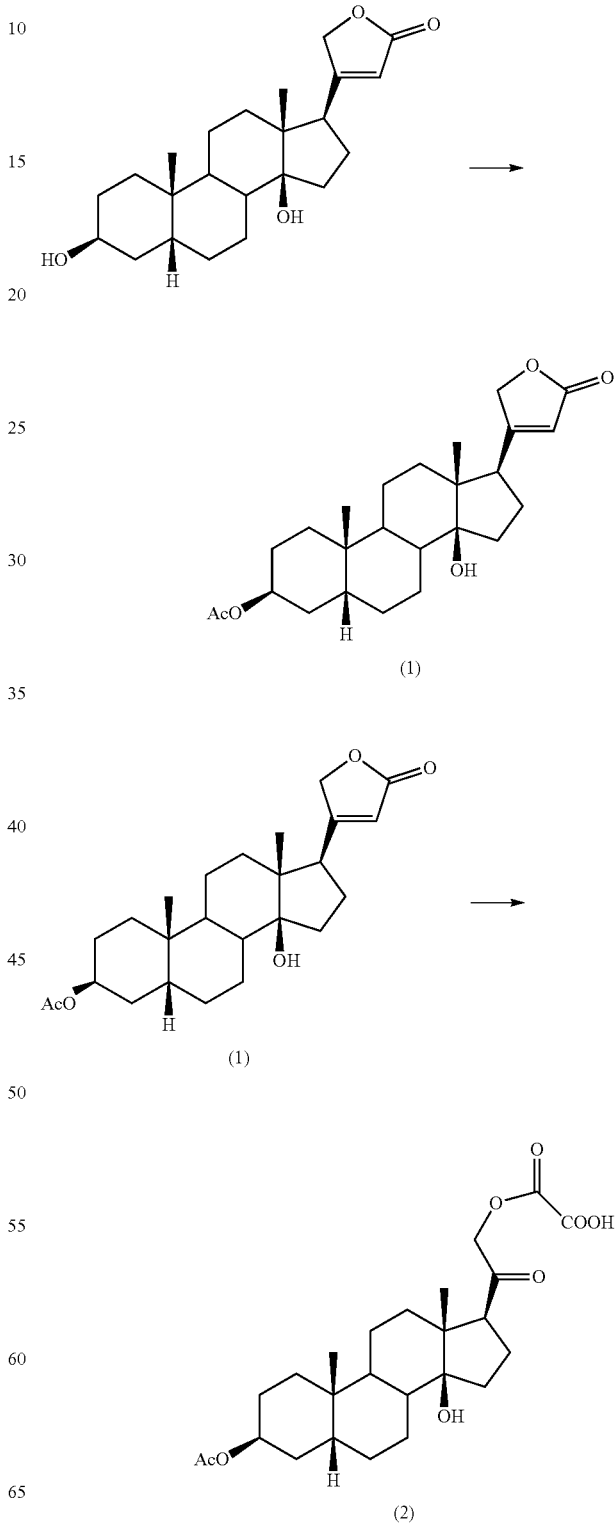

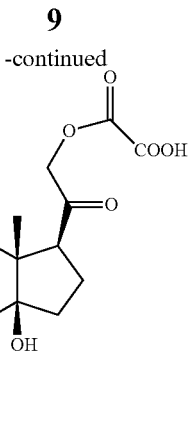

(2)

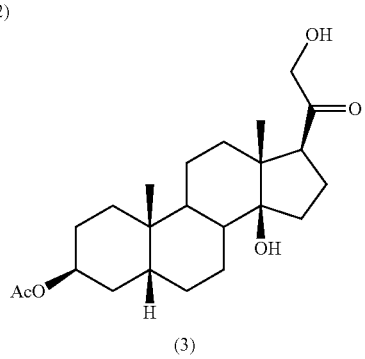

(3)

Digitoxigenin is treated with a suitable reactant in order to protect hydroxy group in position 3. Suitable protecting groups are well-known in the art, for example, 3-OH can be protected by acylation, for example acetylation, which is a conventional reaction. For example, digitoxigenin can be reacted with acetic anhydride in an organic solvent, preferably a nitrogenated solvent, such as pyridine, preferably in inert atmosphere, for example under Argon atmosphere. Preferably an esterification catalyst is used, such as 4-dimethylaminopyridine (DMAP) or other conventional catalysts. The reaction temperature is controlled and the reaction is preferably carried out at room temperature for a time sufficient to bring the reaction to completion. Thereafter, the solvent is removed by evaporation, preferably under reduced pressure (co-evaporation with other solvents is possible). The working up of the reaction is done according to well-known methods, for example taking the residue with water and leaving at room temperature for a convenient time. The resulting solid can be collected, for example by filtration, washed with water and dried, preferably under vacuum. The obtained product (1) can be used in the next steps without need of any further purification.

Intermediate (1) is then subjected to oxidation reaction to open the lactone ring in 17- to give intermediate (2). This kind of reaction is well-known to the skilled person and can be retrieved in the technical literature. By way of example, intermediate (2) is dissolved in an organic solvent, such as acetone, and the oxidizing agent is added. For example, a solution of $NaIO_4$ and $RuO_2$ hydrate in water is convenient, even though other known agents can be used as well. If needed, further additions of the oxidizing agent can be done. The reaction temperature is not limiting and can be determined according to the nature of the oxidizing agent. Once the oxidation reaction has gone to completion, any excess of oxidizing agent is quenched according to well-known methods. For example, isopropanol can be used as quenching agent when $NaIO_4$ and $RuO_2$ hydrate system is used. Any solid is separated from the reaction mixture, for example by filtration, the reaction volume is preferably reduced by evaporation, conveniently under reduced pressure and the residue extracted with a suitable solvent, such as ethyl acetate (AcOEt). The organic phase is then washed, preferably with brine, then dried in a conventional manner, such as for example with $MgSO_4$, filtered if necessary and the solvent removed, for example under vacuum. Intermediate (2) can used in the next steps without any further purification.

Intermediate (3) is obtained by hydrolyzing under mild conditions compound (2), dissolved in a suitable solvent, for example in an alcohol, such as methanol, with, for example, aqueous $KHCO_3$ for a time sufficient to restore the primary alcohol in position 17. The organic solvent is then removed, preferably under reduced pressure, and the residue extracted with a solvent, such as dichloromethane. The organic phase is washed, for example with brine then dried in a conventional manner, filtered if necessary and the solvent removed, preferably under reduced pressure. The residue is purified according to well-known methods, for example flash chromatography ($SiO_2$) eluting with appropriate eluent (for example 7:3 cyclohexane/AcOEt).

Compound (3) is the intermediate used to prepare most of the 17β-heterocyclyl and carbocyclyl compounds of formula (I). Depending on the final product, namely the type of hetero- or carbocycle to be obtained in the final compound of formula (I), the skilled person can resort to the common general knowledge to find the suitable synthetic pathway, for example Advanced Organic Chemistry Pt. B: Reactions and Synthesis by Francis A. Carey and Richard J. Sundberg and The Chemistry of Heterocycles: Structures, Reactions, Synthesis, and Applications, Edition 3 by Theophil Eicher, Siegfried Hauptmann, Andreas Speicher.

By way of example, for compounds of formula (I) wherein X is NH, Y is CH and Z is N, namely, the heterocycle is imidazolyl, compound (3) is transformed into intermediate (4) according to the following scheme.

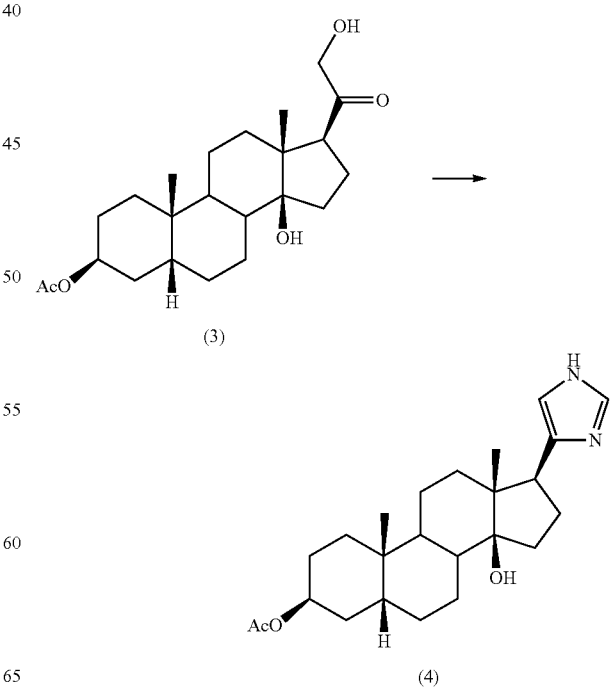

Generally, compound (3) is dissolved in an organic solvent, for example in an alcohol, such as ethanol, and treated with formaldehyde. Conveniently, a solution of Cu(OAc)$_2$ in water and ammonium is added. The reaction mixture is heated, preferably to reflux for time sufficient for reaction completion. The solvent is then removed, preferably under reduced pressure, and the residue is dissolved in an organic solvent, such as AcOEt and repeatedly washed with brine. The organic phases are collected and the aqueous phase extracted the same solvent. The pooled organic phases are dried, for example over MgSO$_4$, filtered, preferably over a celite pad and the solvent is removed, preferably under reduced pressure, giving 13.34 g (96%) of (4) as a solid, used in the next step without any further purification.

Finally, intermediate (4) is converted into the final product by restoring the 3-hydroxy group by means of conventional methods, according to the following scheme

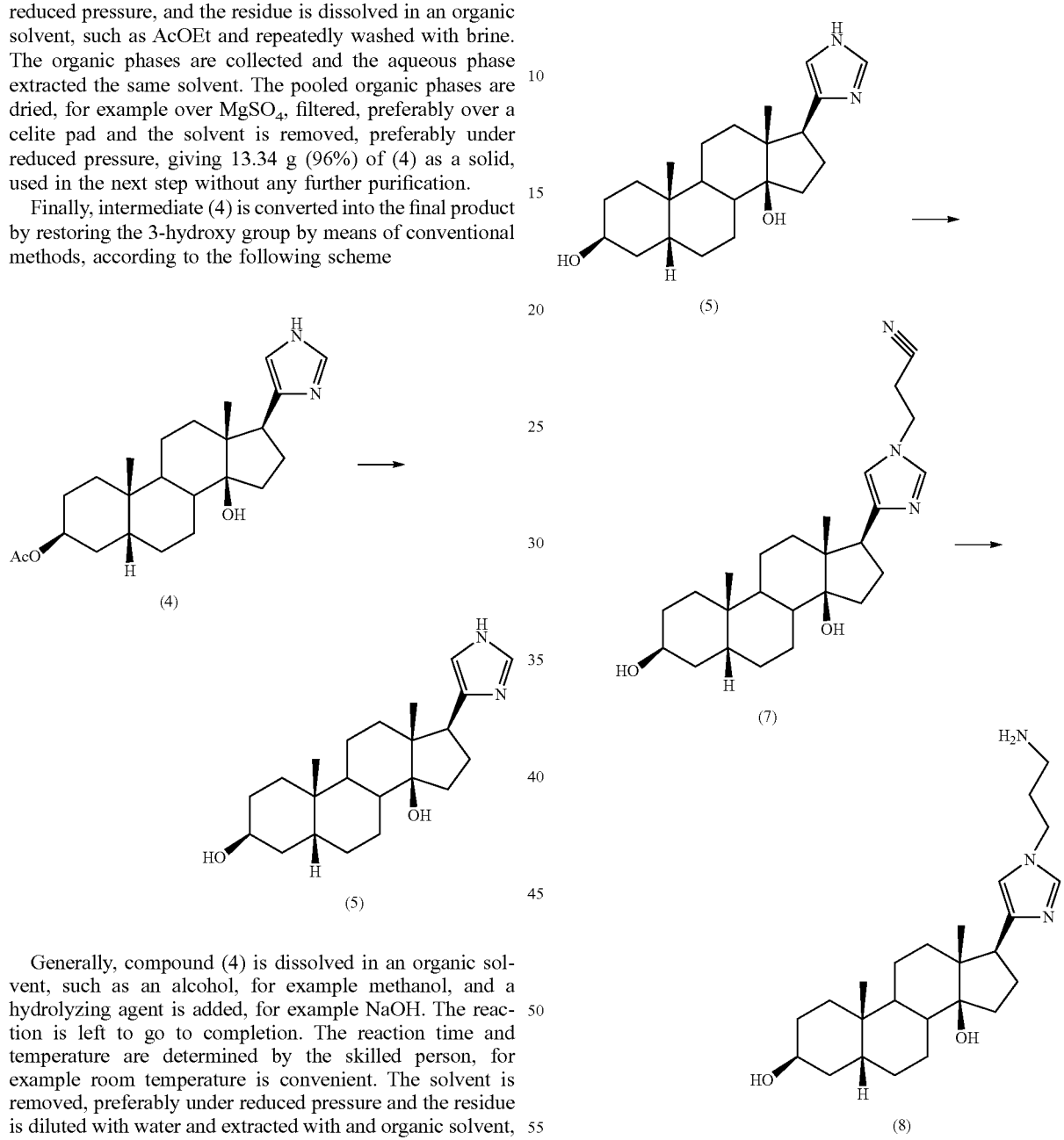

Generally, compound (4) is dissolved in an organic solvent, such as an alcohol, for example methanol, and a hydrolyzing agent is added, for example NaOH. The reaction is left to go to completion. The reaction time and temperature are determined by the skilled person, for example room temperature is convenient. The solvent is removed, preferably under reduced pressure and the residue is diluted with water and extracted with and organic solvent, such as dichloromethane. The organic phase is dried, for example over MgSO$_4$, filtered and the solvent removed, preferably under vacuum giving the final product (5). If wished, the final compound can be converted with conventional methods in a pharmaceutically acceptable salt.

By way of example, for compounds of formula (I) wherein X is NH, Y is CH and Z is N, namely, the heterocycle is imidazolyl substituted with amino (C$_1$-C$_4$) alkyl, compound (3) is transformed into the relevant intermediate (4) according to the scheme described above, but selecting the suitable reactant instead of formamide and modifying reaction conditions accordingly, as well-known by the skilled person. In case the final compound of formula (I) bears the amino (C$_1$-C$_4$) alkyl group on the 1-N nitrogen of the imidazolyl residue, compound (5) is treated according to the following scheme, herein shown for the exemplary case of N-(3-aminopropyl) derivative:

Compound (5) is dissolved into a suitable organic solvent, for example dimethylsulfoxide (DMSO), in the presence of a strong base, for example K$_2$CO$_3$. Acrylonitrile is added and the reaction is carried out at a suitable temperature, for example room temperature, for a time sufficient to reaction completion. The skilled person can easily select the appropriate ε-unsaturated nitrile depending on the length of the alkyl chain. At reaction completion, water is added and the mixture is extracted with a suitable organic solvent, for example Ethyl Acetate, the organic phase is dried as usual, for example over Na$_2$SO$_4$, filtered and the solvent removed, preferably under reduced pressure, giving intermediate (7), used in the next step without any further purification. Finally, the nitrile group is reduced to amino group according to well-known methods. For example, product (7) is dissolved in an organic solvent, for example tetrahydrofuran (THF), preferably the solvent is anhydrous. A reducing agent, such as LiAlH$_4$ is added and the mixture is heated, preferably refluxed for a time sufficient to reaction completion. Subsequently, the cooled solution is diluted with the same reaction solvent, or other convenient solvent and water and a solution of a base, such as NaOH, is added to precipitate a solid. The solid is isolated, for example by filtration and washed with a solvent, and the solid product isolated is purified according to conventional methods, for example through flash chromatography (SiO$_2$) eluting with a suitable eluent system, for example CHCl$_3$/MeOH/NH$_3$ 9/1/0.1 giving product (8).

By way of example, for compounds of formula (I) wherein X is CH, Y is NH and Z is N, namely, the heterocycle is pyrazolyl, compound (I) is transformed into intermediate (V) according to the following scheme.

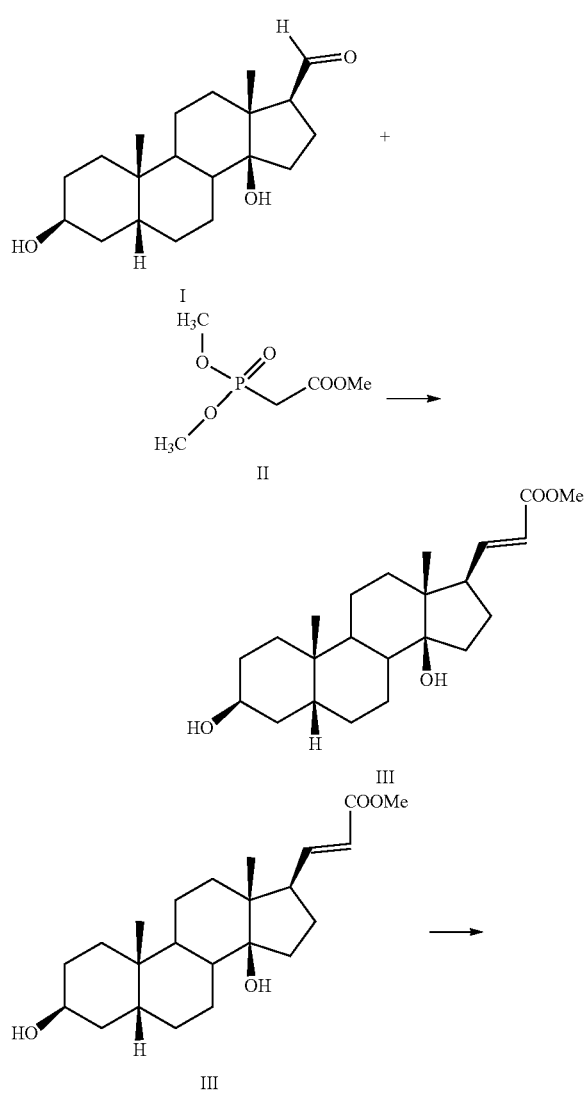

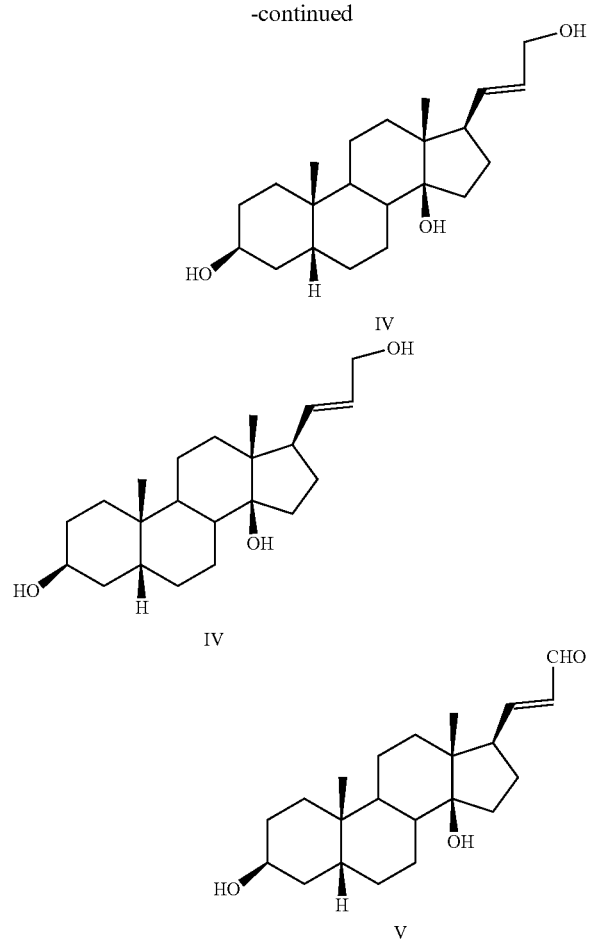

Aldehyde (I) is well-known and its preparation is disclosed in Gobbini et al. Synth Comm, 27(6), 1115-1122 (1997).

Aldehyde (I) is transformed into the derivative (III) according to well-known methods. For example, to a suspension of NaH (typically 55% dispersed in mineral oil) in an anhydrous solvent, such as THF, Trimethyl Phosphonoacetate (II) is added dropwise, at 0° C., under inert atmosphere. The suspension is left at room temperature for a convenient time, for example 30 minutes, then cooled at 0° C. Aldehyde (I), dissolved in a dry organic solvent, preferably the same solvent of the previous mixture, is added and the mixture left to reaction completion, for example at room temperature. An organic solvent is subsequently added, for example EtOAc, the mixture transferred into a solution of NaH$_2$PO$_4$ (typically 5% in water) and extracted with the same solvent. The pooled organic phases are concentrated to dryness, preferably under reduced pressure. The solid residue is suspended in water and kept under stirring for some time, filtered and dissolved in organic solvent, for example AcOEt and dichloromethane, then dried as usual, filtered and the solvent removed, preferably under reduced pressure, giving intermediate (III), used in the next step of reduction of the ester into alcohol without any further purification. Reduction of esters to alcohols is well known and many methods are available to the skilled person. For example, to a solution of compound (III) in dry organic solvent, for example THF, under inert atmosphere, at −78° C., neat diisobutylaluminium hydride (DIBAH) is added and the reaction is brought to completion. After cooling at −78° C., a mild acidic solution (typically citric acid 13% in water) is added and reacted for a sufficient time, then additional neutral inorganic salt for facilitating the separation of the phases, for example NaCl, is added and the aqueous phase is washed with an organic solvent, such as EtOAc. The pooled organic phases are washed with a mild basic aqueous solution, such as for example a solution of NaHCO₃ (for example 5%), dried as usual, filtered and the solvent removed, preferably under reduced pressure, giving intermediate (IV), used in the next step without any further purification. The next step is a conventional oxidation of an alcohol to aldehyde. For example, to a solution of compound (IV) in a suitable organic solvent, such as dioxane, MnO₂ is added and the suspension stirred for a sufficient time, typically at room temperature. The mixture is filtered to eliminate metals, for example on a celite pad, that is washed with an organic solvent, such as AcOEt. The solvents are removed, preferably under reduced pressure, and the residue can be crystallized with a suitable crystallization medium, for example Diethyl Ether to give compound (V).

As subsequently disclosed, intermediate (V) can be used as starting compound to prepare compound of formula (I) with a variety of heterocycle residues.

For the preparation of compound of formula (I), wherein pyrazol is the heterocycle, the following reaction scheme can be followed.

To a solution of compound (V) in a suitable reaction medium, for example Acetic Acid, p-Toluenesulfonyl hydrazide is added. The reaction mixture is left for a sufficient time at a suitable temperature, for example room temperature, then it is diluted with a solution of Na₂HPO₄ (typically 5% in water). The suspension is filtered, the solid dried, preferably under reduced pressure, and solubilised in a solvent, for example dimethylformamide (DMF), adding a sterically hindered strong base, such as potassium tert-butoxide. The reaction is brought to completion, for example starting from room temperature, then heating, for example to 80° C., then poured in water and extracted with a suitable solvent, for example Diethyl ether. The pooled organic phases are dried as usual, filtered and the solvent removed, preferably under reduced pressure. The residue is purified by conventional methods, for example flash-chromatography (SiO₂) with a suitable eluent system (for example CH₂Cl₂/Acetone 7/3/as eluent) to give the final product.

The same compound (V) can be used for obtaining other heterocycle systems, for example, compounds of formula (I) wherein the heterocycle is isoxazole, namely wherein X is CH, in particular CH substituted with an amino (C₁-C₄) alkyl, Y is O and Z is N. An exemplary method is provided herein according to the following scheme:

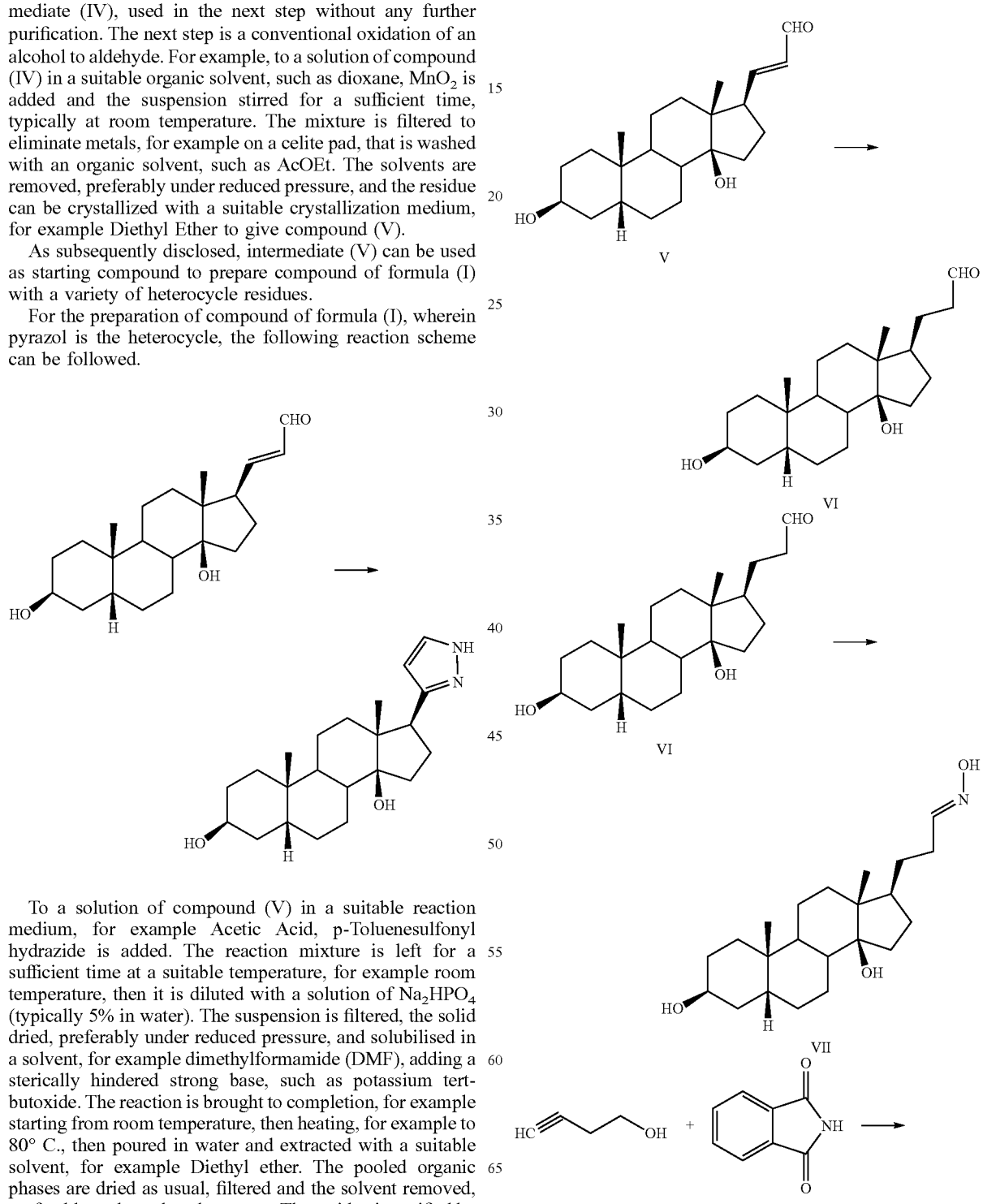

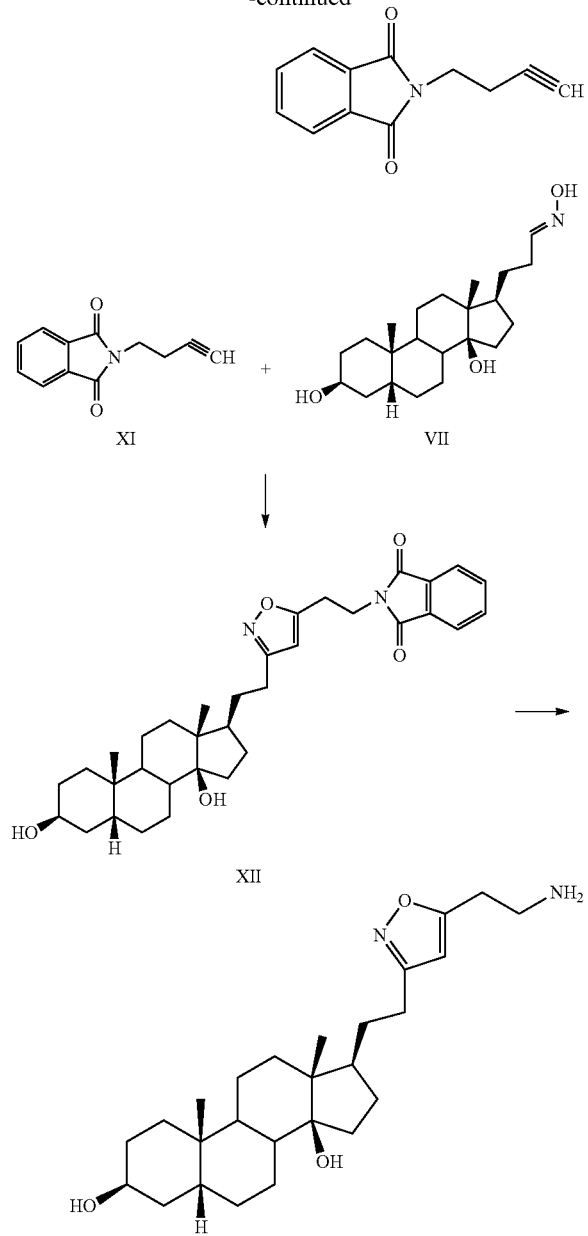

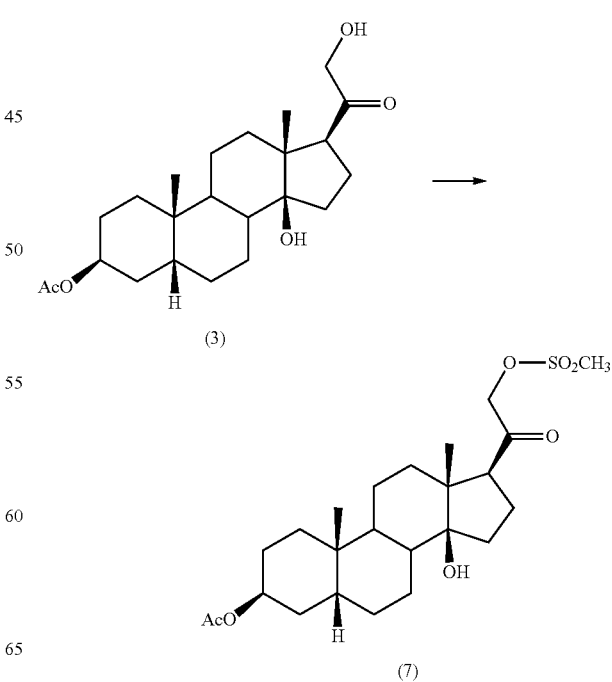

Compound (V) is submitted to a double bond hydrogenation according to conventional methods. For example, to a solution of product (V) in a suitable reaction medium, for example EtOAc, a hydrogenation catalyst, for example Pd/C (5%), is added and the mixture is kept under hydrogen, typically at atmospheric pressure and room temperature, for a sufficient time. After reaction completion, the catalyst is filtered off, for example on a celite pad and the filtrate concentrated to dryness, preferably under reduced pressure, obtaining product (VI). Aldehyde (VI) is then converted into oxime (VII) according to conventional methods. For example, to a solution of compound (VI) in a reaction medium, for example dioxane, hydroxylamine hydrochloride and NaOH are added. The reaction is brought to completion, it can be done at room temperature, the solvent removed, preferably under reduced pressure and extracted with a solvent, for example CHCl$_3$. The organic phase is concentrated to dryness, preferably under reduced pressure, giving product (VII).

Alkyne (XI) is prepared according to the desired length of the alkyl chain, as provided in formula (I). In the exemplary embodiment shown in the above scheme, where the alkyne has two methylene groups, to a solution of 3-butyn-1-ol in a dry solvent, such as THF, PPh$_3$ and Phthalimide, at 0° C., are added. 1,2-Ethoxycarbonyl diazene solution (DEAD) is added to the previous solution and the mixture is left until reaction completion, then the solvent is removed, preferably under reduced pressure, and the residue purified by conventional methods, for example by flash-chromatography (SiO$_2$) in a suitable eluent (for example Heptane/diethyl ether 9/1) to give product (XI). Alkyne (XI) is reacted with oxime (VII). To a suspension of (VII) in organic solvent, for example chloroform containing 0.5% of pyridine, N-Chlorosuccinimide is added and the reaction is carried out in inert (N$_2$) atmosphere. A solution of alkyne (XI) in organic solvent, for example chloroform containing trimethylamine (TEA), is added and the reaction is brought to its end, for example at room temperature, diluted with organic solvent, preferably the same solvent and washed with water. The solvent is removed to dryness, preferably under reduced pressure, and the residue is purified by conventional methods, for example flash-chromatography (SiO$_2$) in suitable eluent system (for example Cyclohexane/Acetone/Chloroform 7/2/2) to give product (XII). Finally, the end desired product is obtained treating compound (XII) with Hydrazine hydrochloride in a solvent, for example ethanol, preferably under reflux till reaction completion. The mixture is diluted with water, solvent is removed, preferably under reduced pressure, and the residual aqueous part is extracted with organic solvent, for example CH$_2$Cl$_2$. The organic phase is brought to dryness, preferably under reduced pressure, and the residue is purified by conventional methods, for example flash-chromatography (SiO$_2$) (exemplary diluent CHCl$_3$/MeOH/NH$_3$ 95/5/0.5) to give final product.

In the exemplary embodiment of compounds of formula (I) where a guanidine group is present, the following scheme can be followed, starting from intermediate (3).

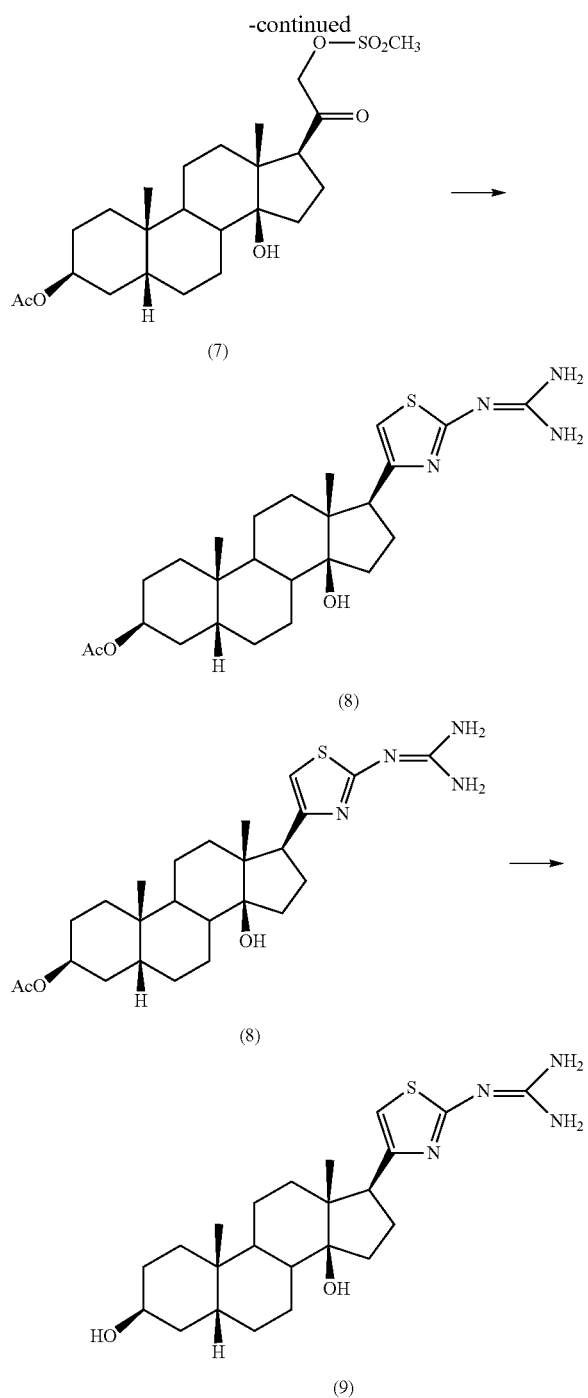

To a solution of product (3) in anhydrous solvent, for example dichlorometane, triethylamine or equivalent agent is added. The solution is cooled, for example at 5° C., and Methanesulfonyl chloride, or another known leaving group is added and the solution kept at the same cooling temperature for sufficient time, then at room temperature for additional time to reaction completion. The solution is diluted with the solvent and washed with a solution of NaHCO$_3$ or equivalent. The aqueous phase is extracted with organic solvent, for example dichloromethane, and the pooled organic phases washed with water. The aqueous phase is extracted again with extraction solvent and the pooled organic phases dried as usual, the solvent removed, preferably under reduced pressure, giving intermediate (7), used in the next step without any further purification. To an organic solution of intermediate (7), for example Acetone, 2-Imino-4-thiobiuret is added. The reaction is carried out, preferably under reflux, till reaction completion, checked by conventional methods, such as thin layer chromatography (TLC). After cooling down at room temperature, the reaction is left to stand for additional time, checking reaction completion. The solid is filtered off and the solvent removed, preferably under reduced pressure. The solid residue is taken-up with organic solvent, for example dichloromethane, and water. The aqueous phase is extracted, the solvent and the pooled organic phases are dried as usual, filtered and the solvent removed, preferably under vacuum, giving intermediate (8), that is purified by conventional methods, for example flash-chromatography (SiO$_2$) (exemplary eluent cyclohexane/ ethyl acetate 1/1+1% of TEA—ethyl acetate 99%+1% of TEA) to give product (8). NaOH or equivalent agent is added to a solution of (8) in a solvent, such as for example MeOH. The reaction is carried out, preferably at room temperature then the solvent is removed. The residue is washed with water and filtered. The solid on the filter is further washed with additional water, then purified by crystallization with a suitable crystallization medium, for example EtOH/water. The solid is dissolved in organic solvent, for example EtOH, typically at room temperature and water is added, the mixture is left to recrystallize. The solid is recovered by filtration yielding product (9).

For compound of formula (I) wherein R is beta-OH, the above described synthetic schemes are carried out starting from digoxygenin instead of digitoxigenin. In this case, the initial reaction for hydroxyl protection of OH is done for positions 3- and 12-.

The compounds of formula (I) can be prepared resorting to the common general knowledge of those skilled in organic synthesis. All the starting product, reactants, reaction media, catalysts and any other material are commercially available or can be prepared according to methods described in literature. Knowledge sources are well-known and comprise scientific literature, textbooks, manuals, databases and service providers (e.g., the Chemical Abstract Service, a division of the American Chemical Society).

Alternative synthesis can be used for the preparation of the compounds of formula (I). The reactions herein disclosed can be varied, modified in their reactants, materials and conditions, as well as the methods for isolating and purifying the end products. Reaction times and temperatures can be selected by the skilled person according to his or her experience and general knowledge. If desired, Good Laboratory Practice (GLP) and Good Manufacturing Practice (GMP) can be adopted according to the requirements of purity so desired. Materials are preferably of purity, high purity or pharmaceutical grade. Analytical methods are those conventionally used in organic chemistry, such as for example chromatography, spectroscopy and any other suitable technique.

Pharmaceutical Compositions

Pharmaceutical compositions and formulations comprise one or more of the herein disclosed compounds of formula (I) in admixture with at least one conventional pharmaceutically acceptable carrier and/or vehicle and/or excipient.

The pharmaceutical compositions can be administered parenterally, topically, subcutaneously, intramuscularly, orally or by local administration, such as by aerosol or transdermally. Enteral, in particular orally administrable, pharmaceutical compositions are preferred.

The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Mack Publishing Co, Easton Pa. ("Remington's").

The compounds of formula (I) as therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, buffers, preservatives and antioxidants can also be present in the compositions.

Formulations of the compositions according to the present invention include those suitable for oral/nasal, sublingual, topical, parenteral—for example by intramuscular or intravenous injection—rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient which can be combined with a carrier material to produce a single dosage form will generally be that amount of the compound which produces a therapeutic effect.

Pharmaceutical formulations as provided herein can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations used to practice the uses and methods as provided herein can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition used to practice the uses and methods as provided herein) in admixture with excipients suitable for the manufacture of aqueous suspensions. Such excipients include a suspending agent, such as sodium carboxymethylcellulose, methylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin, or erythritol or rebaudioside A. Formulations can be adjusted for osmolarity.

Oil-based pharmaceuticals are particularly useful for administration hydrophobic active agents used to practice the uses and methods as provided herein. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose, or erythritol or rebaudioside A. These formulations can be preserved by the addition of an antioxidant such as ascorbic acid. As an example of an injectable oil vehicle, see Minto (1997) J. Pharmacol. Exp. Ther. 281:93-102. The pharmaceutical formulations as provided herein can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

According to the present invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

According to the present invention, the pharmaceutical compounds can be delivered by transdermally, by a topical route, formulated as applicator sticks, solutions, suspensions, emulsions, gels, creams, ointments, pastes, jellies, paints, powders, and aerosols.

According to the present invention, the pharmaceutical compounds of formula (I) can be delivered by inhalation; for example, in alternative embodiments the compounds of formula (I) for inhalation are prepared for dry dispersal, for example, by spray drying a solution containing the active ingredient, i.e. the compound of formula (I), e.g., using methods as described in U.S. Pat. Nos. 6,509,006; 6,592,904; 7,097,827; and 6,358,530. Exemplary dry powder excipients include a low molecular weight carbohydrates or polypeptides to be mixed with the compound of formula (I) to aid in dispersal. In alternative embodiments, types of pharmaceutical excipients that are useful as carriers for dry powder dispersal include stabilizers such as human serum albumin (HSA), that is also a useful dispersing agent, bulking agents such as carbohydrates, amino acids and polypeptides; pH adjusters or buffers; salts such as sodium chloride; and the like. These carriers may be in a crystalline or amorphous form or may be a mixture of the two. Devices that can be used to deliver powder or aerosol formulations include those as described e.g., in U.S. Pat. Nos. 5,605,674; 7,097,827.

According to the present invention, the pharmaceutical compounds can also be delivered as nanoparticles or microspheres for slow release in the body. For example, nanoparticles or microspheres can be administered via intradermal or subcutaneous injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

According to the present invention, the pharmaceutical compounds of formula (I) can be parenterally administered, such as by intramuscular (IM) or intravenous (IV) administration or administration into a body cavity or lumen of an organ. These formulations can comprise a solution of active agent dissolved in a pharmaceutically acceptable carrier. Acceptable vehicles and solvents that can be employed are water, dextrose in water, and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations as provided herein can be lyophilized. Provided are a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. There are many other conventional lyophilizing agents. Among the sugars, lactose is the most common. Also used are citric acid, sodium carbonate, EDTA, Benzyl alcohol, glycine, sodium chloride, etc. (see for example Journal of Excipients and Food Chemistry Vol. 1, Issue 1 (2010) pp 41-54; U.S. patent app. no. 20040028670).

According to the present invention, the compounds of formula (I) as provided herein can be administered for prophylactic and/or therapeutic treatments. In therapeutic applications, compositions are administered to a subject already suffering from a condition, or disease in an amount sufficient to cure, alleviate or partially arrest the clinical manifestations of the condition, or disease and its complications (a "therapeutically effective amount"). For example, in alternative embodiments, pharmaceutical compositions as provided herein are administered in an amount sufficient to treat, prevent or ameliorate in an individual in need thereof. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur.

J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regimen, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions used to practice the methods and uses as provided herein can be in a daily amount of between about 1 to about 20, 50, 100 or 1000 or more microgram per kilogram of body weight per day or an equivalent of a pharmaceutically acceptable salt, solvate or hydrate thereof.

In alternative embodiments, an effective amount of a compound of formula (I) or an equivalent of a pharmaceutically acceptable salt, solvate or hydrate thereof, administered to an individual in need thereof comprises use of various dosaging schedules, e.g.: A) in case of AHFS, to rescue hospitalized patient, a compound of formula (I) can be administered by intravenous infusion over 24/48 h at doses ranging from 0.1 to 0.5 to about 10, 50 or 100 or more microgram per kg of body weight per minute. B) in patients rescued from AHFS and discharged from the hospital, the dosage schedule for the maintenance of the therapeutic effect can be in the daily amount of between 1, 10, 50 or 100 or 1000 or more microgram per kg of body weight. Oral administration is a preferred embodiment.

In alternative embodiments, an effective amount of a compound of formula (I) or an equivalent of a pharmaceutically acceptable salt, solvate or hydrate thereof, administered to an individual in need thereof is individualized based on monitoring of Pulmonary Capillary Wedge Pressure (PCWP), dyspnea, peripheral and pulmonary venous congestion, urinary volume, exercise capacity, serum biomarkers such as NT-proBNP and high sensitive cardiac Troponin (hs-cTnT).

In alternative embodiments, a compound of formula (I) or an equivalent of a pharmaceutically acceptable salt, solvate or hydrate thereof, administered to an individual in need thereof is an amount sufficient to maintain normal exercise tolerance without breathlessness.

In alternative embodiments, an effective amount is demonstrated by reduction of PCWP, orthopnea, paroxysmal nocturnal dyspnea, increase of exercise tolerance, reduction of peripheral and pulmonary venous congestion, such as pulmonary crepitations or rales, reduction of ankle swelling, reduction of biomarkers urinary output such as NT-proBNP and high sensitive cardiac Troponin (hs-cTnT).

In alternative embodiments, lower dosages of a compound of formula (I) or an equivalent of a pharmaceutically acceptable salt, solvate or hydrate thereof, are used when administered in the blood stream or IV or IM (in contrast to administration e.g., orally, by inhalation or subcutaneously) e.g., as an IV or an IM administration, or into a body cavity or into a lumen of an organ. Substantially higher dosages can be used in topical, spray, inhalation or oral administration or administering by powders, spray or inhalation. Actual methods for preparing parenterally or non-parenterally administrable formulations will be known or apparent to those skilled in the art and are described in more detail in such publications as Remington's, supra.

In alternative advantageous embodiments, a compound of formula (I) or an equivalent of a pharmaceutically acceptable salt, solvate or hydrate thereof, are given chronically, e.g., from day of diagnosis and until the last day of a patient's life or until the disease has abated. In alternative embodiments, dose adjustments are required moving from a treatment phase to a maintenance period through the periodic monitoring of specific, conventionally known biomarkers or clinical signs of the disease.

In alternative embodiments, in evaluating the efficacy of a treatment, a treatment regimen or a particular dosage, or to determine if a treatment versus a maintenance dosage should be given, individuals, e.g., patients affected by acute or chronic heart failure, are subject to regular periodic screening for the presence and extent of organ and tissue involvement or damage, e.g., heart (ventricle dilatation, third heart sound cardiac hypertrophy), fatigue, tiredness, reduced exercise tolerance, increased time to recover after exercise, kidney (renal insufficiency, oliguria), lung (orthopnea, paroxysmal nocturnal dyspnea, tachypnea), ankle swelling, elevated jugular venous pressure. A thorough physical examination should be done at a time interval chosen by those experts in the treatment of a cardiovascular disease, in particular acute or chronic heart failure which would concentrate on cardiac, pulmonary and peripheral circulation functions. Accordingly, in alternative embodiments, therapy with a compound of formula (I) or an equivalent of a pharmaceutically acceptable salt, solvate or hydrate thereof, is instituted as early as possible, preferably in emergency, to prevent the rapid evolution of symptoms and continued after patient's discharge for years, preferably during the whole life of the patient or at least a period consistent with the way other drugs are used in heart failure.

According to the present invention, uses and methods as provided herein can further comprise co-administration with other drugs or pharmaceuticals. In fact, the present invention selectively corrects a depressed cardiac biochemical function (namely the SERCA2a activity). This certainly contributes to relieving the existing HF clinical symptoms, with less unwanted side effects than those of the available therapies (just because the selectivity mentioned above). However, as CHF and AHF are complex clinical syndromes the present invention is potentially associable to existing and future drug classes and/or specific drugs such as: a) drug classes such as, ACE inhibitors, AIRBs, diuretics, Ca channel blockers, p blockers, digitalis, NO donors, vasodilators, SERCA2a stimulators, neprilisin (NEP) inhibitors, myosin filament activators, recombinant relaxin-2 mediators, recombinant NP protein, activators of the soluble Guanylate Cyclase (sGC), beta-arrestin ligand of Angiotensin II receptor; b) specific drugs: hydrochlorothyzide, furosemide, verapamil, diltiazem, carvedilol, metoprolol, hydralazine, eplerenone, spironolactone, lisinopril, ramipril, nitroglycerin, nitrates, digoxin, valsartan, olmesartan, telmisartan, candesartan, losartan, entresto, omecamtiv, sacubitril, serelaxin, ularitide, levosimendan, cinaciguat.

The compounds of the present invention, as used a therapeutic agents, in particular for treating heart failure, can be combined with other therapeutic agents used in the treatment of the same disease. Exemplary other therapeutic agents are diuretics, for example furosemide, bumetanide, and torasemide. Metolazone, an aldosterone antagonist, such as spironolactone or eplerenone; thiazide diuretics, such as Hydrochlorothiazide, metolazone, and chlorthalidone. Other agents are ACE inhibitors, for example Lisinopril and Ramipril. Also Angiotensin II receptor blockers (ARBs), such as valsartan, candesartan and losartan can be taken into consideration. Angiotensin receptor/neprilysin inhibitor (ARNI), sacubitril for example, are comprised. Other agents can be selected from Beta-blockers, such as carvedilol and metoprolol for example, or Vasodilators, for example Hydralazine, optionally combined with isosorbide dinitrate, Nitrates, as nitroglycerin, amlodipine and felodipine; non-dihydropyridines such as diltiazem or verapamil. The compounds of the present invention can also be combined with Digoxin, if needed. Other drugs, as Ivabradine and other Anticoagulant may be considered.

The compounds of the present invention can be combined with other therapeutic agents, in particular agents useful for treating cardiovascular diseases, more in particular in the combination therapy of heart failure. The combined active ingredients can be administered according to different protocols, decided by the medical doctor. According to an embodiment of the present invention, combination therapy can be carried out by administering the compounds of formula (I) both at the same time or at different time of the further therapeutically active ingredient or ingredients. In case of concomitant administration, the compound of the present invention and the further active ingredient or ingredients can be each formulated in a respective pharmaceutical composition or in the same unitary dosage form. In the former case, the present invention provides a kit, in particular for the treatment of heart failure, comprising separate pharmaceutical compositions containing the compound of the present invention and the further active ingredient or ingredients, respectively. In another embodiment, the present invention provides a pharmaceutical unit dosage form kit, in particular for the treatment of heart failure, comprising compound of the present invention and the further active ingredient or ingredients in the same unit dosage form. Combination therapy according to the present invention provides advantageous treatment of heart failure due to the inotropic-lusitropic effect of the compounds of formula (I) herein disclosed in addition to or synergically combined with the well-known therapeutic effect of the additional active agents herein disclosed.

Also provided are nanoparticles, nanolipoparticles, vesicles and liposomal membranes comprising compounds used to practice the uses and methods as provided herein, e.g., to deliver pharmaceutically active compounds and compositions as provided herein (a compound of formula (I) or an equivalent of a pharmaceutically acceptable salt, solvate or hydrate thereof, optionally combined with a further therapeutically active agent as disclosed above) to a subject in need thereof. In alternative embodiments, these compositions are designed to target specific molecules, including biologic molecules, such as polypeptides, including cell surface polypeptides, e.g., for targeting a desired cell type, e.g., a myocyte or heart cell, an endothelial cell, and the like.

Provided are multilayered liposomes comprising compounds used to practice methods as provided herein, e.g., as described in Park, et al., U.S. application No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice uses and methods as provided herein.

Liposomes can be made using any method, e.g., as described in U.S. Pat. No. 4,534,899; or Park, et al., U.S. application No. 20070042031, including method of producing a liposome by encapsulating an active agent according to the present invention (or a combination of active agents), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice uses and methods as provided herein comprise a substituted ammonium and/or polyanions, e.g., for targeting delivery of a compound a compound of formula (I) or an equivalent of a pharmaceutically acceptable salt, solvate or hydrate thereof used to practice methods as provided herein to a desired cell type, as described e.g., in U.S. application No. 20070110798.

Provided are nanoparticles comprising compounds according to the present invention used to practice uses and methods as provided herein in the form of active agent-containing nanoparticles (e.g., a secondary nanoparticle), as described, e.g., in U.S. application No. 20070077286. In one embodiment, provided are nanoparticles comprising a fat-soluble active agent used to practice a use and method as provided herein or a fat-solubilized water-soluble active agent to act with a bivalent or trivalent metal salt.

In one embodiment, solid lipid suspensions can be used to formulate and to deliver compositions used to practice uses and methods as provided herein to mammalian cells in vivo, in vitro or ex vivo, as described, e.g., in U.S. application No. 20050136121.

The compositions and formulations used to practice the uses and methods as provided herein can be delivered by the use of liposomes or nanoliposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

Delivery Vehicles

In alternative embodiments, any delivery vehicle can be used to practice the uses and methods as provided herein, e.g., to deliver the compounds provided herein to a subject in need thereof. For example, delivery vehicles comprising polycations, cationic polymers and/or cationic peptides, such as polyethyleneimine derivatives, can be used e.g. as described, e.g., in U.S. application No. 20060083737.

In one embodiment, a dried polypeptide-surfactant complex is used to formulate a composition used to practice a use and method as provided herein, e.g. as described, e.g., in U.S. application No. 20040151766.

In one embodiment, a composition used to practice uses and methods as provided herein can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to polyphosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

The following examples further illustrate the present invention.

Preparation of the Compounds of Formula (I)

In the following examples, chemical compounds, solvents, reactants and any other material are from commercial sources, except where otherwise stated.

Example 1

3β-hydroxy-5β-10β-methyl-13β-methyl-14β-hydroxy-17β-(imidazol-4-yl)androstane (CVie 101)

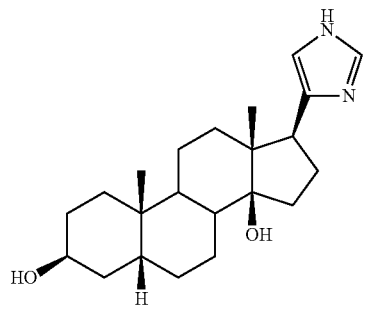 [SMILES: C[C@]12CC[C@H](O)C[C@H]1CCC1C2CC[C@]2(C)[C@@H](c3c[nH]cn3)CC[C@]12O]

Digitoxigenin to 3-acetyl-digitoxigenin

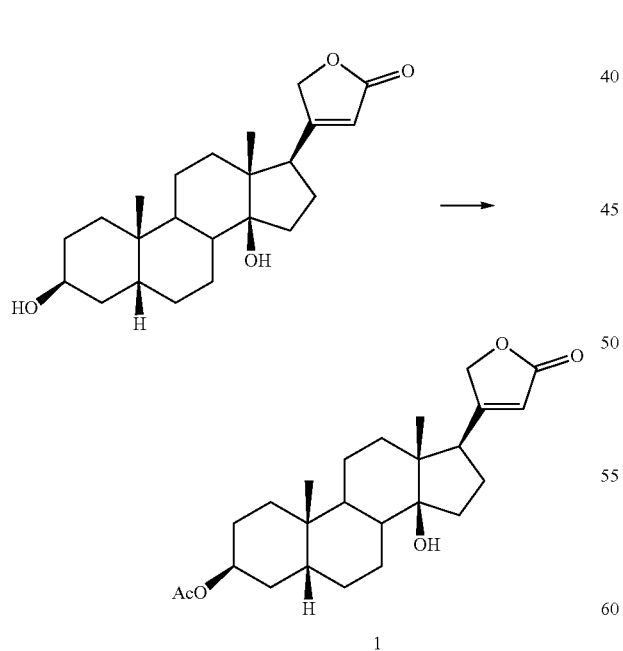

To a solution of 25 grams of digitoxigenin in 118 ml of pyridine under Argon atmosphere, 41 mg of DMAP and 33.1 ml of acetic anhydride were added, maintaining the temperature below 30° C.

After stirring at room temperature for 20 h, the solvent was removed under reduced pressure (co-evaporating with toluene). The residue was taken up with 480 ml of water and stirred at room temperature for 1 h. The resulting solid was collected by filtration, washed with 240 ml of water and dried under vacuum, giving 28.04 g (quantitative yield) of product 1 as pale-yellow solid, used in the next step without any further purification.

3-acetyl-digitoxigenin to Opening 17β-lactone Ring

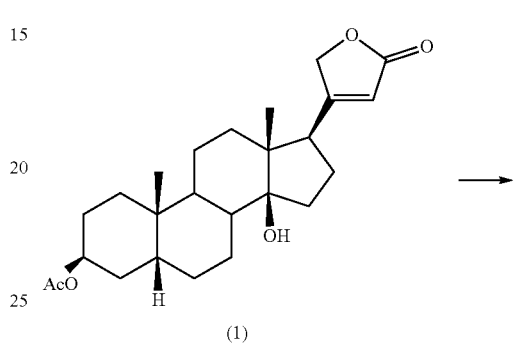

(1)

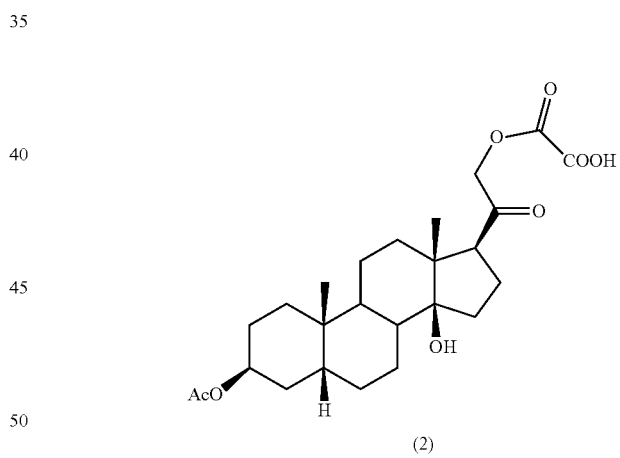

(2)

To a stirred solution of 26.33 g of intermediate 1 in 740 mL of acetone, a solution of 33.8 g of NaIO$_4$ and 105 mg of RuO$_2$ hydrate in 222 ml of water was added. After stirring 30 min at room temperature, a solution of 33.8 g of NaIO$_4$ and 105 mg of RuO$_2$ hydrate in 222 ml of water was added.

32 ml of isopropanol were added and after stirring 15 min at room temperature the solid was filtered off, the volume was reduced under reduced pressure and the residue extracted with AcOEt.

The organic phase was washed with brine, then dried over MgSO$_4$, filtered and the solvent removed under vacuum giving intermediate 2, used in the next step without any further purification.

Reduction to Alcohol

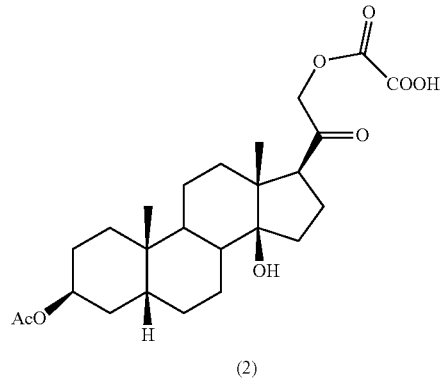
(2)

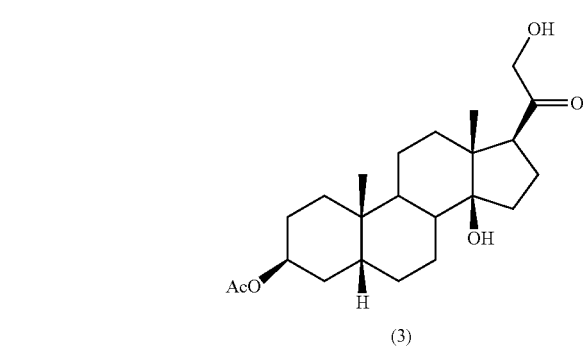
(3)

A solution of 21.47 g of KHCO₃ in 685 ml of water was added to a solution of 28.18 g of intermediate 2 in 1080 ml of MeOH. The solution was kept under stirring at room temperature for 16 h, and 10.74 g of KHCO₃ were added. After 5 h at room temperature, MeOH was removed under reduced pressure, the residue was extracted twice with 500 ml dichloromethane and the organic phase was washed with 250 ml of brine then dried over MgSO₄, filtered and the solvent removed under reduced pressure. The residue was purified trough flash chromatography (SiO2) eluting with 7:3 Cyclohexane/AcOEt, giving 14.78 g (63%) of intermediate 3 as white solid.

Building Imidazole Ring

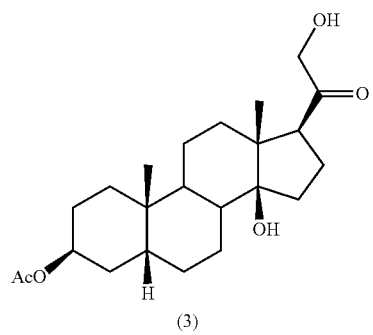
(3)

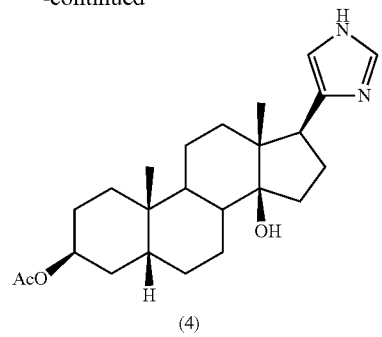
(4)

To a stirred solution of 13.66 g of product 3 in 955 ml of ethanol, 68.3 ml of 37% formaldehyde, a solution of Cu(OAc)₂ (13.27 g in 34 ml of water) and 205 ml of 28% ammonium hydroxide were added. The mixture was heated to reflux for 3 h. The solvent was removed under reduced pressure and the solid residue was dissolved in AcOEt and washed with brine.

The organic phase was collected and the aqueous phase extracted with AcOEt.

The pooled organic phases were dried over MgSO₄, filtered over a celite pad and the solvent was removed under reduced pressure, giving 13.34 g (96%) of 4 as greenish solid, used in the next step without any further purification.

Hydrolysis of 3-acetyl

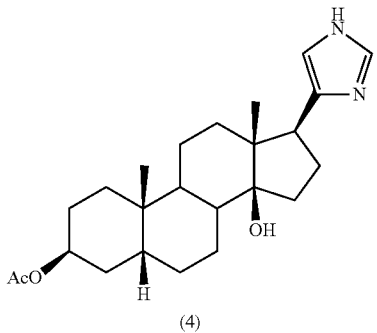
(4)

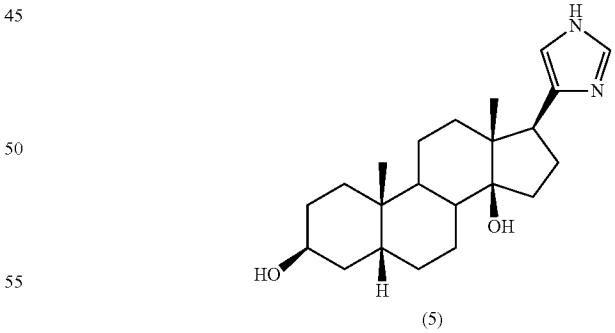
(5)

To a stirred solution of 13.34 g of intermediate 4 in 555 ml of MeOH, 166.5 ml of 1M NaOH were added and the solution was stirred for 16 hours at room temperature. MeOH was removed under reduced pressure and the residue was diluted with water and extracted with dichloromethane.

The organic phase was dried over MgSO₄, filtered and the solvent removed under vacuum giving 8.23 g (69%) of intermediate 5 as off-white solid, used in the next step without any further purification.

Preparation of a Pharmaceutically Acceptable Salt

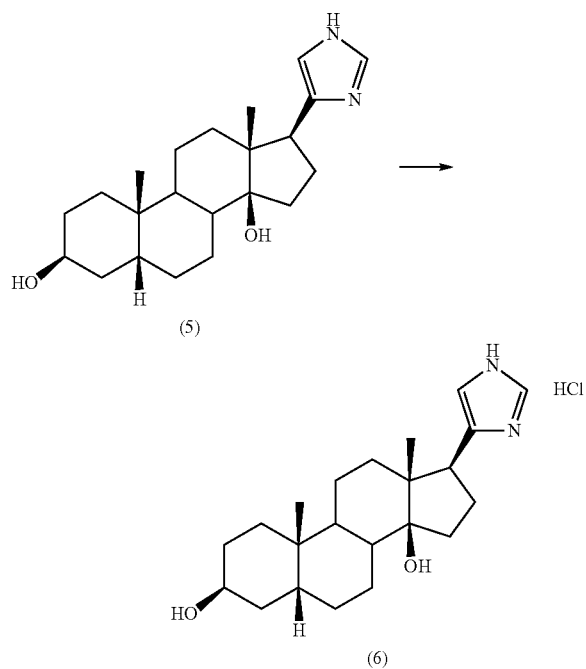

18.1 ml of 1.25M HCl in EtOH were added to a solution of 8.11 g of product 5 in 400 ml of MeOH. The mixture was stirred 5 min at room temperature then the solvent was removed. The residue was solubilised in acetone and heated to reflux, cooled down, then the solid was collected by filtration, giving 6.03 g of white solid that was purified through chromatography.

The solid was purified through multiple semi-preparative C18 column chromatography runs (3.0 g of crude were loaded), eluting with 7:3 water/ACN. Overall yield: 3.95 g (44%).

$^1$H-NMR (d$_6$-DMSO): 0.59 (s, 3H); 0.87 (s, 3H); 1.05-1.24 (m, 4H); 1.32-1.53 (m, 8H); 1.59-1.88 (m, 7H); 2.03-2.11 (m, 1H); 2.21-2.29 (m, 1H); 2.92 (dd, 1H); 3.89 (s, 1H); 4.25 (brs, 1H); 7.29 (d, 1H); 8.86 (d, 1H); 13.72 (s, 1H); 14.22 (s, 1H).

Example 2

3β-hydroxy-5β-10β-methyl-13β-methyl-14β-hydroxy-17β-(2-guanidino-thiazol-4-yl)androstane (Cvie 102)

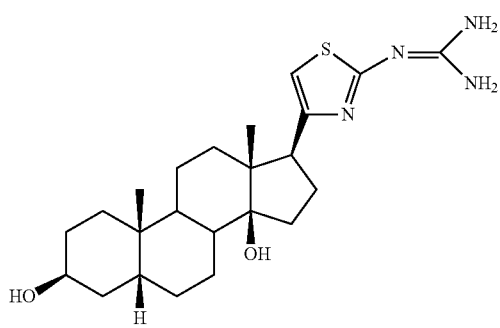 [SMILES: C[C@]12CC[C@H](O)C[C@H]1CCC1C2CC[C@]2(C)[C@@H](c3csc(N=C(N)N)n3)CC[C@]12O]

Digitoxigenin to 3-acetyl-digitoxigenin

To a solution of 25 grams of digitoxigenin in 118 ml of pyridine under Argon atmosphere, 41 mg of DMAP and 33.1 ml of acetic anhydride were added, maintaining the temperature below 30° C.

After stirring at room temperature for 20 h, the solvent was removed under reduced pressure (co-evaporating with toluene). The residue was taken up with 480 ml of water and stirred at room temperature for 1 h. The resulting solid was collected by filtration, washed with 240 ml of water and dried under vacuum, giving 28.04 g (quantitative yield) of product 1 as pale-yellow solid, used in the next step without any further purification.

3-Acetyl-digitoxigenin to Opening 17β-lactone Ring

To a stirred solution of 26.33 g of intermediate 1 in 740 mL of acetone, a solution of 33.8 g of NaIO$_4$ and 105 mg of RuO$_2$ hydrate in 222 ml of water was added. After stirring 30 min at room temperature, a solution of 33.8 g of NaIO$_4$ and 105 mg of RuO$_2$ hydrate in 222 ml of water was added. The mixture was stirred for further 15 min at room temperature, then a solution of 33.8 g of NaIO$_4$ and 105 mg of RuO$_2$ hydrate in 222 ml of water was added.

32 ml of isopropanol were added and after stirring 15 min. at room temperature the solid was filtered off, the volume was reduced under reduced pressure and the residue extracted with AcOEt.

The organic phase was washed with brine, then dried over MgSO$_4$, filtered and the solvent removed under vacuum giving 29.8 g of pale brown solid which was dissolved in 790 ml of acetone.

A solution of 33.8 g of NaIO$_4$ and 105 mg of RuO$_2$ hydrate in 222 ml of water was added. After stirring 30 min at room temperature, a solution of 33.8 g of NaIO$_4$ and 105 mg of RuO$_2$ hydrate in 222 ml of water was added and the mixture stirred 30 min at r.t., then isopropanol (32 ml) was added. A solution of NaIO$_4$ (33.8 g, 158.0 mmol, 2.5 eq) and RuO2 hydrate (105 mg, 0.79 mmol, 2 eq) in water (222 ml) was added and the mixture stirred 30 min at room temperature then 32 ml of isopropanol were added. After stirring 15 min. at room temperature the solid was filtered off, the volume was reduced under reduced pressure and the residue extracted with AcOEt. The organic phase was washed with brine, then dried over MgSO$_4$, filtered and the solvent removed under reduced pressure, giving 28.25 g (97%) of intermediate 2, used in the next step without any further purification.

Reduction to Alcohol

A solution of 21.47 g of KHCO$_3$ in 685 ml of water was added to a solution of 28.18 g of intermediate 2 in 1080 ml of MeOH. The solution was kept under stirring at room temperature for 16 h, and 10.74 g of KHCO$_3$ were added. After 5 h at room temperature, MeOH was removed under reduced pressure, the residue was extracted twice with 500 ml dichloromethane and the organic phase was washed with 250 ml of brine then dried over MgSO$_4$, filtered and the solvent removed under reduced pressure. The residue was purified trough flash chromatography (SiO$_2$) eluting with 7:3 Cyclohexane/AcOEt, giving 14.78 g (63%) of intermediate 3 as white solid.

From Alcohol to Methanesulfonate

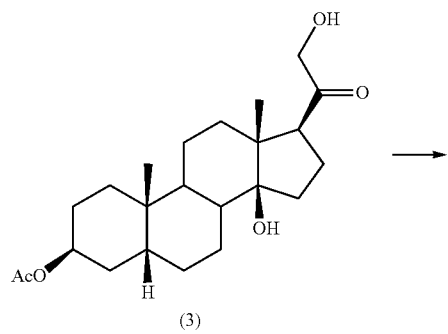
(3)

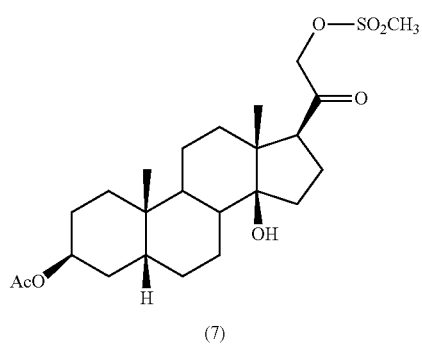
(7)

To a stirred solution of 10.2 grams of product 3 in 205 ml of anhydrous dichlorometane, 5.1 ml of triethylamine were added. The solution was cooled at 5° C. and 2.5 ml of Methanesulfonyl chloride were added dropwise and the solution kept at 5° C. for 10 minutes and at room temperature for additional 2 hours. The solution was diluted with 200 ml of dichloromethane and washed with 200 ml of a solution of NaHCO₃

The aqueous phase was extracted with 50 ml of dichloromethane and the pooled organic phases washed with 200 ml of water. The aqueous phase was extracted again with 50 ml of dichloromethane and the pooled organic phases were dried over MgSO₄, and the solvent was removed under reduced pressure, giving 12.4 g (99%) of 7 as white solid, used in the next step without any further purification.

Building Guanidine-Substituted Thiazole

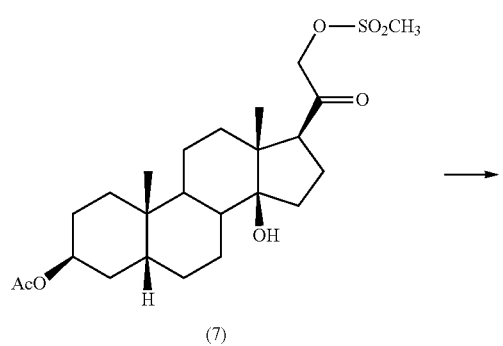
(7)

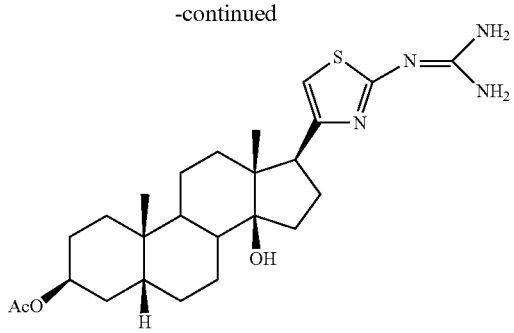

To a stirred solution of 12.4 g of intermediate 7 in 1120 ml of Acetone, 52.3 grams of 2-Imino-4-thiobiuret were added. The solution was refluxed for 5 hours and left to cool down at room temperature and stirred for additional 16 hours. The suspension was filtered the solid discarded and the acetone removed under reduced pressure.

The solid residue was taken-up with 500 ml of dichloromethane and 500 ml of water. The aqueous phase was extracted twice with 250 ml of dichloromethane and the pooled organic phases were dried over MgSO₄, filtered and the solvent removed under vacuum giving 15.3 g of intermediate 8 as yellowish solid, that was purified by flash-chromatography (SiO₂) (from cyclohexane/ethyl acetate 1/1+1% of TEA—ethyl acetate 99%+1% of TEA as eluent) to give 8.95 grams of pure product 8 (73%).

Restoring 3β-hydroxy

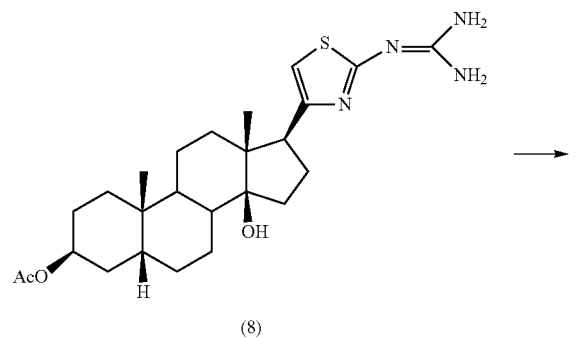
(8)

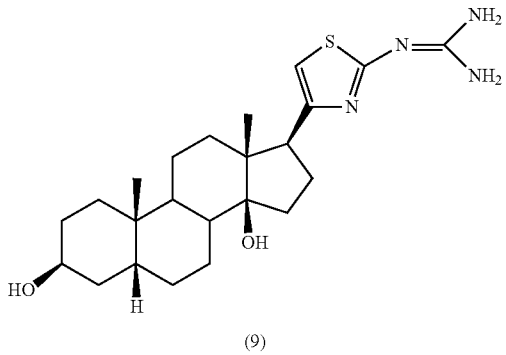
(9)

93.3 ml of NaOH 1M were added to a solution of 8.86 g of intermediate 8 in 900 ml of MeOH. The mixture was stirred 48 hours at room temperature then the solvent was removed. The residue was washed with 250 ml of water and filtered. The solid on the filter further washed with additional 100 ml of water giving 7.7 grams of off-white solid that was purified by crystallization with EtOH/water. The solid was dissolved in 770 ml of EtOH at room temperature and 385 ml of water were added under stirring, the mixture was left at 4° C. for 16 hours. The solid was recovered by filtration yielding 6.24 grams of product 9 as off-white powder.

¹H-NMR (d₆-DMSO, 400 MHz): 0.59 (s, 3H); 0.89 (s, 3H); 1.05-1.24 (m, 4H); 1.32-1.53 (m, 8H); 1.59-1.88 (m, 7H); 2.04-2.09 (m, 2H); 2.72 (t, 1H); 3.90 (s, 1H); 4.20 (s, 1H); 4.89 (s, 1H); 6.59 (bs, 4H).

Preparing a Pharmaceutically Acceptable Salt 5.72 grams of product 9 were dissolved in 230 ml of MeOH, filtered and 4.4 ml of 3M HCl in MeOH were added to the filtered solution. The solvent was removed under reduced pressure, the residue slurred with 130 ml of acetone and stirred for 3 hours at room temperature. After additional 16 hours at 4° C. the solid was recovered by filtration, giving 4.40 grams of white solid Example 3

3β-hydroxy-5β-10β-methyl-12β-hydroxy-13β-methyl-14β-hydroxy-17β-(imidazol-4-yl)androstane (Cvie 104)

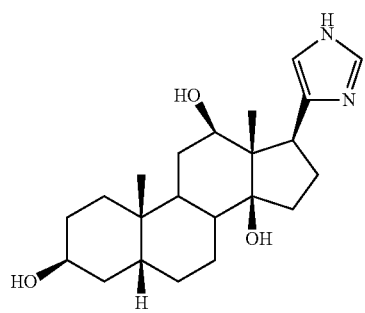 [SMILES: C[C@]12[C@H](O)CC3C(CC[C@@H]4C[C@@H](O)CC[C@]34C)[C@@]1(O)CC[C@@H]2c1c[nH]cn1]

From Digoxin (A) to Digoxigenin

Digoxin (A) ⟶

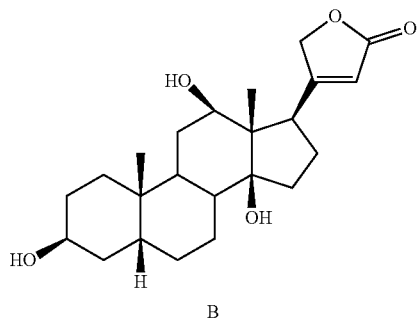

B

To a suspension of 4.33 gram of Digoxin in 43 ml of MeOH, 12.3 ml of 0.2M H₂SO₄ were added and the mixture was heated at reflux for 1 hour and cooled to room temperature. The solvent was removed under reduced pressure and a mixture of 25 ml of ice and water was added to the residue and stirred for 30 minutes. The collected solid was washed, under stirring for 1 hour in 25 ml of cold water, the suspension was filtered and the solid washed on the filter with water, yielding 2.238 grams of white solid B (99%).

Acetylation of 3β,12β-hydroxy Groups

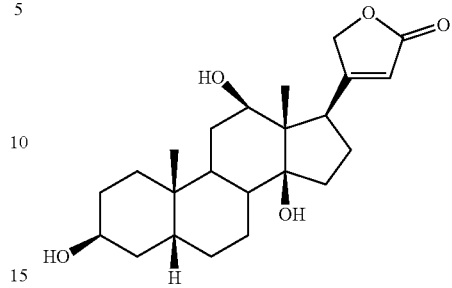

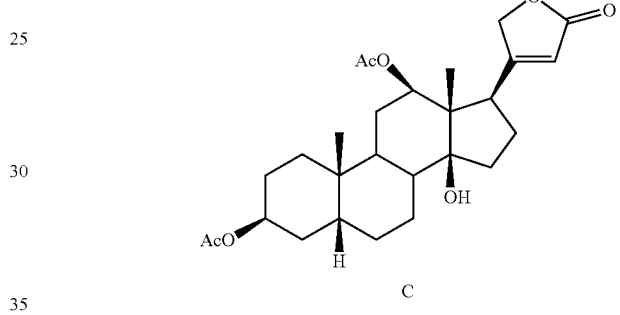

C

To a solution of 2.14 grams of digoxigenin in 10 ml of pyridine under Argon atmosphere, 3 mg of DMAP and 2.5 ml of acetic anhydride were added, maintaining the temperature below 30° C. After stirring at room temperature for 20 h, the solvent was removed under reduced pressure (co-evaporating with toluene). The residue was treated with 25 ml of water and stirred at room temperature for 1 h. The resulting solid was collected by filtration and dried under vacuum, giving 1.92 grams (79%) of product C as white solid, used in the next step without any further purification.

Opening Lactone Ring

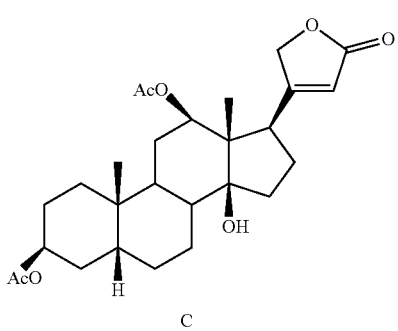

C

-continued

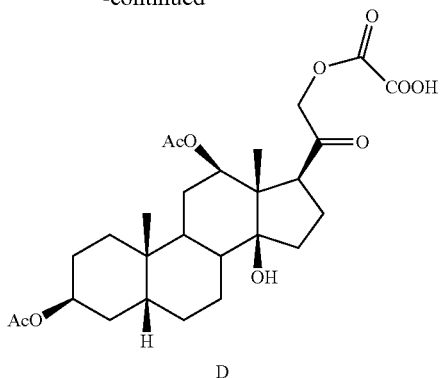

D

To a stirred solution of 1.91 grams of intermediate C in 47 mL of acetone, a solution of 2.15 g of NaIO$_4$ and 7 mg of RuO$_2$ hydrate in 14 ml of water was added. After stirring 30 min at room temperature, a solution of 2.15 g of NaIO$_4$ and 7 mg of RuO$_2$ hydrate in 14 ml of water was added.

2.4 ml of isopropanol were added and after stirring 15 min, at room temperature, the solid was filtered off on a celite pad and washed on the filter with 150 ml of acetone, the solvent was removed under reduced pressure and the residue extracted with AcOEt and water.

The organic phase was washed with brine, then dried over MgSO$_4$, filtered and the solvent removed under vacuum giving 2.25 g (99%) of product D as white solid used in the next step without any further purification.

Hydrolysis of Ester

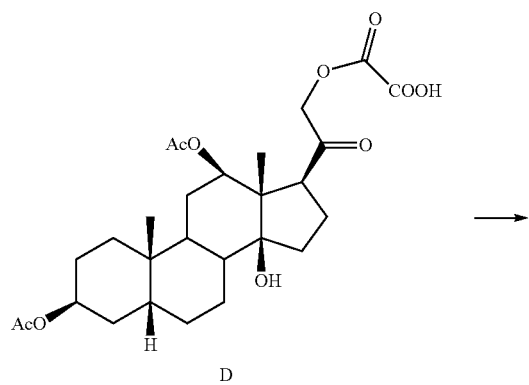

A solution of 1.42 g of KHCO$_3$ in 47 ml of water was added to a solution of 2.25 g of intermediate D in 71 ml of MeOH. The solution was stirred at room temperature for 72 hours, then MeOH was removed under reduced pressure. The remaining aqueous solution was extracted with EtOAc and the organic phase was dried over MgSO$_4$, filtered and the solvent removed under reduced pressure. The crude residue was purified trough SiO$_2$ gel column chromatography eluting with Cyclohexane/AcOEt 6/4, giving 1.03 grams (57%) of intermediate E as white solid.

Building Imidazole Ring

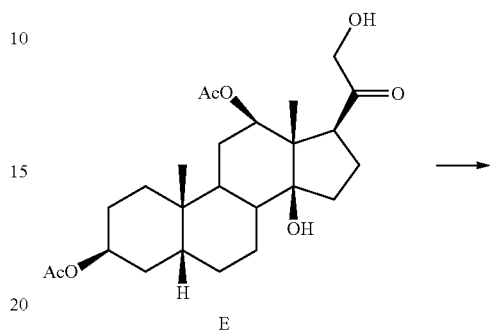

E

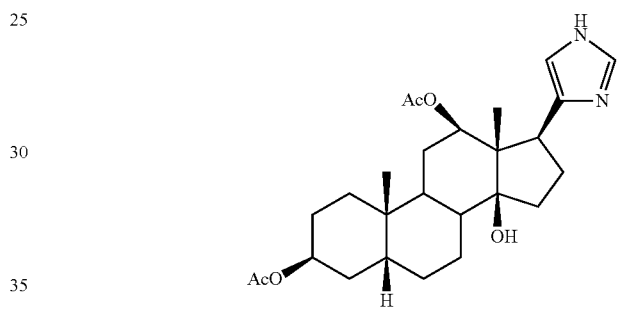

F

To a stirred solution of 500 mg of product E in 30 ml of ethanol, 2.2 ml of 37% formaldehyde, a solution of Cu(OAc)$_2$ (423 g in 2.6 ml of water) and 6.5 ml of 28% ammonium hydroxide were added. The mixture was heated to reflux for 3 h. The volume was reduced and the residue was taken up with brine and AcOEt.

The organic phase was collected and the aqueous phase extracted with AcOEt. The pooled organic phases were died over MgSO$_4$, filtered and the solvent was removed under reduced pressure, giving 474 mg (93%) of F as greenish solid, used in the next step without any further purification.

Hydrolysis of Acetyl Groups

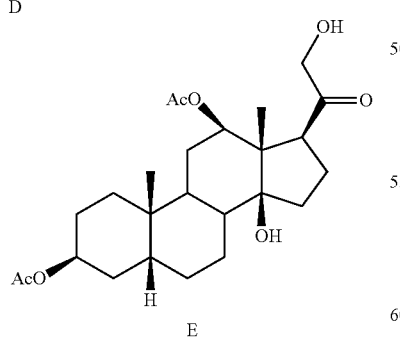

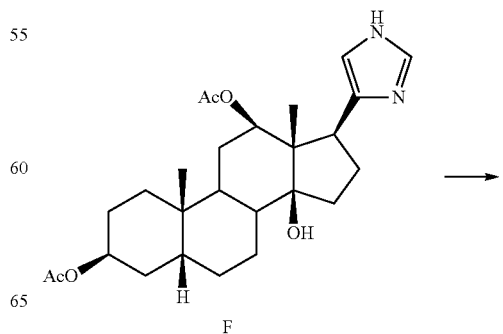

F

-continued

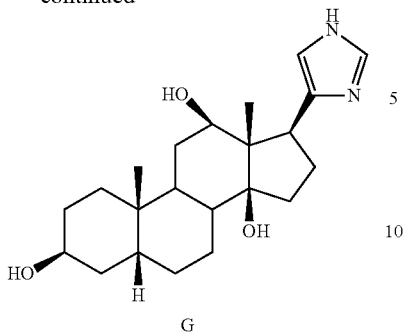

G

To a stirred solution of 470 mg of intermediate F in 17 ml of MeOH, 5.1 ml of 1M NaOH were added and the solution was stirred for 24 hours at room temperature. MeOH was removed under reduced pressure and the residue was diluted with water and extracted with dichloromethane. The organic phase was dried over $MgSO_4$, filtered and the solvent removed under vacuum giving 383 mg (73%) of crude residue as grey/green solid, that was purified trough $SiO_2$ gel column chromatography eluting with DCM/MeOH 8/2, giving 152 mg of pure product G (CVie 104) as white solid.

$^1$H-NMR ($d_6$-DMSO, 600 MHz): 0.40 (s, 3H); 0.83 (s, 3H); 1.08-1.24 (m, 4H); 1.30-1.58 (m, 6H); 1.58-1.82 (m, 6H); 1.82-2.18 (m, 1H); 2.02-2.18 (m, 1H); 3.20 (m, 1H); 3.90 (s, 1H); 4.18 (s, 1H); 4.40 (s, 1H); 6.68 (s, 1H); 7.60 (s, 1H); 11.78 (s, 1H).

Example 4

3β-hydroxy-5β-10β-methyl-12β-hydroxy-13β-methyl-14β-hydroxy-17β-(2-guanidino-thiazol-4-yl) androstane (Cvie 105)

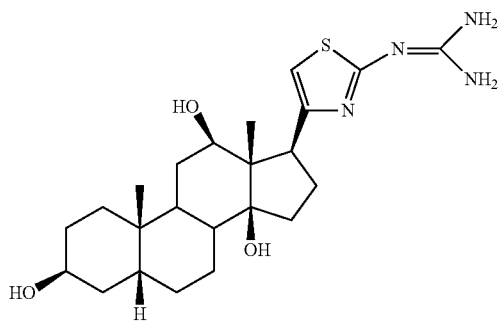 [SMILES: C[C@]12[C@H](O)CC3C(CC[C@@H]4C[C@@H](O)CC[C@]34C)[C@@]1(O)CC[C@@H]2c1csc(N=C(N)N)n1]

Example 3 is repeated until intermediate E.
From Alcohol to Methanesulfonate

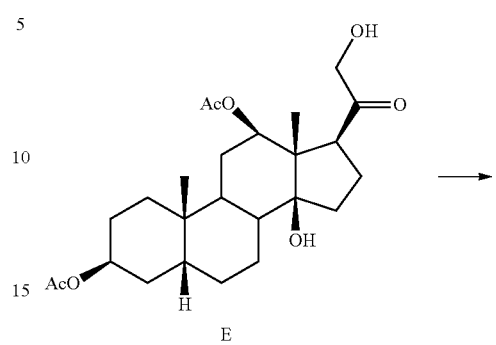

E

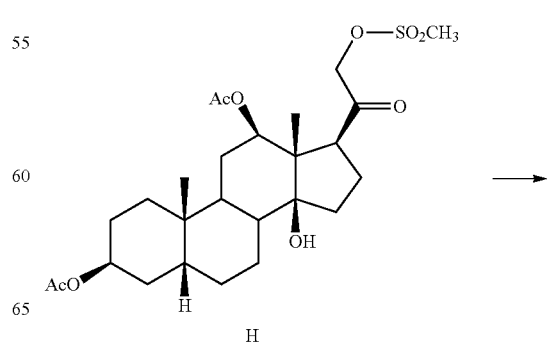

H

To a stirred solution of 0.55 grams of product E in 10 ml of anhydrous dichlorometane, 0.24 ml of triethylamine were added. The solution was cooled at 5° C. and 0.12 ml of Methanesulfonyl chloride were added dropwise and the solution stirred at 5° C. for 10 minutes, then at room temperature for additional 2 hours. The solution was diluted with 10 ml of dichloromethane and washed with 10 μl of a solution of 5% $NaHCO_3$ The aqueous phase was extracted with 50 ml of dichloromethane and the pooled organic phases washed with 10 ml of water. The organic phase was died over $MgSO_4$, and the solvent was removed under reduced pressure, giving 0.64 g (99%) of H as white solid, used in the next step without any further purification.

Building Guanidine-Substituted Imidazole Ring

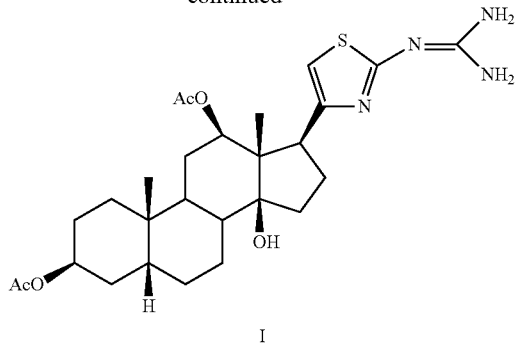

I

To a stirred solution of 0.64 g of intermediate H in 52 ml of Acetone, 2.39 grams of 2-Imino-4-thiobiuret (Amidinothiourea, commercial) were added. The solution was refluxed for 5 hours, cooled down at room temperature and stirred for additional 16 hours. The suspension was filtered, the solid discarded and the acetone removed under reduced pressure.

The solid residue was dissolved with 20 ml of dichloromethane and washed with water. The organic phase was dried over MgSO$_4$, filtered and the solvent removed under vacuum giving 0.59 grams of crude product as yellow solid, that was purified by flash-chromatography (SiO$_2$) (from ethyl acetate/cyclohexane 8/2+1% of TEA—ethyl acetate 99%+1% of TEA as eluent) obtaining 0.40 grams of pure product I (62%)

Hydrolysis of Acetyl Groups

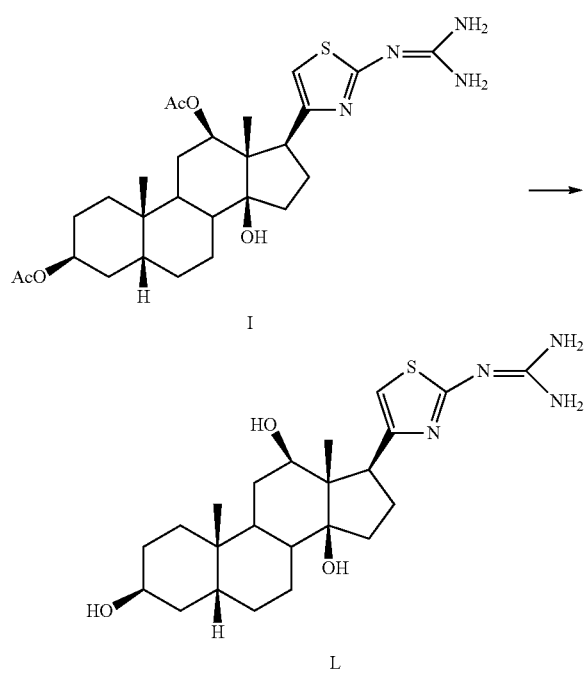

1.9 ml of NaOH 1M were added to a solution of 200 mg of intermediate I in 6 ml of MeOH. The mixture was stirred 24 hours at room temperature then the solvent was removed. The residue was washed with 5 ml of water and filtered giving 131 mg (78%) of compound L (CVie 105) as white solid $^1$H-NMR (d$_6$-DMSO, 600 MHz): 0.50 (s, 3H); 0.87 (s, 3H); 1.01-1.26 (m, 4H); 1.26-1.58 (m, 6H); 1.58-1.62 (m, 2H); 1.62-1.98 (m, 6H); 1.98-2.06 (m, 1H); 3.20 (s, 1H); 3.30-3.38 (m, 1H); 3.90 (s, 1H); 6.19 (s, 1H).

Example 6

3β-hydroxy-5β-10β-methyl-13β-methyl-14β-hydroxy-17β-(N-(3-aminopropyl)-imidazol-4-yl)androstane (CVie 106)

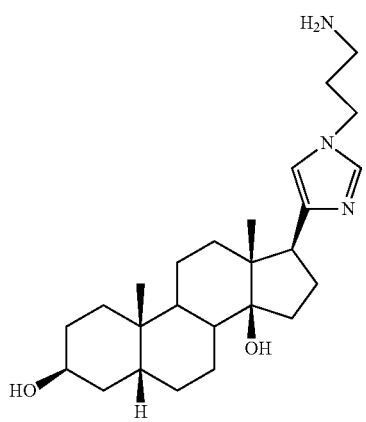 [SMILES: C[C@]12CC[C@H](O)C[C@H]1CCC1C2CC[C@]2(C)[C@@H](c3cn(CCCN)cn3)CC[C@]12O]

Example 1 is repeated until the end product as free base 5.

Preparation of the N-(Aminoalkyl) Derivative

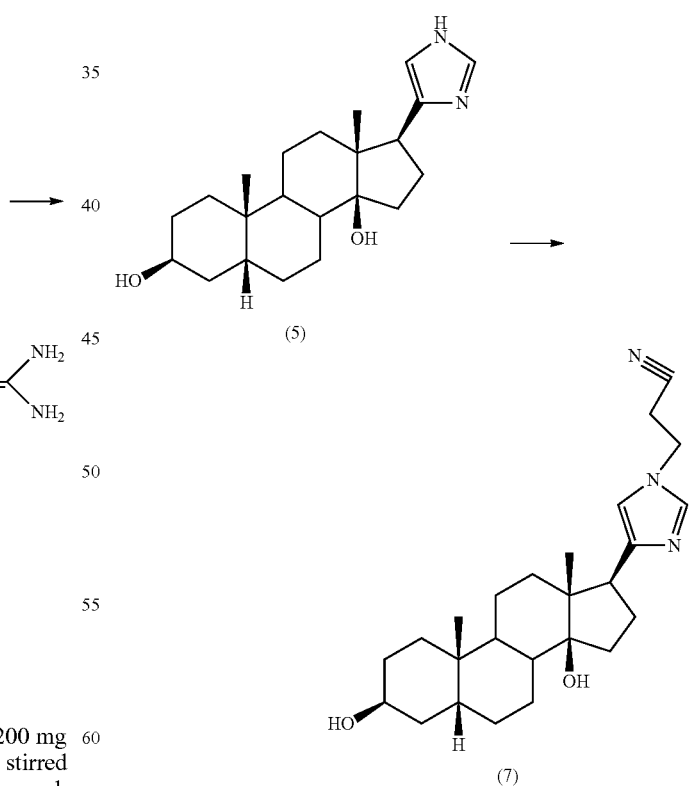

a) Nitrile Derivative

To a stirred solution of 1.42 grams of product 5 in 50 ml of DMSO, 55 mg of K$_2$CO$_3$ and 1.31 ml of Acrylonitrile were added and the mixture was stirred for 24 hours at room temperature. 150 ml of water were added and the mixture was extracted with Ethyl Acetate, the organic phase was dried over $Na_2SO_4$, filtered and the solvent removed under reduced pressure, giving 1.71 g (99%) of intermediate 7, used in the next step without any further purification.

b) Reduction of Nitrile Group

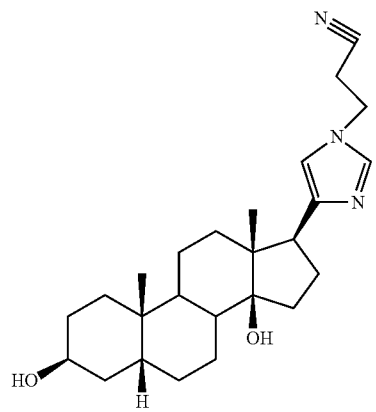

(7)

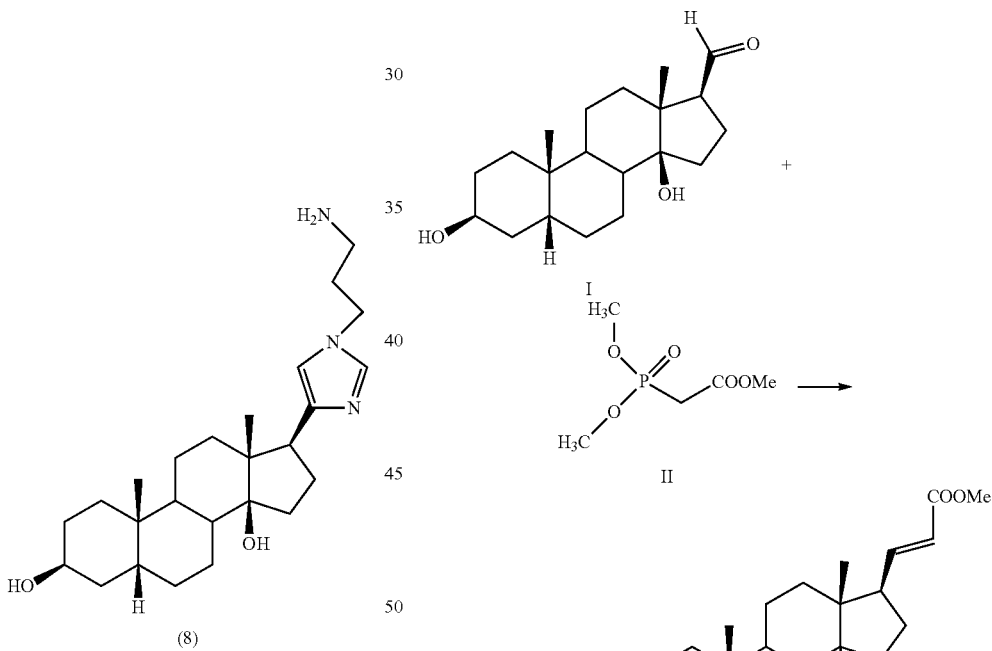

(8)

To a stirred solution of 286 mg of product 7 in 20 ml of THF anhydrous, 340 mg of $LiAlH_4$ were added portion wise and the mixture heated at 80° C. and refluxed for 16 hours, then the cooled solution was diluted with THF and water and a solution of NaOH 4N was added till a white solid was formed. The suspension was filtered, the solid was washed with Ethyl Acetate and purified trough flash chromatography ($SiO_2$) eluting with $CHCl_3/MeOH/NH_3$ 9/1/0.1 giving 204 mg (69%) of product 8 (Cvie 106) as white solid.

$^1$H-NMR ($CDCl_3$, 400 MHz): 0.59 (s, 3H); 0.98 (s, 3H); 1.25-1.35 (m, 4H); 1.35-1.75 (m, 11H); 1.85-2.02 (m, 7H); 2.19-2.24 (m, 2H); 2.69-2.74 (m, 3H); 3.98 (t, 2H); 4.15 (s, 1H); 6.58 (s, 1H); 7.37 (s, 1H).

Example 6B

3β-hydroxy-5β-10β-methyl-13β-methyl-14β-hydroxy-17β-((5-(3-aminopropyl)-isoxazol-3-yl)-ethyl)androstane (Cvie 108)

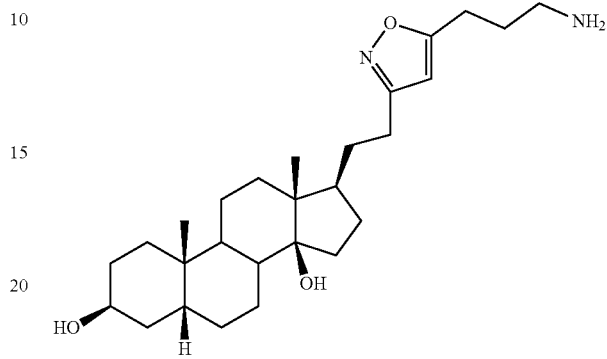

From Aldehyde I to α-Unsaturated Ester

Aldehyde I was prepared according to Gobbini et al. Synth Comm, 27(6), 1115-1122 (1997).

To a suspension of 2.43 g of NaH (55% dispersed in mineral oil) in 73 ml of dry THF, 8.57 ml of Trimethyl Phosphonoacetate II (liquid, commercial) were added dropwise, at 0° C., under Nitrogen atmosphere.

The suspension was left at room temperature for 30 minutes then cooled at 0° C. 10 grams of compound I dissolved in 146 ml of dry THF were added dropwise and the mixture left under stirring for 2 hours at room temperature.

100 ml of EtOAc were added, the mixture transferred into 200 ml of a solution of NaH$_2$PO$_4$ (5% in water) and extracted three times with 150 ml of EtOAc. The pooled organic phases were concentrated to dryness under reduced pressure. The solid residue was suspended in 130 ml of water and kept under stirring for 16 hours, filtered and dissolved in AcOEt and dichloromethane then dried over Na$_2$SO$_4$, filtered and the solvent removed under reduced pressure, giving 11 g (95%) of intermediate III, used in the next step without any further purification.

Reduction of Ester to Alcohol

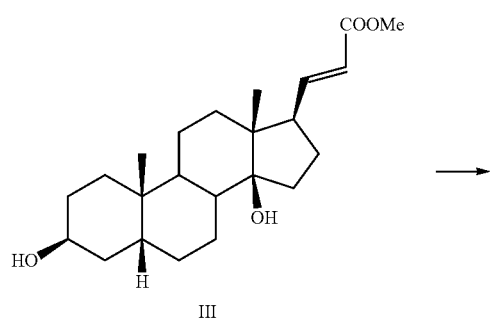

III

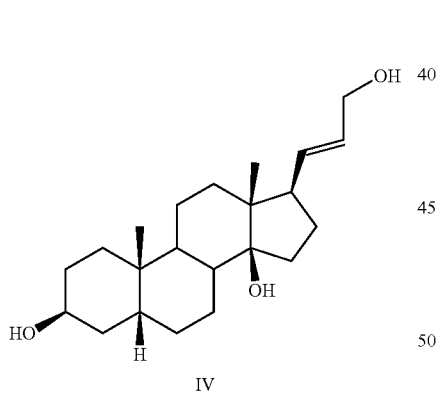

IV

To a solution of 11 grams of compound III in 450 ml of dry THF under N$_2$ atmosphere, at −78° C., 35 ml of neat DIBAH were added dropwise (internal temperature rose up to 65° C.) and the mixture stirred for one hour. After cooling at −78° C., 500 ml of Citric Acid solution (13% in water) were added dropwise in 30 minutes and stirred for 1 hour at room temperature, then 50 grams of NaCl were added and the aqueous phase washed three times with 150 ml of EtOAc. The pooled organic phases were washed with a solution of 5% of NaHCO$_3$, dried over Na$_2$SO$_4$, filtered and the solvent removed under reduced pressure, giving 11.9 g (98%) of intermediate IV, used in the next step without any further purification.

Oxidation of Alcohol to Aldehyde

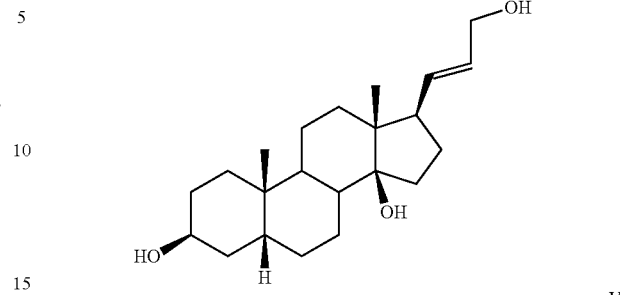

IV

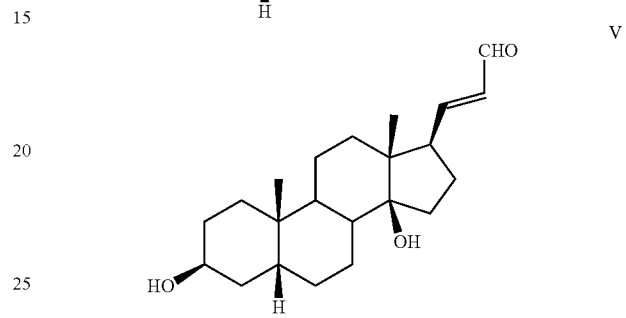

V

To a stirred solution of 11.9 grams of compound IV in 140 ml of dioxane, 75 grams of MnO$_2$ were added and the suspension stirred for 4 hours at room temperature. The mixture was filtered on a celite pad, that was washed with additional 150 ml of AcOEt. The solvents were removed under reduced pressure and the residue was crystallized with 150 ml of Diethyl Ether obtaining 8.4 grams of compound V (83%)

Hydrogenation of Double Bond

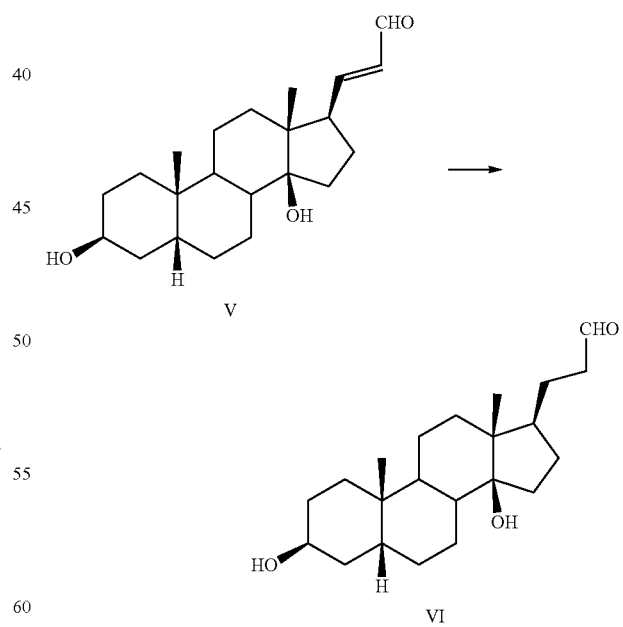

To a solution of 2.95 grams of product V in 600 ml of EtOAc, 55 mg of catalyst Pd/C (5%) were added and the mixture was kept under hydrogen at atmospheric pressure and room temperature for one hour. The mixture was filtered on a celite pad and the filtrate concentrated to dryness under reduced pressure, obtaining 2.95 grams (99%) of product VI

From Aldehyde to Oxime

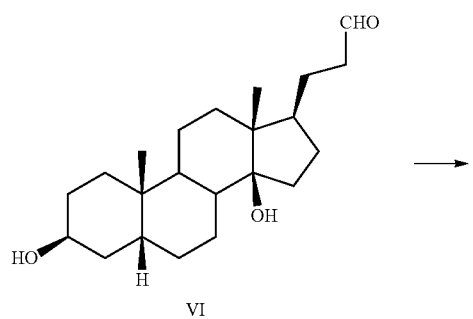

To a stirred solution of 2.7 g of compound VI in 90 ml of dioxane, 670 mg of hydroxylamine hydrochloride and 22.5 ml of NaOH 1M were added. The mixture was stirred for 90 minutes at room temperature, the solvent removed under reduced pressure and extracted with CHCl$_3$. The organic phase concentrated to dryness under reduced pressure obtaining 3.1 g (99%) of product VII

Synthesis of Alkyne

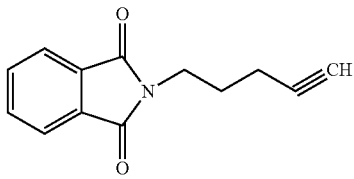 [SMILES: C#CCCCN1C(=O)c2ccccc2C1=O]

To a stirred solution of 1 ml of 4-propyn-1-ol in 40 ml of dry THF, 5.63 grams of PPh$_3$ and 3.16 grams of Phthalimide, at 0° C., were added. 3.35 ml of 1,2-Ethoxycarbonyl diazene solution (DEAD) were added dropwise to the previous solution and the mixture was stirred for 16 hours, then THF was removed under reduced pressure and the residue purified by flash-chromatography (SiO$_2$) (Heptane/diethyl ether 9/1 as eluent) to give 1.92 grams of pure product VIII (84%)

Coupling Alkyne to Oxime

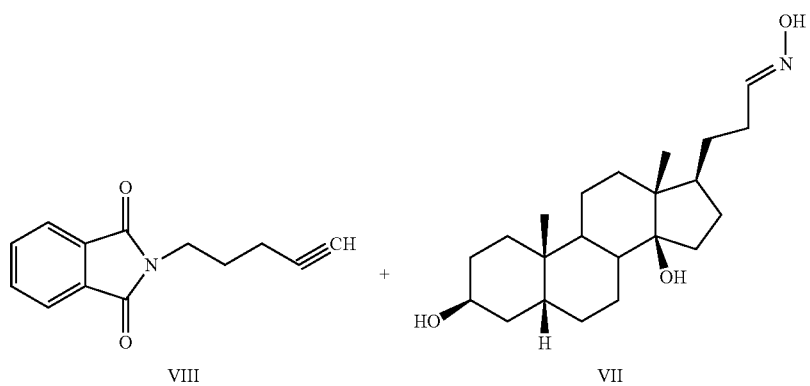

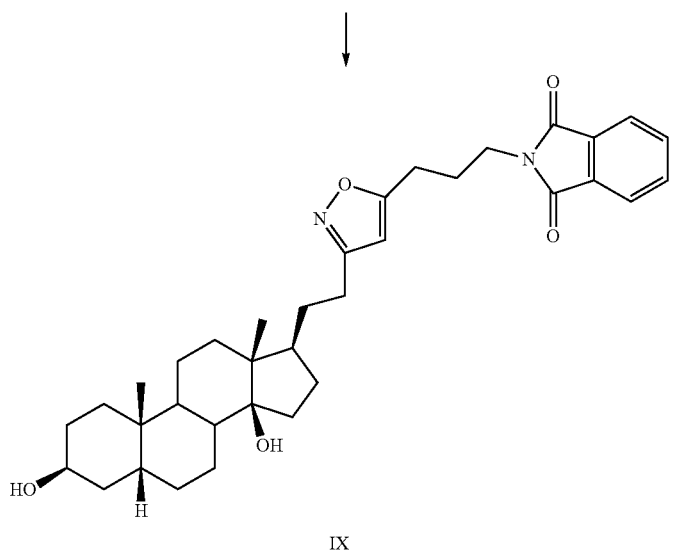

To a suspension of 600 mg of product VII in 8 ml of chloroform containing 0.5% of pyridine, 220 mg N-Chlorosuccinimide were added and the mixture stirred for 10 minutes under $N_2$ atmosphere.

A solution of 240 mg of alkyne VIII in 4 ml of chloroform containing 0.24 ml of TEA, was added dropwise and the mixture stirred at room temperature for 6 hours, diluted with $CHCl_3$ and washed with water. The solvent was removed to dryness under reduced pressure and the residue was purified by flash-chromatography ($SiO_2$) (Heptane/Acetone/ethyl acetate 7/2/2 as eluent) to give 260 mg of pure product IX (35%)

Restoration of Amine

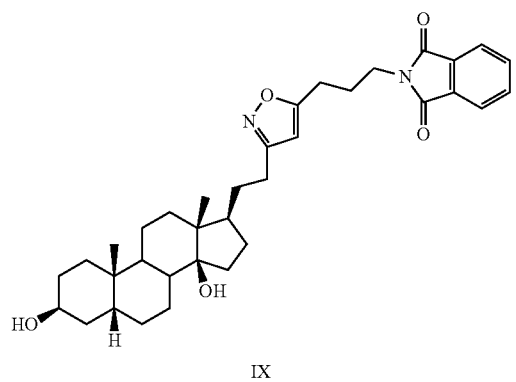

IX

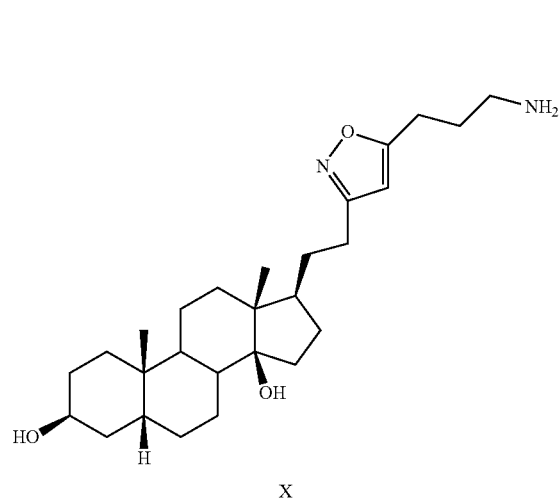

X

The mixture of 350 mg of compound IX and 0.70 ml of Hydrazine hydrochloride in 22 ml of ethanol was refluxed for one hour. The mixture was diluted with water, ethanol was removed under reduced pressure and the residual aqueous part was extracted with $CH_2Cl_2$. The organic phase was removed to dryness under reduced pressure and the residue was purified by flash-chromatography ($SiO_2$) ($CH_2Cl_2$/MeOH/$NH_3$ 9/1/0.1 as eluent) to give 125 mg (44%) of pure product X (CVie 108).

Example 7

3β-hydroxy-5β-10β-methyl-13β-methyl-14β-hydroxy-17β-(pyrazol-3-yl)androstane (Cvie 103)

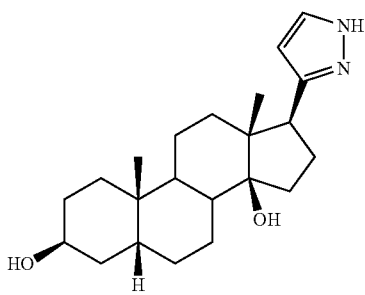 [SMILES: C[C@]12CC[C@H](O)C[C@H]1CCC1C2CC[C@]2(C)[C@@H](c3cc[nH]n3)CC[C@]12O]

Example 6 is repeated until intermediate V.

Building Pyrazole Ring

To a stirred solution of 1 gram of product V in 6 ml of Acetic Acid, 0.58 grams of p-Toluenesulfonyl hydrazide were added. The mixture was stirred for 1 hour at room temperature and diluted with a solution of $Na_2HPO_4$ (5% in water). The suspension was filtered, the solid dried under reduced pressure and solubilised in 30 ml of DMF, adding 400 mg of Potassium tert-butoxide. The mixture was stirred for 1 hour at room temperature, heated to 80° C. for 1.5 hour, then poured in water and extracted three times with Diethyl ether. The pooled organic phases were dried over $Na_2SO_4$, filtered and the solvent removed under reduced pressure. The residue was purified by flash-chromatography ($SiO_2$) ($CH_2Cl_2$/Acetone 7/3/as eluent) to give 296 mg (29%) of pure product (Cvie 103).

Example 8

3β-hydroxy-5β-10β-methyl-13β-methyl-14β-hydroxy-17β-((5-(3-aminopropyl)-isoxazol-3-yl))androstane (Cvie 107)

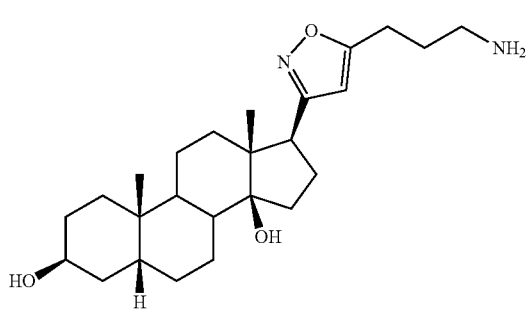 [SMILES: C[C@]12CC[C@H](O)C[C@H]1CCC1C2CC[C@]2(C)[C@@H](c3cc(CCCN)on3)CC[C@]12O]

Preparation of Alkyne

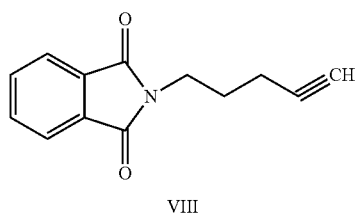

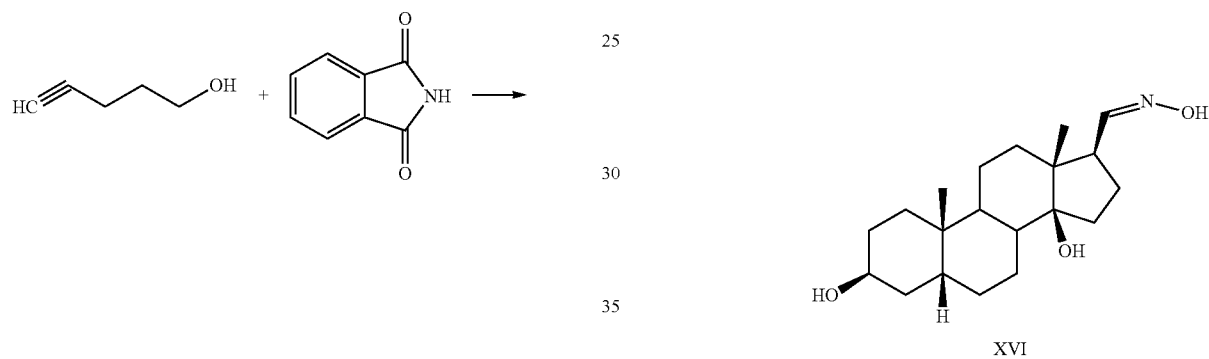

To a stirred solution of 11 of 4-propyn-1-ol in 40 ml of dry THF, 5.63 grams of PPh₃ and 3.16 grams of Phthalimide, at 0° C., were added. 3.35 ml of 1,2-Ethoxycarbonyl diazene solution (DEAD) were added dropwise to the previous solution and the mixture was stirred for 16 hours, then THF was removed under reduced pressure and the residue purified by flash-chromatography (SiO₂) (Heptane/diethyl ether 9/1 as eluent) to give 1.92 grams of pure product VIII (84%)

Aldehyde to Oxime

Aldehyde I was prepared as disclosed above in Example 6. To a stirred solution of 24 ml of Acetate buffer (pH 4.7) and 24 ml of Dioxane, 1.3 grams of hydroxylamine hydrochloride were added and pH corrected with 1N HCl (from 5.75 to 4.8). The solution was diluted with 15 ml of dioxane and a solution of 5 grams of Aldehyde I in Dioxane and water (40 and 16 ml respectively) was added dropwise. After 30 minutes solid NaHCO₃ was added till the solution reached pH 7, the solution extracted with EtOAc, the organic phase was washed with water, dried over Na₂SO₄, filtered and the solvent removed under reduced pressure, giving 5.4 g (99%) of intermediate XVI Coupling Alkyne to Oxime

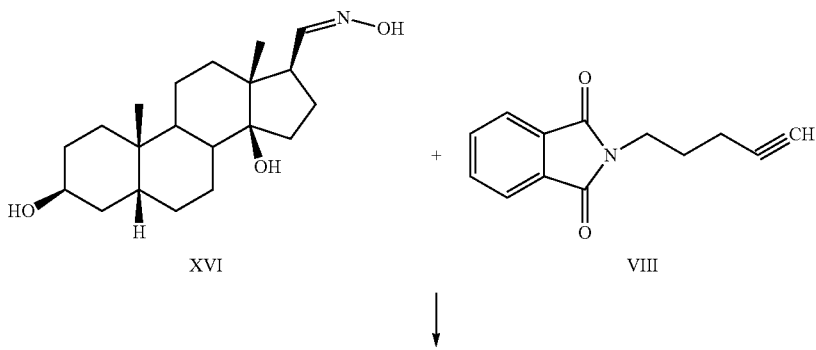

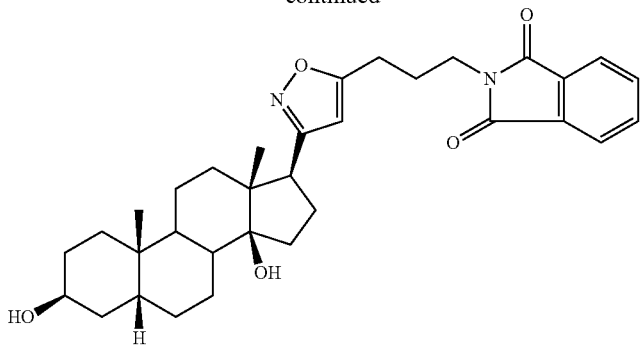

XVII

To a stirred solution of 480 mg of N-Chlorosuccinimide in 15 ml of chloroform containing 0.5% of pyridine, 1.2 grams of solid product XVI were added portion-wise. A solution of alkyne 780 mg of VIII in 12 ml of chloroform containing 0.5% of pyridine and 0.53 ml of TEA was added dropwise, under nitrogen atmosphere, and heated at 45° C. The mixture was stirred for 18 hours, diluted with CHCl$_3$ and washed with water. The solvent was removed to dryness under reduced pressure and the residue was purified by flash-chromatography (SiO$_2$) (CHCl$_3$/Et$_2$O 8/2 as eluent) to give 900 mg of pure product XVII (45%).

Deprotection with Hydrazine

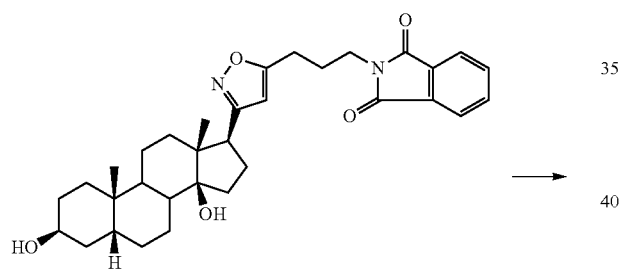

XVII

→

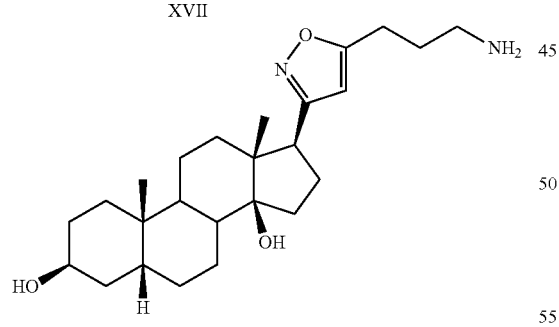

XVIII

The mixture of 350 mg of compound XVII and 1.90 ml of Hydrazine hydrochloride in 60 ml of ethanol was refluxed for 7 hours. The mixture was diluted with water, ethanol was removed under reduced pressure and the residual aqueous part was extracted with CH$_2$Cl$_2$. The organic phase was removed to dryness under reduced pressure and the residue was purified by flash-chromatography (SiO$_2$) (CH$_2$Cl$_2$/MeOH/NH$_3$ 9/1/0.1 as eluent) to give 400 g (60%) of pure product XVIII (CVie 107).

Example 9

3β-hydroxy-5β-10β-methyl-13β-methyl-14β-hydroxy-17β-(5-(2-aminoethyl)-isoxazol-3-yl)-ethyl) androstane (Cvie 109)

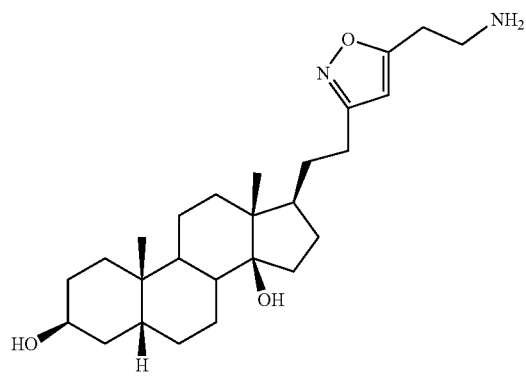 [SMILES: C[C@]12CC[C@H](O)C[C@H]1CCC1C2CC[C@]2(C)[C@@H](CCc3cc(CCN)on3)CC[C@]12O]

Example 6 is repeated till intermediate VII.
Synthesis of Alkyne

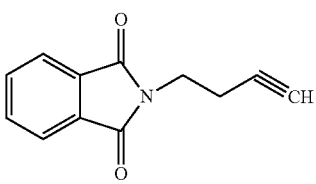

XI

To a stirred solution of 0.70 ml of 3-butyn-1-ol in 34 ml of dry THF, 4.85 grams of PPh$_3$ and 2.72 grams of Phthalimide, at 0° C., were added. 2.89 ml of 1,2-Ethoxycarbonyl diazene solution (DEAD) were added dropwise to the previous solution and the mixture was stirred for 18 hours, then THF was removed under reduced pressure and the residue purified by flash-chromatography (SiO$_2$) (Heptane/diethyl ether 9/1 as eluent) to give 400 mg of pure product XI (21%)

Coupling Alkyne to Oxime

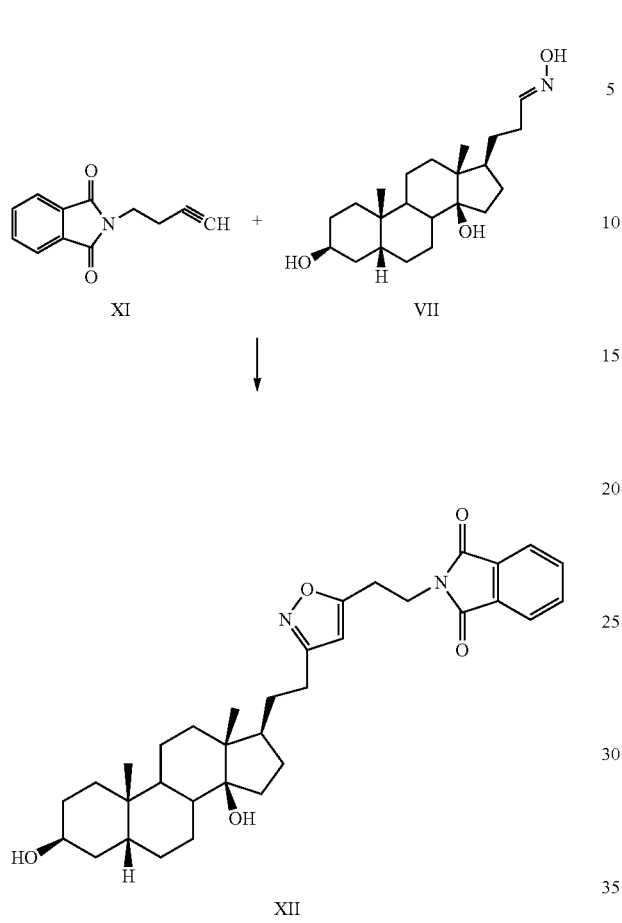

To a suspension of 950 mg of product VII in 12 ml of chloroform containing 0.5% of pyridine, 348 mg N-Chlorosuccinimide were added and the mixture stirred for 10 minutes under N₂ atmosphere. A solution of 600 mg of alkyne XI in 6 ml of chloroform containing 0.38 ml of TEA, was added dropwise and the mixture stirred at room temperature for 6 hours, diluted with CHCl₃ and washed with water. The solvent was removed to dryness under reduced pressure and the residue was purified by flash-chromatography (SiO₂) (Cyclohexane/Acetone/Chloroform 7/2/2 as eluent) to give 330 mg of pure product XII (35%).

Deprotection with Hydrazine

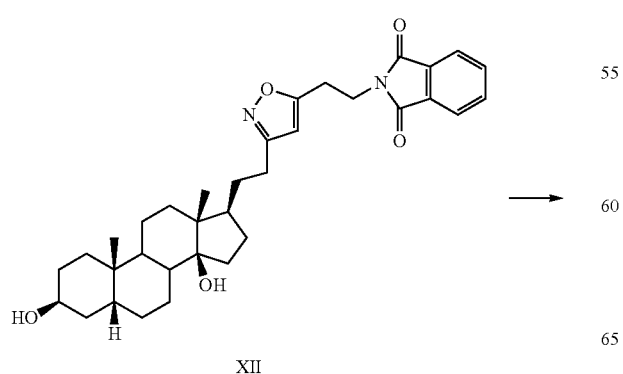

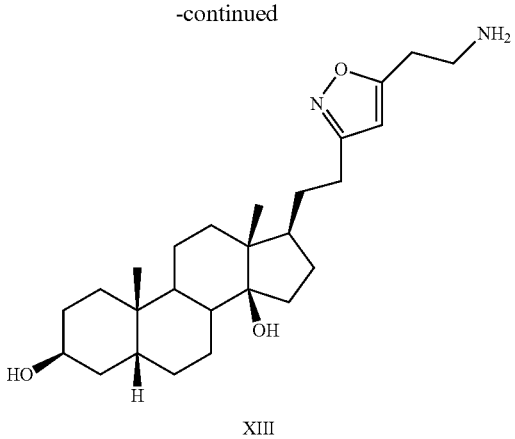

The mixture of 480 mg of compound XII and 0.90 ml of Hydrazine hydrochloride in 27 ml of ethanol was refluxed for one hour. The mixture was diluted with water, ethanol was removed under reduced pressure and the residual aqueous part was extracted with CH₂Cl₂. The organic phase was removed to dryness under reduced pressure and the residue was purified by flash-chromatography (SiO₂) (CHCl₃/MeOH/NH₃ 95/5/0.5 as eluent) to give 130 mg (36%) of pure product XIII (CVie 109)

Preparation of a Pharmaceutically Acceptable Salt

To a stirred solution of 36 mg of product XIII in 1 ml of EtOH, a solution of 4.7 mg of Fumaric Acid in 0.2 ml of EtOH was added. Crystallization was done in 3 ml of Diethyl Ether and the solid obtained was filtered obtaining 25 mg of Fumarate salt.

Example 10

3β-hydroxy-5β-10β-methyl-13β-methyl-14β-hydroxy-17β-(5-(2-aminomethyl)-isoxazol-3-yl)-ethenyl)androstane (Cvie 110)

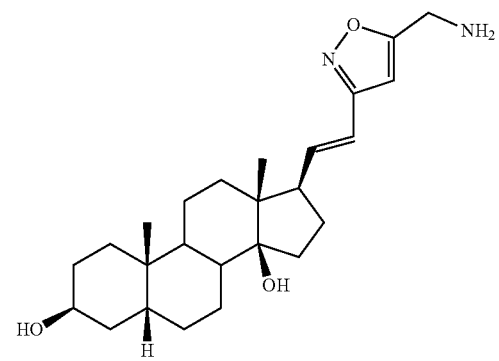 [SMILES: C[C@]12CC[C@H](O)C[C@H]1CCC1C2CC[C@]2(C)[C@@H](/C=C/c3cc(CN)on3)CC[C@]12O]

Preparation of Phosphonate

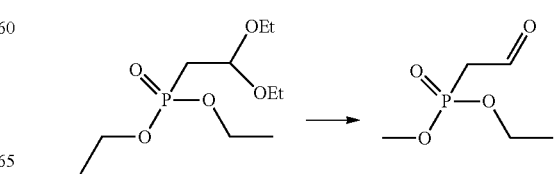

I step: A solution of phosphonate (Acetale) in 45 ml of HCl (2% in water) was refluxed for 10 minutes and cooled at room temperature. 17 grams of NaCl were added and the mixture extracted with CH$_2$Cl$_2$, the organic phase is washed NaHCO$_3$ (5% in water) and with Brine, then dried over Na$_2$SO$_4$, filtered and the solvent removed under reduced pressure, obtaining 10.6 grams of aldehyde.

II Step:

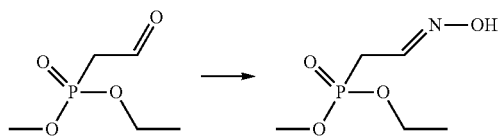

A solution of 5 grams of Hydroxylamine hydrochloride and 5.8 grams of Na$_2$CO$_3$ decahydrate in 45 ml of water was stirred at 0° C. and a solution of 10 grams of Aldehyde in 30 ml of water was added dropwise. The mixture was stirred at room temperature for 24 hours, then saturated with NaCl and extracted with CH$_2$Cl$_2$. The organic phase was washed with 10 ml of water and the solvent removed under reduced pressure, obtaining 10 grams of Oxime Preparation of Alkyne

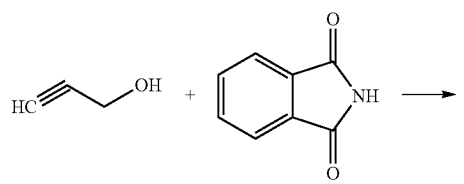

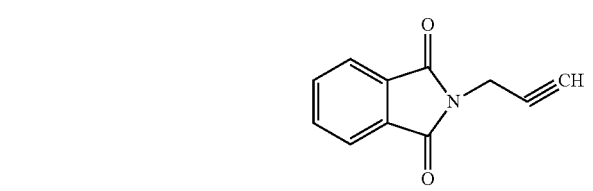

To a stirred solution of 4 ml of 2-propyn-1-ol in 250 ml of dry THF, 36.5 grams of PPh$_3$ and 20.5 grams of Phthalimide were added at 0° C. under nitrogen atmosphere, then 22 ml of DEAD were added dropwise and the mixture stirred for 16 hours. The solid obtained was filtered and purified by flash-chromatography (SiO$_2$) (Cyclohexane/AcOEt 95/5 as eluent) and furtherly crystallized with MeOH to give 3.8 grams (30%) of alkyne.

Coupling Oxime with Alkyne

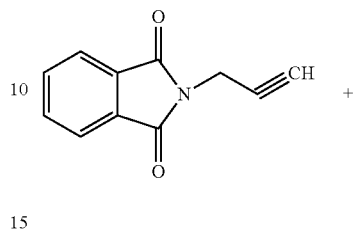

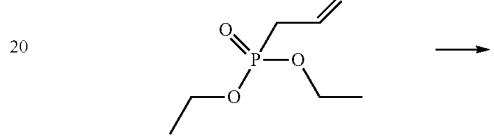

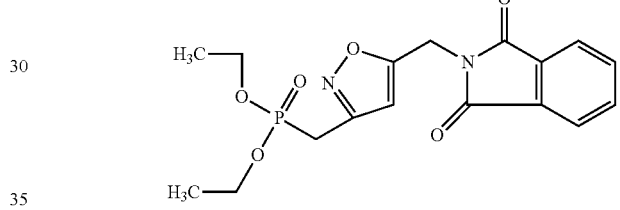

To a suspension of 1.26 grams of N-Chloro succinimide in 15 ml of CHCl$_3$, 6 microliters of Pyridine and a solution of oxime in 15 ml of CHCl$_3$, were added and after 5 minutes 2 grams of solid alkyne, previously prepared were added in portion. The mixture was heated to 50° C. and 1.4 ml of TEA in 5 ml of CHCl$_3$ were added dropwise within one hour. After stirring for 8 hours, the reaction was quenched with water and organic phases separated, the solvent removed under reduced pressure and the crude residue was purified by flash-chromatography (SiO$_2$) (CH$_2$Cl$_2$/Diethyl Ether 1/1 as eluent) to give 1 gram (20%) of pure product phosphonate.

Coupling Aldehyde I with Phosphonate

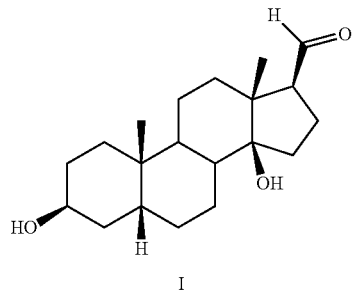

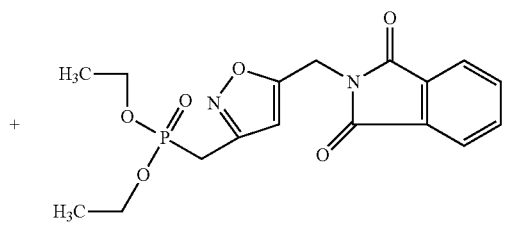

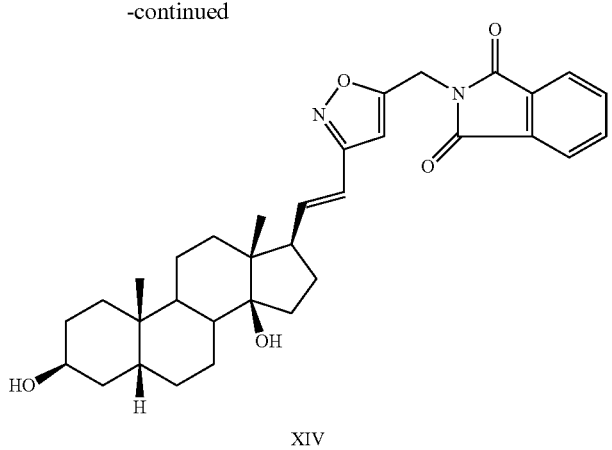

XIV

To a suspension of 290 mg of NaH (55% dispersed in mineral oil) in 14 ml of dry THF, a solution of 2.5 grams of phosphonate in 30 ml of dry THF were added dropwise, at 0° C., under Nitrogen atmosphere. The suspension was left at room temperature for 30 minutes then cooled at 0° C. 1.0 gram of compound I, prepared as in Example 6, was added in small portions and the mixture left under stirring for 6 hours at room temperature. The solution was treated with $NaH_2PO_4$ (5% in water) and extracted with $CHCl_3$. The organic phase was removed to dryness under reduced pressure and 2.6 grams of crude residue was purified by flash-chromatography ($SiO_2$) (Heptane/Diethyl Ether/Acetone 6/3/1 as eluent) to give 370 mg (10%) of pure product XIV.

Deprotection with Hydrazine

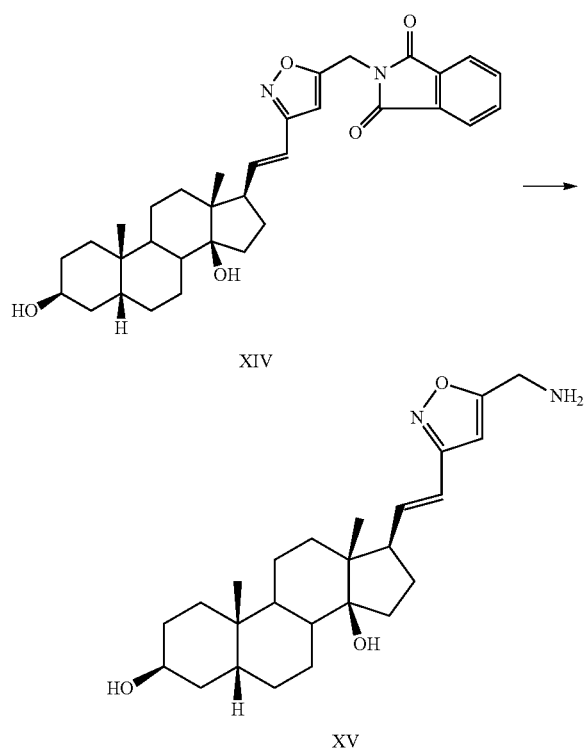

The mixture of 370 mg of compound XIV and 0.70 ml of Hydrazine hydrochloride in 22 ml of ethanol was refluxed for 90 minutes. The mixture was diluted with water, ethanol was removed under reduced pressure and the residual aqueous part was extracted with $CH_2Cl_2$. The organic phase was removed to dryness under reduced pressure and the residue was purified by flash-chromatography ($SiO_2$) ($CH_2Cl_2$/$MeOH/NH_3$ 95/5/0.5 as eluent) to give 150 mg (54%) of pure product XV (Cvie 110).

Preparation of Pharmaceutically Acceptable Salt

To a stirred solution of 153 mg of product XV in 6 ml of EtOH, a solution of 21.5 mg of Fumaric Acid in 1.5 ml of EtOH was added. 10 ml of Hexane were added then the solvents were removed obtaining a glassy solid in quantitative yield.

Biological Activity

Example 11

Procedures
Animal Care

The investigation attains to the Guide of the Care and Use of Laboratory Animals published by the National Institute of Health (NIH publication n° 85-23, revised 1996) and to the guidelines for animal care endorsed by the participating institutions.

Biochemical Measurements in Cell-Free Preparations
Purification of Dog Renal Na,K-ATPase and Na,K-ATPase Activity Assay Purification of renal Na,K-ATPase was performed according to the method of Jorgensen (Methods Enzymol. 1988; 156:29-43). Kidneys were excised from 1-3 year-old male beagle dogs (WuXi AppTec, Suzhou Co., Ltd. 1318 Wuzhong Ave., Wuzhong District Suzhou, 215104 P.R. China) under penthobarbital anesthesia (Import Authorization from Italian Heath Ministry 0009171-09/04/2015-DGSAF-COD_UO-P, 2015). Kidneys were sliced and the outer medulla was dissected, pooled and suspended (1 g/10 ml) in a sucrose-histidine solution, containing 250 mM sucrose, 30 mM histidine and 5 mM EDTA, pH 7.2 and homogenized. The homogenate was centrifuged at 6,000 g for 15 min, the supernatant was decanted and centrifuged at 48,000 g for 30 min. The pellet was suspended in the sucrose-histidine buffer and incubated for 20 min with a sodium-dodecyl-sulphate (SDS) solution dissolved in a gradient buffer, containing 25 mM imidazole and 1 mM EDTA, pH 7.5. The sample was layered on the top of a sucrose discontinuous gradient (10, 15 and 29.4%) and centrifuged at 60,000 g for 115 min. The pellet was suspended in the gradient buffer.

Na,K-ATPase activity was assayed "in vitro" by measuring the release of $^{32}$P-ATP, as described (Ferrandi M. et al. Hypertension 1996; 28(6):1018-25). Increasing concentrations of the standard ouabain, or tested compound, were incubated with 0.3 μg of purified dog kidney enzyme for 10 min at 37° C. in 120 μl final volume of a medium, containing 140 mM NaCl, 3 mM MgCl$_2$, 50 mM Hepes-Tris, 3 mM ATP, pH 7.5. Then, 10 μl of incubation solution containing 10 mM KCl and 20 nCi of $^{32}$P-ATP (3-10 Ci/mmol, Perkin Elmer) were added, the reaction continued for 15 min at 37° C. and was stopped by acidification with 20% v/v ice-cold perchloric acid. $^{32}$P was separated by centrifugation with activated Charcoal (Norit A, Serva) and the radioactivity was measured. The inhibitory activity was expressed as percent of the control samples carried out in the absence of ouabain or tested compound. The concentration of compound causing 50% inhibition of the Na,K-ATPase activity (IC$_{50}$) was calculated by using a multiple parameter non-linear regression best fitting program (Kaleidagraph™, Sinergy Software).

SERCA2a Activity Measurement in Heart Sarcoplasmic Reticulum (SR) Microsomes

Left ventricle tissues were dissected, homogenized in 4 volumes of 10 mM NaHCO$_3$, pH 7, 1 mM PMSF, 10 μg/ml Aprotinin and Leupeptin and centrifuged at 12,000 g for 15 minutes, as published (Nediani C. et al. J Biol Chem. 1996; 271:19066-73). Supernatants were filtered and centrifuged at 100,000 g for 30 min. Contractile proteins were extracted by suspending the pellets with 0.6 M KCl, 30 mM Histidine, pH 7 and further centrifugation at 100,000 g for 30 min. Final pellets were reconstituted with 0.3 M Sucrose, 30 mM Histidine, pH 7.

SERCA2a activity was measured "in vitro" as $^{32}$P-ATP hydrolysis at different Ca$^{2+}$ concentrations (100-4000 nM) in the absence and presence of the tested compounds, as described (Micheletti R. et al. Am J Card 2007; 99:24A-32A). Increasing concentrations of each compound (from 1 to 100 nM) were pre-incubated with 2 μg of microsomes for 5 min at 4° C. in 80 μl of a solution containing 100 mM KCl, 5 mM MgCl$_2$, 1 μM A23187, 20 mM Tris, pH 7.5. Then, 20 μl of 5 mM Tris-ATP containing 50 nCi of $^{32}$P-ATP (3-10 Ci/mmol, Perkin Elmer) were added. The ATP hydrolysis was continued for 15 min at 37° C. and the reaction was stopped by acidification with 100 μl of 20% v/v ice-cold perchloric acid. $^{32}$P was separated by centrifugation with activated charcoal (Norit A, SERVA) and the radioactivity was measured. SERCA2a-dependent activity was identified as the portion of total hydrolytic activity inhibited by 10 μM cyclopiazonic acid (Seidler N W. et al. J Biol Chem. 1989; 264:17816-23).

Dose-response curves were fitted by using a sigmoidal curve fitting software and the maximal velocity (Vmax) activity and the Kd Ca$^{2+}$ were calculated (Synergy Software KaleidaGraph 3.6).

Measurements in Isolated Ventricular Cardiomyocytes

The compounds were characterized for their effect on (i) SR Ca$^{2+}$ uptake function, (ii) action potential (AP) in myocytes freshly dissociated from guinea-pig ventricles by retrograde coronary perfusion with enzymatic solution (Rocchetti M et al. J Pharmacol Exper Therap 2005; 313 (1):207-215).

SR Ca$^{2+}$ Uptake Function (the "Loading Protocol")

Drug effects on SR Ca$^{2+}$ uptake rate were evaluated with an SR "loading protocol" specifically devised to rule out the contribution of the Na/Ca exchanger (NCX) and to assess the uptake rate starting at low levels of SR Ca$^{2+}$ loading. Under voltage-clamp conditions, intracellular Ca$^{2+}$ concentration was dynamically measured by epifluorescence (Fluo4-AM). Membrane current, whose time-dependent component mainly reflected ICaL, was simultaneously recorded. The SR loading protocol consisted in emptying the SR (by a brief caffeine pulse) and then progressively refilling it by voltage steps activating Ca$^{2+}$ influx through the sarcolemmal Ca$^{2+}$ channel (ICaL). NCX was blocked by omission of Na$^+$ from intracellular and extracellular solutions. The procedure is in agreement with published methods, with minor modifications (Rocchetti M et al. J Pharmacol Exper Therap 2005; 313(1):207-215).

Drug effects on SR Ca$^{2+}$ uptake were analysed by considering multiple parameters: 1) the rate at which Ca$^{2+}$ transient (CaT) amplitude increased during the loading protocol, which reflects the rate at which the SR refilled and 2) the time constant of cytosolic Ca$^{2+}$ decay (T$_{decay}$) within each pulse, reflecting net Ca$^{2+}$ transport rate (by SERCA2a) across the SR membrane (a decrease in T$_{decay}$ corresponds to enhanced SR Ca$^{2+}$ uptake).

Specificity of the "loading protocol" in detecting SERCA2a activation is supported by the observation that it did not detect any effect of digoxin, an inotropic agent blocking the Na$^+$/K$^+$ pump, but devoid of SERCA2a stimulating effect (Rocchetti M et al. J Pharmacol Exp Ther 2005; 313:207-215; Alemanni M et al. JMCC 2011; 50:910-918).

Action Potential Measurements

The action potential (AP) contour provides a first-line estimate of the integrated function of membrane ion channels and its changes may disclose ancillary actions, potentially resulting in untoward effects of the compound. To increase sensitivity of the AP contour as a reporter, effects on the rate-dependency of AP parameters were also tested, thus providing a multiparametric (more stringent) approach.

APs were recorded in normal Tyrode's solution at 36.5° C. The following parameters were measured at 4 stimulation rates (0.5-1-2-4 Hz): diastolic membrane potential (E$_{diast}$), maximum depolarization velocity (dV/dt$_{max}$), action potential duration (APD at 90%, 50% and 20% of repolarization), time constant (τ) of APD adaptation after a step change in stimulation rate. Short term APD variability (STV) during steady-state pacing, an index of repolarization stability, was measured as the sum of absolute ortogonal deviations from the identity line in the APD$_n$fAPD$_{n+1}$ plot (Poincare plot) (Altomare C et al, Circulation A&E 2015; 8:1265-1275).

Drug Bioavailability Studies in Rats

Bioavailability has been measured in rats by Sundia MediTech Service, China. The tested compound CVie 101 was intravenously infused at 1 mg/kg and orally administered at 10 mg/kg. Plasma concentrations of the tested compound were measured at intervals from time 0 to time 24 h and detected by LC-MS method. F (%) was calculated.

Drug Toxicity Studies in Mice

194. Acute toxicity has been determined in the mouse (Albino Swiss CD-1, body weight 30 g). Mice were orally treated, or intravenously injected, with single administration of increasing doses of the test substance to identify the dose causing 50% mortality. Mortality occurred within 30 min after the administration and survival after 24 h. The acute toxicity (LD$_{50}$) was then assessed.

Haemodynamic Studies for Inotropic and Lethal Dose Determination in Guinea Pig

Guinea-pigs (400-450 g) were anaesthetized with urethane (1.5 g/kg ip). A microtip pressure transducer was introduced into the left ventricle through the right carotid artery to measure ventricular pressure (LVP); the transducer was coupled with a transducer amplifier. Recordings were fed to a polygraph and analyzed. A polythene cannula was inserted into a jugular vein for drug infusion. After a stabilization period, the test substance was injected at the rate of 0.16 ml/min for 90 min (Micheletti R et al. J Pharmacol Exp Ther 2002; 303:592-600).

The following parameters were obtained: heart rate (HR), left ventricular pressure (LVP), maximal velocity of pressure rise (+dP/dtmax) and decay (−dP/dtmax), ECG. For inotropy, the time elapsed until +dP/dtmax increased by 80% was identified in order to determine the ED80 (dose increasing basal +dP/dtmax by 80%). The time to the maximum increase in +dP/dtmax was also identified to determine the maximum effective dose, EDmax. Lusitropy was characterized by the dose inducing the maximum decrease in −dP/dtmax, (EDmax). As indexes of toxicity, the dose administered until the onset of arrhythmias and the dose inducing death (LD) were calculated. The safety ratio for the tested compound was also calculated as the ratio between LD and ED80.

CVie 101 was iv infused at 0.2 and 0.4 mg/kg/min in comparison to the reference compound Digoxin, administered at 0.016 mg/kg/min for 90 min.

Haemodynamic Studies in Streptozotocin Diabetic Rat (Echocardiography 2M-Doppler-Tissue Doppler)

Sprague Dawley male rats (150-175 g) were made diabetic by a single injection into the tail vein of a solution of streptozotocin (STZ, 50 mg/kg, Sigma-Aldrich), freshly prepared in 0.1 M sodium citrate buffer, pH 4.5. Control rats received citrate buffer. Fasting glycaemia was measured after 1 week and rats with values >400 mg/dl were considered diabetic.

Eight-nine weeks after STZ injection, rats were submitted to transthoracic echocardiographic and Doppler evaluation performed under pentobarbital anesthesia. Two-dimensionally guided M-mode recordings were used to obtain short-axis measurements of left ventricular end-diastolic diameter (LVEDD), left ventricular end-systolic diameter (LVESD), posterior (PW) and septal (SW) diastolic wall thickness according to the American Society of Echocardiography guidelines (Lang R M et al. Eur J Echocardiography 2006; 7:79-108). Fractional shortening was calculated as FS= (LVEDD-LVESD)/LVEDD. Relative wall thickness was calculated as PWTd+IVSTd/LVEDD.

Mitral inflow was measured by pulsed Doppler at the tips of mitral leaflets from an apical 4-chamber view to obtain early and late filling velocities (E, A) and deceleration time of early filling velocity (DT). The deceleration slope was calculated as E/DT ratio. The mitral deceleration index was calculated as DT/E ratio.

Tissue Doppler Imaging (TDI) was evaluated from the apical 4-chamber view to record septal mitral annular movements, i.e., peak myocardial systolic (s') and early and late diastolic velocity (e' and a').

Compound CVie 101 was orally administered to STZ injected rats at the dose of 20 mg/kg and echocardiographic parameters were measured after 1 h. Digoxin, at 20 mg/kg os, was used as reference drug.

Statistical Analysis

Whole animal experiments: Data are reported as mean±SD. Statistical analysis was performed by Student's t-test (paired t test).

Isolated myocyte experiments: Data are reported as mean±SE. Curves including multiple means were compared by two-way ANOVA for repeated measurements; drug-induced changes in overall curve steepness were defined according to significance of the "factor X group" interaction. Due to inadequate monoexponential fit of $Ca^{2+}$ decay, $\tau_{decay}$ was not estimated in a few cells for which CaT data are reported; the sample size (N) reported in FIG. 1 (N≥13 for CVie 101 and N≥11 for CVie 102) refers to cells for which all parameters were available. STV dependency on mean APD was quantified by linear regression.

P<0.05 was regarded as statistically significant in all comparisons.

Biological Results

In Vitro Screening
Inhibition of Dog Renal Na,K-ATPase Activity

Tested compounds inhibited the enzymatic activity of the purified Na,K-ATPase with $IC_{50}$, expressed in μM, as shown in Table 1. Compounds have been compared with the reference drugs Digoxin and Digoxigenin (Table 1).

TABLE 1

| Inhibition of dog renal Na, K-ATPase | |
|---|---|
| Compound | $IC_{50}$, μM |
| DIGOXIN | 0.3 |
| DIGOXIGENIN | 0.23 |
| CVie 101 | 0.71 |
| CVie 102 | 1.7 |
| CVie 103 | 4.0 |
| CVie 104 | 1.61 |
| CVie 105 | 0.53 |
| CVie 106 | 10.0 |
| CVie 107 | 0.15 |
| CVie 108 | 3.3 |
| CVie 109 | 1.0 |
| CVie 110 | 0.33 |

SERCA2a ATPase Activity in Heart-Derived SR Microsomes from Normal Dog

Compounds have been tested on SERCA2a activity in a range of concentrations from 1-100 nM. For measurements in normal dog preparations, the effect of the compounds has been expressed as 0 increase of SERCA2a Vmax activity of a control sample run in the absence of compound (Table 2). Data are mean±SD, n=number of experiments, *at least p<0.05.

At nanomolar concentrations, the tested compounds stimulated SERCA2a Vmax activity of normal dog heart preparations (Table 2). These results indicate a lusitropic effect of tested compounds. At variance with these, Digoxin failed to stimulate SERCA2a activity (Rocchetti M et al. J Pharmacol Exp Ther 2005; 313:207-215; Ferrandi M et al. Br J Pharmacol 2013; 169:1849-61).

TABLE 2

| SERCA2a ATPase activity in heart-derived SR microsomes from normal dog | | | |
|---|---|---|---|
| Compound | Concentration nM | Vmax (μmol/min/mg prot) mean ± SD | % increase vs Control *p < 0.05 |
| CVie 101 | 0 | 2.373 ± 0.079 (n = 7) | 0 |
| | 10 nM | 2.737 ± 0.336 (n = 7) | 15%* |
| | 100 nM | 2.832 ± 0.198 (n = 7) | 19%* |
| CVie 102 | 0 | 2.359 ± 0.192 (n = 11) | 0 |
| | 1 nM | 2.949 ± 0.321 (n = 6) | 25%* |
| | 10 nM | 2.660 ± 0.232 (n = 12) | 13%* |
| CVie 103 | 0 | 2.320 ± 0.149 (n = 7) | 0 |
| | 10 nM | 2.569 ± 0.278 (n = 7) | 11%* |
| | 100 nM | 2.688 ± 0.285 (n = 7) | 16%* |

TABLE 2-continued

SERCA2a ATPase activity in heart-derived SR microsomes from normal dog

| Compound | Concentration nM | Vmax (μmol/min/mg prot) mean ± SD | % increase vs Control *p < 0.05 |
|---|---|---|---|
| CVie 104 | 0 | 1.290 ± 0.138 (n = 4) | 0 |
|  | 1 nM | 1.437 ± 0.158 (n = 4) | 11%* |
|  | 10 nM | 1.551 ± 0.275 (n = 4) | 20%* |
| CVie 106 | 0 | 2.553 ± 0.216 (n = 6) | 0 |
|  | 1 nM | 3.113 ± 0.157 (n = 3) | 22% * |
|  | 10 nM | 2.935 ± 0.403 (n = 3) | 15% |
| CVie 107 | 0 | 2.346 ± 0.109 (n = 3) | 0 |
|  | 10 nM | 2.508 ± 0.339 (n = 3) | 7% |
|  | 100 nM | 2.751 ± 0.171 (n = 3) | 17%* |
| CVie 108 | 0 | 2.562 ± 0.214 (n = 8) | 0 |
|  | 1 nM | 2.94 ± 0.306 (n = 3) | 15% |
|  | 10 nM | 2.980 ± 0.441 (n = 4) | 16%* |
| CVie 109 | 0 | 2.518 ± 0.244 (n = 4) | 0 |
|  | 10 nM | 2.859 ± 0.504 (n = 4) | 14% |
|  | 100 nM | 2.889 ± 0.305 (n = 4) | 15%* |
| CVie 110 | 0 | 2.457 ± 0.198 (n = 5) | 0 |
|  | 1 nM | 2.924 ± 0.549 (n = 3) | 19% |
|  | 10 nM | 2.903 ± 0.188 (n = 3) | 18%* |

Studies in Intact Cardiomyocytes
Functional Evaluation in Guinea Pig Isolated Cardiomyocytes
SR $Ca^{2+}$ Uptake Function (the "Loading Protocol")

CVie 101 (100 nM) increased the rate of $Ca^{2+}$ transient (CaT) increment during SR reloading (FIG. 1A) and, once CaT amplitude achieved a threshold value (at the 5$^{th}$ pulse), decreased the time constant of cytosolic $Ca^{2+}$ decay within each pulse ($\tau_{decay}$, FIG. 1B).

Similarly, CVie 102 (100 nM) increased the rate of CaT increment during the protocol (FIG. 1C) and reduced $\tau_{decay}$ within each pulse (FIG. 1D).

These results converge to indicate that CVie 101 and CVie 102 significantly increased $Ca^{2+}$ uptake by the SR. Under experimental conditions applied, SR $Ca^{2+}$ uptake was entirely supported by SERCA2a; therefore, the results are consistent SERCA2a activation by the two agents.

Action Potential Measurements

Figure 2:
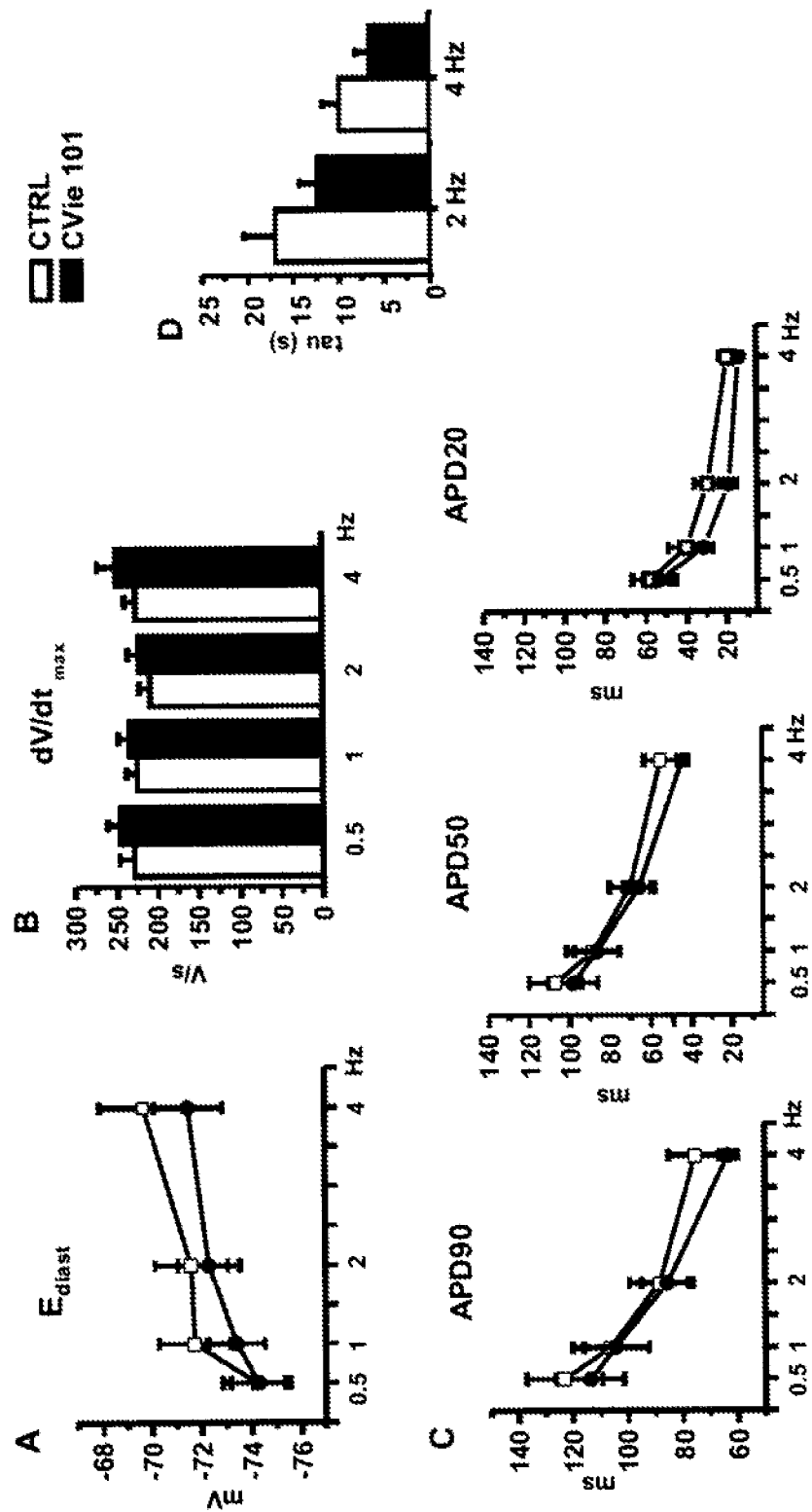
FIG. 2 shows the effect of CVie 101 on action potential (AP) features at various stimulation rates (Hz). A) diastolic membrane potential ($E_{diast}$); B) maximum velocity of action potential upstroke ($dV/dt_{max}$); C) action potential duration (APD) at 90%, 50% and 20% of repolarization; D) time constant of APD adaptation (tau) after a step increase in stimulation rate. CTRL=control. CTRL N=12; CVie 101 N=14. Differences between CTRL and CVie were not statistically significant for all parameters.
Figure 3:
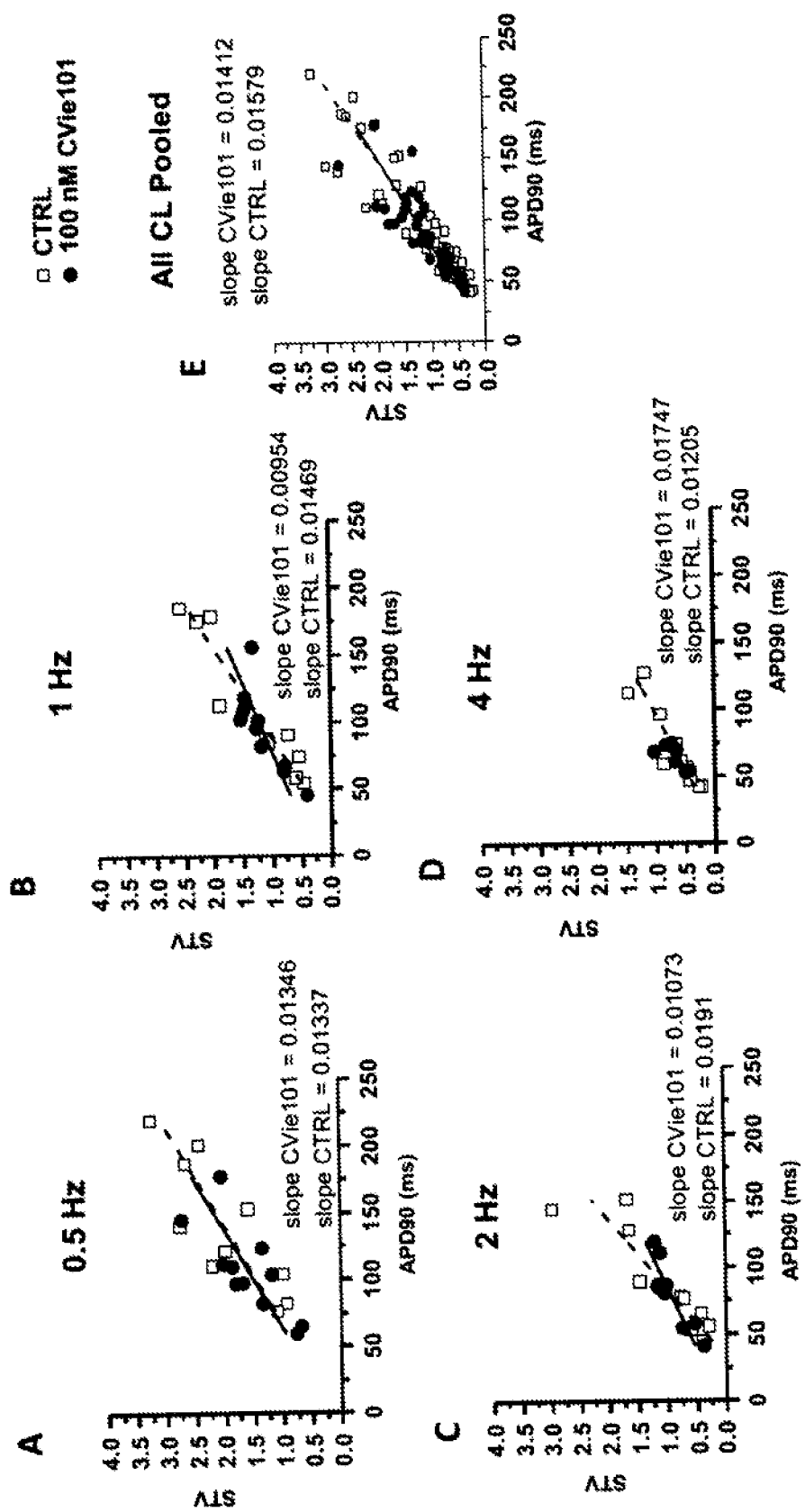
FIG. 3 shows the effect of CVie 101 on the dependency of APD short-term variability (STV) on mean APD. A-D) STV plotted as a function of mean $APD_{90}$ during steady-state stimulation at 4 rates (Hz); solid lines are linear fits of data points; E) STV values at all stimulation rates are pooled. CTRL=control. CTRL N=10, CVie 101 N=11

The action potential (AP) contour provides an estimation of the integrated function of membrane ion channels and its changes may disclose ancillary actions that may potentially result in untoward effects of the compounds. To this end, drug effects on AP parameters were evaluated. At the same concentration exerting a significant effect on SERCA2a (100 nM), CVie 101 did not affect diastolic membrane potential ($E_{dlast}$, FIG. 2A), maximum depolarization velocity (dV/dt$_{max}$, FIG. 2B), action potential duration (APD at 90%, 50% and 20% of repolarization) and its cycle-length dependency at steady-state (FIG. 2C). The time constant (T) of APD adaptation after a step change in cycle length was not shortened by the drug (FIG. 2D). Short term APD variability (STV), measured at 4 different frequencies separately (0.5-1-2-4 Hz) (FIG. 3A-B-C-D), or pooled together (FIG. 3E), resulted also unaffected by CVie 101. These results indicate that CVie 101 did not impact on myocyte electrical activity.

Cvie 102 is a compound structurally related to CVie 101 and therefore CVie 102 has not been tested on AP parameters because it was expected to be inactive.

Collectively, the multiparametric approach used for AP analysis clearly demonstrates the absence of undesired drug effects of CVie 101 on cardiac electric activity. The same is applied to CVie 102. Therefore, these two molecules are selective compounds for SERCA2a modulation (positive lusitropic drug).

In Vivo Studies
Bioavailability in Rats

Figure 4:
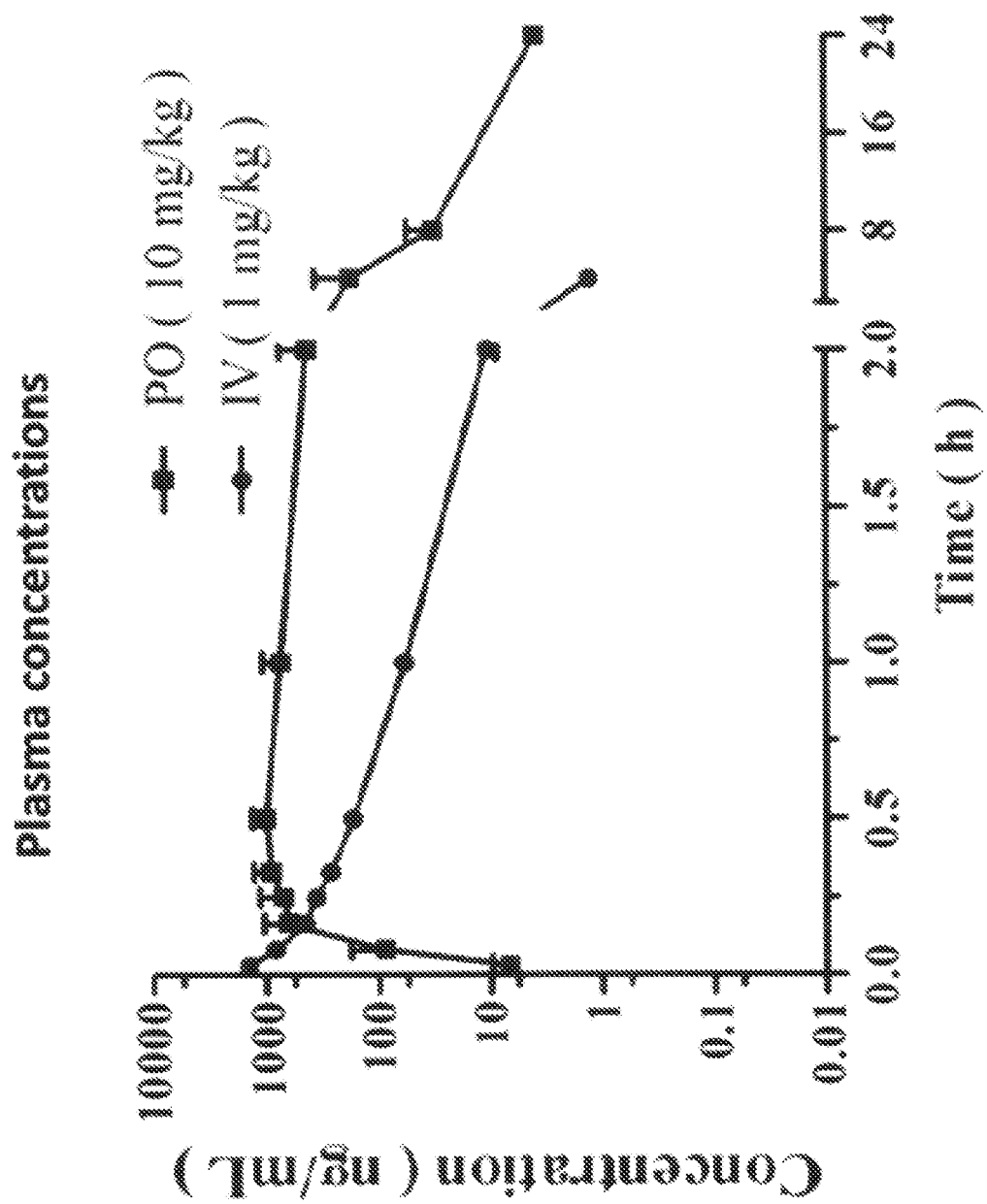
FIG. 4 shows bioavailability of CVie 101 in rats

Bioavailability of CVie 101 has been measured in rats after an intravenous injection (i.v.) of 1 mg/kg and an oral administration (os) at 10 mg/kg by Sundia MediTech Service, China. Plasma concentrations of the tested compound CVie 101 were measured at intervals from time 0 to time 24 h and detected by LC-MS method (FIG. 4). F value (%) has been calculated and resulted to be 66, 3% (Table 3).

TABLE 3

Bioavailability parameters of CVie 101 in rats
Bioavailability parameters

|  | Mean | SD |
|---|---|---|
| HL_Lambda_z (T1/2 · h) | 2.21 | 0.72 |
| Tmax (h) | 0.50 | 0.00 |
| Cmax (ng/ml) | 1020.9 | 340.4 |
| AUClast (h * ng/mL) | 2428.5 | 1540.3 |
| AUCINF_pred (h * ng/mL) | 2493.7 | 1494.0 |
| MRTlast (h) | 2.03 | 0.56 |
| Vz_F_pred (L/kg) | 14.29 | 5.03 |
| Cl_F_pred (L/h/kg) | 4.88 | 2.19 |
| λz Calculation Time Range (h) | NA | NA |
| F (%) | 66.3 | 42.07 |

Acute Toxicity in Mouse

The acute toxicity of the tested compound CVie 101 has been determined in the mouse (Albino Swiss CD-1, body weight 30 g). CVie 101 has been orally administered or intravenously injected at increasing doses to identify the dose causing 50% mortality. Mortality occurred within 30 min after the administration and survival after 24 h.

The results for CVie 101 acute toxicity are reported in Table 4. As comparison, the acute toxicity for the reference compound Digoxin has been also included, according to literature data (www.lookchem.com, Reference for Digoxin i.v.: Afifi A M, Ammar E M. Pharmacological Research Communications. Vol. 6, Pg. 417, 1974; Reference for Digoxin os: Archives Internationales de Pharmacodynamie et de Therapie. Vol. 153, Pg. 436, 1965) (Table 4).

TABLE 4

Acute toxicity (LD$_{50}$) of Digoxin and CVie 101 in mouse

| Compound | LD$_{50}$ mg/kg |
|---|---|
| CVie 101 i.v. | 20 |
| CVie 101 os | 350 |
| Digoxin i.v. data from literature | 7.7 |
| Digoxin os data from literature | 17.8 |

Inotropic and Lethal Dose in Guinea Pig

Haemodynamic parameters have been measured in guinea pig after 90 min of a slow i.v. infusion of Digoxin at 0.016 mg/kg/min, CVie 101 at 0.2 and 0.5 mg/kg/min and CVie 102 at 0.3 mg/kg/min. Table 5 summarizes the parameters. CVie 101 produced an increase in dP/dtmax that reached the 80% (ED80) at the cumulative dose of 1.6 and 2.34 mg/kg and a peak of 163.6% and 278.7% over basal, respectively, at the dose (EDmax) of 3.73 and 7.49 mg/kg. CVie 102 produced an increase in dP/dtmax with an ED80 at the cumulative dose of 3.8 mg/kg and a peak of 138.3% over basal at the dose (EDmax) of 8.6 mg/kg. Digoxin afforded an increase of 128% at the cumulative dose (EDmax) of 0.96 mg/kg and an ED80 of 0.69 mg/kg. Safety profile of CVie 101 and CVie 102 appeared consistently better than that of Digoxin in terms of lethal dose (LD), number of dead/treated animals and LD/ED80 ratio (Table 5).

TABLE 5

Haemodynamics of Digoxin, CVie 101 and CVie 102 in guinea pig

| Compound | Dose mg/kg/min | E max % increase in dP/dtmax | ED max mg/kg | ED$_{80}$ mg/kg | Lethal dose mg/kg | Dead/ treated number | LD/ ED$_{80}$ |
|---|---|---|---|---|---|---|---|
| Digoxin | 0.016 | 128.04 | 0.96 | 0.69 | 1.20 | 5/7 | 2.41 |
| CVie 101 | 0.2 | 163.6 | 3.73 | 1.60 | >18 | 1/8 | n.d. |
|  | 0.5 | 216.8 | 5.08 | 2.74 | 28.2 | 8/8 | 11.32 |
| CVie 102 | 0.3 | 138.3 | 8.6 | 3.8 | 12.57 | 11/11 | 5.42 |

Haemodynamics in Streptozotocin Diabetic Rats (Echocardiography 2M-Doppler-Tissue Dopler)

Table 6 shows the comparison among vehicle (saline), CVie 101 and Digoxin, both at 20 mg/kg, before and after 8h oral treatment on haemodynamic parameters in STZ diabetic rats. Data are mean±SD; values with asterisk are statistically significant with at least $p<0.05$.

The data indicate that in an animal model characterized by a diastolic dysfunction, such as the streptozotocin diabetic rats, CVie 101 ameliorated diastolic function with a significant reduction of E/e' ratio, an increase of e' associated with an increase of SV, without any change of heart rate (Table 6). Conversely, Digoxin induced opposite effects: increased E/e' ratio, increased heart rate and did not affect stroke volume. The different effects of CVie 101 and Digoxin on the impaired cardiac function of STZ rats are consistent with the SERCA2a stimulatory activity of CVie 101 that, by correcting the depressed cardiac relaxation, increases the amount of blood available for contraction, thus resulting in an increase of SV produced by CVie 101 but not by Digoxin.

TABLE 6

Haemodynamic parameters after Digoxin and CVie 101 oral treatment of STZ diabetic rats

| Function | Echo Parameter | SALINE before (n = 12) | SALINE after (n = 12) | Cvie101 Before (n = 12) | Cvie101 20 mg/kg after (n = 12) | DIGO Before (n = 12) | DIGO 20 mg/kg After (n = 12) |
|---|---|---|---|---|---|---|---|
| Systolic | FS | 41.7 ± 5.18 | 40.8 ± 4.28 | 39.6 ± 4.9 | 45.1 ± 3.4* | 42.6 ± 3.32 | 47.2 ± 3.24* |
|  | S' | 24.0 ± 2.16 | 23.5 ± 2.71 | 23.3 ± 2.5 | 23.8 ± 3.6 | 24.2 ± 2.53 | 26.7 ± 2.77* |
| Diastolic | E | 0.98 ± 0.1 | 0.96 ± 0.1 | 0.90 ± 0.1 | 0.96 ± 0.14* | 0.92 ± 0.1 | 1.02 ± 0.13* |
|  | A | 0.89 ± 0.16 | 0.80 ± 0.11* | 0.75 ± 0.13 | 0.76 ± 0.17 | 0.79 ± 0.18 | 0.92 ± 0.1* |
|  | E/A | 1.11 ± 0.13 | 1.22 ± 0.16* | 1.22 ± 0.15 | 1.29 ± 0.22 | 1.19 ± 0.19 | 1.11 ± 0.16 |
|  | DT | 46 ± 12.4 | 50.9 ± 5.99 | 53.2 ± 4.6 | 47.7 ± 4.8* | 50.2 ± 9.08 | 39.2 ± 9.34* |
|  | DT/E | 47.8 ± 15.1 | 53.5 ± 8.0 | 60.2 ± 13.2 | 51.0 ± 10.2* | 55.6 ± 12.2 | 39.2 ± 11.2* |
|  | E/DT | 23.2 ± 8.5 | 19.0 ± 2.8* | 17.1 ± 2.6 | 20.3 ± 4.1* | 19.2 ± 6.5 | 27.9 ± 9.8* |
|  | E/e' | 42.2 ± 6.2 | 40.9 ± 5.7 | 40.36 ± 4.5 | 38.0 ± 4.9* | 39.4 ± 5.27 | 43.1 ± 4.9* |
|  | E' | 23.3 ± 1.4 | 23.5 ± 2.0 | 22.4 ± 1.29 | 25.2 ± 1.9* | 23.4 ± 1.79 | 23.7 ± 1.35 |
|  | A' | 30.8 ± 4.0 | 29.7 ± 4.1 | 27.3 ± 6.2 | 28.7 ± 6.6 | 29.0 ± 6 | 35.8 ± 5* |
| OVERALL | CO | 246.1 ± 45.3 | 238.7 ± 41.6 | 195.8 ± 61.1 | 219.0 ± 76.7 | 215 ± 51.3 | 246.8 ± 72* |
|  | HR | 293 ± 35 | 298 ± 33 | 275 ± 34.6 | 262 ± 48.1 | 273.1 ± 29 | 308 ± 39* |
|  | SV | 0.84 ± 0.13 | 0.80 ± 0.11 | 0.70 ± 0.16 | 0.82 ± 0.21* | 0.78 ± 0.14 | 0.80 ± 0.19 |

Legend:
FS %: fractional shortening, systolic function;
E m/s: early filling velocity of mitral inflow;
A m/s: late filling velocity of mitral inflow;
E/A: index of LV function;
DT ms: deceleration time of E wave;
DT/E s2/m: mitral deceleration index;
E/DT m/s2: decelaration slope;
s' cm/s TDI: contraction velocity;
e' cm/s TDI: early relaxation velocity;
a' cm/s TDI: late relaxation velocity;
e'/a' index of prevalence of diastolic dysfunction;
E/e': index of LV filling pressure;
CO ml/min: cardiac output;
HR beat/min: heart rate;
SV ml/beat: stroke volume.

Receptor Binding Assay

Radioligand binding to a panel of receptors was carried out by Eurofins on crude membrane preparations according to published procedures and by using appropriate reference standard (Eurofins, CVie 101 compound code PT #1207859, study #AB76416, quote #68407-1, for Cvie Therapeutics Limited, Taiwan (R.OC.) on Mar. 5, 2017). CVie 101 was tested at the concentration of 10 μM. No significant interaction was documented, except for Sodium Channel, site 2 from rat (cat #279510), where a significant response (≥50%) was noted (Table 7).

TABLE 7

Receptor binding assay for CVie 101

| Cat # | Assay name | Batch | Species | Rep | Conc | % inhib |
|---|---|---|---|---|---|---|
| 107480 | ATPase, Ca++, skeletal muscle, pig | 401881 | pig | 2 | 10 μM | 14 |
| 118040 | CYP450, 19 | 401501 | hum | 2 | 10 μM | 36 |
| 124010 | HMG-CoA Reductase | 401548 | hum | 2 | 10 μM | 7 |
| 140010 | Monoamine Oxidase MAO-A | 401605 | hum | 2 | 10 μM | 4 |
| 140120 | Monoamine Oxidase MAO-B | 401606 | hum | 2 | 10 μM | 4 |
| 107300 | Peptidase, Angiotensin Converting Enzyme | 401611 | rabbit | 2 | 10 μM | 5 |
| 164610 | Peptidase, Renin | 401717 | hum | 2 | 10 μM | 3 |
| 152000 | Phosphodiesterase PDE3 | 401702 | hum | 2 | 10 μM | −16 |
| 200510 | Adenosine A1 | 401527 | hum | 2 | 10 μM | −4 |
| 200610 | Adenosine A2A | 401527 | hum | 2 | 10 μM | 0 |
| 203100 | Adrenergic α1A | 401626 | rat | 2 | 10 μM | 1 |
| 203200 | Adrenergic α1B | 401528 | rat | 2 | 10 μM | 0 |
| 203630 | Adrenergic α2A | 401629 | hum | 2 | 10 μM | −7 |
| 204010 | Adrenergic β1 | 401529 | hum | 2 | 10 μM | −4 |
| 204110 | Adrenergic β2 | 401638 | hum | 2 | 10 μM | 1 |
| 204600 | Aldosterone | 401887 | rat | 2 | 10 μM | 6 |
| 206000 | Androgen (Testosterone) | 401738 | hum | 2 | 10 μM | 1 |
| 210030 | Angiotensin AT1 | 401493 | hum | 2 | 10 μM | 12 |
| 210120 | Angiotensin AT2 | 401493 | hum | 2 | 10 μM | −1 |
| 214600 | Calcium Channel L-type, Dihydropyridine | 401530 | rat | 2 | 10 μM | −8 |
| 219500 | Dopamine D1 | 401581 | hum | 2 | 10 μM | −5 |
| 219700 | Dopamine D2s | 401582 | hum | 2 | 10 μM | 4 |
| 219800 | Dopamine D3 | 401573 | hum | 2 | 10 μM | 7 |
| 226010 | Estrogen ERα | 401648 | hum | 2 | 10 μM | 14 |
| 226050 | Estrogen ERβ | 401535 | hum | 2 | 10 μM | 17 |
| 226600 | GABA$_A$, Flunitrazepam, Central | 401654 | rat | 2 | 10 μM | 6 |
| 226500 | GABA$_A$, Muscimol, Central | 401653 | rat | 2 | 10 μM | −9 |
| 232030 | Glucocorticoid | 401564 | hum | 2 | 10 μM | 10 |
| 233000 | Glutamate, NMDA, Phencyclidine | 401525 | rat | 2 | 10 μM | 7 |
| 239610 | Histamine H1 | 401531 | hum | 2 | 10 μM | 13 |
| 241000 | Imidazoline I2, Central | 401657 | rat | 2 | 10 μM | 25 |
| 243000 | Insulin | 401578 | rat | 2 | 10 μM | −7 |
| 252710 | Muscarinic M2 | 401658 | hum | 2 | 10 μM | 7 |
| 252810 | Muscarinic M3 | 401659 | hum | 2 | 10 μM | 15 |
| 253010 | Muscarinic M5 | 401562 | hum | 2 | 10 μM | 21 |
| 258590 | Nicotinic Acetylcholine | 401636 | hum | 2 | 10 μM | 2 |
| 260410 | Opiate μ(OP3, MOP) | 401532 | hum | 2 | 10 μM | 19 |
| 264500 | Phorbol Ester | 401662 | mouse | 2 | 10 μM | −4 |
| 265600 | Potassium Channel (K$_{ATP}$) | 401663 | ham | 2 | 10 μM | −6 |
| 265900 | Potassium Channel hERG | 401868 | hum | 2 | 10 μM | 4 |
| 299005 | Progesterone PR-B | 401590 | hum | 2 | 10 μM | 10 |
| 270300 | Ryanodine RyR3 | 401776 | rat | 2 | 10 μM | 8 |
| 271010 | Serotonin (5-Hydroxy-tryptamine) 5-HT1, non selective | 401498 | rat | 2 | 10 μM | 7 |
| 299007 | Sigma σ2 | 401500 | hum | 2 | 10 μM | 30 |
| 278110 | Sigma σ1 | 401499 | hum | 2 | 10 μM | 23 |
| 279510 | Sodium Channel, Site 2 | 401686 | rat | 2 | 10 μM | 50 |
| 204410 | Transporter, Norepinephrine (NET) | 401639 | hum | 2 | 10 μM | 2 |

Note:
Batch represents compounds tested concurrently in the same assay(s);
bov = Bovine;
ham = Hamster;
hum = Human

The invention claimed is:

1. Compounds of formula (I)

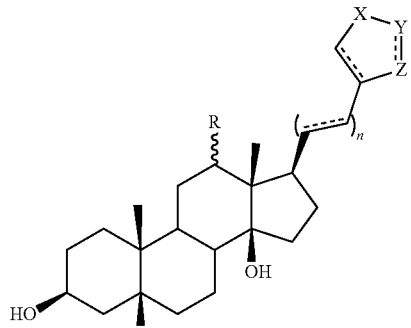

wherein X, Y, Z are annular atoms comprised in a five-membered carbocyclic or heterocyclic ring, selected from the group consisting of CH, NH, N, O, S; and wherein:
n is 0 or 1 and said heterocyclic ring selected from the group consisting of imidazolyl, pyrazolyl, thiazolyl, isoxazolyl, and the corresponding dihydro- and tetra-hydro derivatives;
R is H or OH; and
the dotted line represents an optional double bond C=C; the thick line represents a bond in the β configuration; the wavy line represents a bond both in the α and β configuration; or the pharmaceutically acceptable salts, solvates, or hydrates thereof.

2. Compounds according to claim 1, wherein the heterocycle group in position 17β is substituted by an amino($C_1$-$C_4$) linear or branched alkyl or guanidine or guanidino ($C_1$-$C_4$) linear or branched alkyl.

3. Compounds according to claim 1, wherein R is beta OH.

4. Compounds according to claim 1, wherein the symbol n is 0.

5. Compounds according to claim 1, wherein the symbol n is 1 and there is a single or double bond between the androstane skeleton and the 17β-heterocyclyl or carbocyclyl ring.

6. Compounds according to claim 1, selected from the group consisting of:
- 3β-hydroxy-5β-10β-methyl-13β-methyl-14β-hydroxy-17β-(imidazol-4-yl)androstane;
- 3β-hydroxy-5β-10β-methyl-13β-methyl-14β-hydroxy-17β-(2-guanidino-thiazol-4-yl)androstane;
- 3β-hydroxy-5β-10β-methyl-12β-hydroxy-13β-methyl-14β-hydroxy-17β-(imidazol-4-yl)androstane;
- 3β-hydroxy-5β-10β-methyl-12β-hydroxy-13β-methyl-14β-hydroxy-17β-(2-guanidino-thiazol-4-yl)androstane;
- 3β-hydroxy-5β-10β-methyl-13β-methyl-14β-hydroxy-17β-(N-(3-aminopropyl)-imidazol-4-yl)androstane;
- 3β-hydroxy-5β-10β-methyl-13β-methyl-14β-hydroxy-17β-(pyrazol-3-yl)androstane;
- 3β-hydroxy-5β-10β-methyl-13β-methyl-14β-hydroxy-17β-((5-(3-aminopropyl)-isoxazol-3-yl))androstane;
- 3β-hydroxy-5β-10β-methyl-13β-methyl-14β-hydroxy-17β-((5-(3-aminopropyl)-isoxazol-3-yl)-ethyl)androstane;
- 3β-hydroxy-5β-10β-methyl-13β-methyl-14β-hydroxy-17β-(5-(2-aminoethyl)-isoxazol-3-yl)-ethyl)androstane; and
- 3β-hydroxy-5β-10β-methyl-13β-methyl-14β-hydroxy-17β-(5-(2-aminomethyl)-isoxazol-3-yl)-ethenyl)androstane.

7. Compounds according to claim 1, wherein the pharmaceutically acceptable salt is selected from chloride, bromide, sulfate, phosphate, nitrate, fumarate, succinate, oxalate, malate, tartrate, maleate, citrate, methanesulfonate, or benzoate.

8. A pharmaceutical composition comprising one or more of the compounds of claim 1, in combination with at least one pharmaceutically acceptable vehicle and/or excipient.

9. A pharmaceutical composition according to claim 8, formulated for inhalation, oral administration, intravenous injection, or intramuscular injection.

10. A pharmaceutical composition according to claim 8, further comprising one or more therapeutically active ingredients selected from the group consisting of ACE inhibitors, AIRBs, diuretics, Ca channel blockers, b blockers, digitalis, NO donors, vasodilators, SERCA2a stimulators, neprilisin (NEP) inhibitors, myosin filament activators, recombinant relaxin-2 mediators, recombinant NP protein, activators of the soluble Guanylate Cyclase (sGC), beta-arrestin ligand of Angiotensin II receptor and any combination thereof.

11. A pharmaceutical composition according to claim 10, wherein said diuretic, is selected among furosemide, bumetanide, torasemide, metolazone, an aldosterone antagonist, and thiazide diuretics.

12. A pharmaceutical composition according to claim 10, wherein said ACE inhibitor is Lisinopril or Ramipril.

13. A pharmaceutical composition according to claim 10, wherein said Angiotensin H receptor blocker is valsartan, candesartan, olmesartan, telmisartan or losartan.

14. A pharmaceutical composition according to claim 10, wherein said Angiotensin receptor/neprilysin inhibitor is sacubitril.

15. A pharmaceutical composition according to claim 10, wherein said Beta-blocker is carvedilol or metoprolol.

16. A pharmaceutical composition according to claim 10, wherein said Vasodilator is Hydralazine, Hydralazine combined with isosorbide dinitrate, nitrates, amlodipine, felodipine, or non-dihydropyridines.

17. A pharmaceutical composition according to claim 10, wherein said agent for the treatment of heart failure is selected from Digoxin, entresto, omecantiv, serelaxin, ularitide, or levosimendan.

18. A method of treating or preventing a cardiovascular disorder in an individual, the method comprising the steps of:
(1) providing an individual having a cardiovascular disorder;
(2) measuring one or more indicators of cardiovascular disorders selected from the group consisting of Pulmonary Capillary Wedge Pressure (PCWP), dyspnea, peripheral and pulmonary venous congestion, urinary volume, exercise capacity, serum biomarker NT-proBNP, high sensitive cardiac Troponin (hs-cTnT), heart tissue damage, reduced exercise tolerance, renal insufficiency, oliguria, orthopnea, paroxysmal nocturnal dyspnea, tachypnea, ankle swelling, elevated jugular venous pressure, and any combination thereof; and
(3) administering to the individual a therapeutically effective amount of a pharmaceutical composition comprising one or more of the compounds of claim 1 whereby an improvement in the one or more indicators indicates treatment or prevention of the cardiovascular disorder in the individual.

19. A method of treating an individual having heart failure, the method comprising the steps of:
(1) providing an individual having heart failure;
(2) measuring one or more indicators of heart failure selected from the group consisting of Pulmonary Capillary Wedge Pressure (PCWP), dyspnea, peripheral and pulmonary venous congestion, urinary volume, exercise capacity, serum biomarker NT-proBNP, high sensitive cardiac Troponin (hs-cTnT), heart tissue damage, reduced exercise tolerance, renal insufficiency, oliguria, orthopnea, paroxysmal nocturnal dyspnea, tachypnea, ankle swelling, elevated jugular venous pressure, and any combination thereof; and
(3) administering to the individual a therapeutically effective amount of a pharmaceutical composition comprising one or more of the compounds of claim 1 whereby an improvement in the one or more indicators indicates treatment of heart failure in the individual.

20. The method of claim 19, wherein heart failure is acute or chronic.

* * * * *